(12) United States Patent
Mazur et al.

(10) Patent No.: US 8,568,413 B2
(45) Date of Patent: Oct. 29, 2013

(54) BONE FIXATION DEVICE, TOOLS AND METHODS

(75) Inventors: Kai U. Mazur, Santa Rosa, CA (US); Stephen R. McDaniel, San Francisco, CA (US); Trung Ho Pham, Santa Rosa, CA (US); Charles L. Nelson, Santa Rosa, CA (US); Stephen B. Gunther, Keswick, VA (US); Herber Saravia, San Francisco, CA (US); Robert G. Coleman, Cordova, TN (US)

(73) Assignee: Sonoma Orthopedic Products, Inc., Santa Rosa, CA (US)

( * ) Notice: Subject to any disclaimer, the term of this patent is extended or adjusted under 35 U.S.C. 154(b) by 40 days.

(21) Appl. No.: 12/642,648

(22) Filed: Dec. 18, 2009

(65) Prior Publication Data

US 2011/0087227 A1    Apr. 14, 2011

Related U.S. Application Data

(60) Provisional application No. 61/138,920, filed on Dec. 18, 2008.

(51) Int. Cl.
*A61B 17/56* (2006.01)

(52) U.S. Cl.
USPC .............................................. 606/62; 606/64

(58) Field of Classification Search
USPC ............................. 606/62–68; 411/437, 301
See application file for complete search history.

(56) References Cited

U.S. PATENT DOCUMENTS

| | | |
|---|---|---|
| 958,127 A | 5/1910 | Hufrud |
| 1,169,635 A | 1/1916 | Grimes |
| 1,790,841 A | 2/1931 | Rosen |
| 2,221,498 A * | 11/1940 | Tinnerman ..................... 411/527 |
| 2,502,267 A | 3/1950 | McPherson |

(Continued)

FOREIGN PATENT DOCUMENTS

| | | |
|---|---|---|
| EP | 1582163 A1 | 10/2005 |
| EP | 1815813 A2 | 8/2007 |

OTHER PUBLICATIONS

Definition for "mesh", www.thefreedictionary.com, accessed Jun. 19, 2012.*

*Primary Examiner* — Jan Christopher Merene
(74) *Attorney, Agent, or Firm* — Knobbe, Martens, Olson & Bear, LLP

(57) ABSTRACT

A bone fixation device is provided with an elongate body having a longitudinal axis and having a first state in which at least a portion of the body is flexible and a second state in which the body is generally rigid, an actuateable gripper disposed at one or more locations on the elongated body, a hub located on a proximal end of the elongated body, and an actuator operably connected to the gripper(s) to deploy the gripper(s) from a retracted configuration to an expanded configuration. Methods of repairing a fracture of a bone are also disclosed. One such method comprises inserting a bone fixation device into an intramedullary space of the bone to place at least a portion of an elongate body of the fixation device in a flexible state on one side of the fracture and at least a portion of a hub on another side of the fracture, and operating an actuator to deploy at least one gripper of the fixation device to engage an inner surface of the intramedullary space to anchor the fixation device to the bone. Various hub designs are disclosed that may be used in combination with other fixation device components.

15 Claims, 57 Drawing Sheets

(56) References Cited

U.S. PATENT DOCUMENTS

| | | | | |
|---|---|---|---|---|
| 2,685,877 | A | 8/1954 | Dobelle | |
| 2,896,495 | A * | 7/1959 | Crawford | 411/437 |
| 2,908,309 | A * | 10/1959 | Brill | 411/301 |
| 2,998,007 | A | 8/1961 | Herzog | |
| 3,118,444 | A | 1/1964 | Serrato, Jr. | |
| 3,441,017 | A | 4/1969 | Kaessmann | |
| 3,602,218 | A * | 8/1971 | Riordan et al. | 606/916 |
| 3,760,802 | A | 9/1973 | Fischer et al. | |
| 3,779,239 | A | 12/1973 | Fischer et al. | |
| 3,791,380 | A | 2/1974 | Dawidowski | |
| 3,846,846 | A | 11/1974 | Fischer | |
| 3,986,504 | A | 10/1976 | Avila | |
| 4,050,464 | A | 9/1977 | Hall | |
| 4,065,816 | A | 1/1978 | Sawyer | |
| 4,091,806 | A | 5/1978 | Aginsky | |
| 4,262,665 | A | 4/1981 | Roalstad et al. | |
| 4,275,717 | A | 6/1981 | Bolesky | |
| 4,353,358 | A | 10/1982 | Emerson | |
| 4,622,959 | A | 11/1986 | Marcus | |
| 4,753,657 | A | 6/1988 | Lee et al. | |
| 4,805,595 | A | 2/1989 | Kanbara | |
| 5,057,103 | A | 10/1991 | Davis | |
| 5,458,653 | A | 10/1995 | Davidson | |
| 5,472,444 | A | 12/1995 | Huebner et al. | |
| 5,702,215 | A | 12/1997 | Li | |
| 5,772,663 | A | 6/1998 | Whiteside et al. | |
| 5,807,241 | A | 9/1998 | Heimberger | |
| 5,836,949 | A | 11/1998 | Campbell, Jr. et al. | |
| 5,849,004 | A | 12/1998 | Bramlet | |
| 5,879,352 | A | 3/1999 | Filoso et al. | |
| 5,928,259 | A | 7/1999 | Tovey | |
| 6,019,761 | A * | 2/2000 | Gustilo | 606/62 |
| 6,053,922 | | 4/2000 | Krause et al. | |
| 6,077,264 | A | 6/2000 | Chemello | |
| 6,443,992 | B2 | 9/2002 | Lubinus | |
| 6,447,518 | B1 | 9/2002 | Krause et al. | |
| 6,554,833 | B2 | 4/2003 | Levy et al. | |
| 6,558,388 | B1 | 5/2003 | Bartsch et al. | |
| 6,575,973 | B1 | 6/2003 | Shekalim | |
| 6,648,890 | B2 | 11/2003 | Culbert et al. | |
| 6,688,822 | B2 | 2/2004 | Ritter et al. | |
| 6,695,844 | B2 | 2/2004 | Bramlet et al. | |
| 6,863,692 | B2 | 3/2005 | Meulink | |
| 6,866,455 | B2 | 3/2005 | Hasler | |
| 7,632,277 | B2 * | 12/2009 | Woll et al. | 606/86 R |
| 7,846,162 | B2 | 12/2010 | Nelson et al. | |
| 7,909,825 | B2 | 3/2011 | Saravia et al. | |
| 7,914,533 | B2 * | 3/2011 | Nelson et al. | 606/64 |
| 7,942,875 | B2 | 5/2011 | Nelson et al. | |
| 2002/0161369 | A1 | 10/2002 | Bramlet et al. | |
| 2002/0188297 | A1 | 12/2002 | Dakin et al. | |
| 2003/0045919 | A1 | 3/2003 | Swoyer et al. | |
| 2003/0236529 | A1 | 12/2003 | Shluzas et al. | |
| 2004/0133204 | A1 | 7/2004 | Davies | |
| 2004/0236327 | A1 | 11/2004 | Paul et al. | |
| 2005/0047892 | A1 * | 3/2005 | Bremner | 411/437 |
| 2005/0080425 | A1 | 4/2005 | Bhatnagar et al. | |
| 2005/0165395 | A1 | 7/2005 | Orbay et al. | |
| 2005/0177158 | A1 | 8/2005 | Doubler et al. | |
| 2005/0216007 | A1 | 9/2005 | Woll et al. | |
| 2006/0036248 | A1 | 2/2006 | Ferrante | |
| 2006/0084997 | A1 * | 4/2006 | Dejardin | 606/62 |
| 2006/0247638 | A1 * | 11/2006 | Trieu et al. | 606/69 |
| 2006/0264951 | A1 | 11/2006 | Nelson et al. | |
| 2006/0264952 | A1 * | 11/2006 | Nelson et al. | 606/72 |
| 2007/0123878 | A1 * | 5/2007 | Shaver et al. | 606/64 |
| 2007/0142916 | A1 | 6/2007 | Olson et al. | |
| 2007/0260257 | A1 | 11/2007 | Phan | |
| 2008/0132896 | A1 | 6/2008 | Bowen et al. | |
| 2008/0140078 | A1 | 6/2008 | Nelson et al. | |
| 2008/0161805 | A1 * | 7/2008 | Saravia et al. | 606/60 |
| 2008/0206015 | A1 * | 8/2008 | Ambros | 411/415 |
| 2008/0255560 | A1 | 10/2008 | Myers et al. | |
| 2008/0262495 | A1 | 10/2008 | Coati et al. | |
| 2008/0269751 | A1 * | 10/2008 | Matityahu | 606/64 |
| 2008/0287951 | A1 * | 11/2008 | Stoneburner et al. | 606/63 |
| 2009/0018542 | A1 | 1/2009 | Saravia et al. | |
| 2009/0182336 | A1 | 7/2009 | Brenzel et al. | |
| 2009/0228007 | A1 | 9/2009 | Justin et al. | |
| 2009/0228008 | A1 | 9/2009 | Justin et al. | |
| 2010/0023010 | A1 | 1/2010 | Nelson et al. | |
| 2010/0094347 | A1 | 4/2010 | Nelson et al. | |
| 2011/0144645 | A1 | 6/2011 | Saravia et al. | |
| 2011/0178520 | A1 | 7/2011 | Taylor et al. | |
| 2011/0190832 | A1 | 8/2011 | Taylor et al. | |
| 2011/0218585 | A1 | 9/2011 | Krinke et al. | |
| 2011/0218626 | A1 | 9/2011 | Krinke et al. | |
| 2011/0282346 | A1 | 11/2011 | Pham et al. | |

* cited by examiner

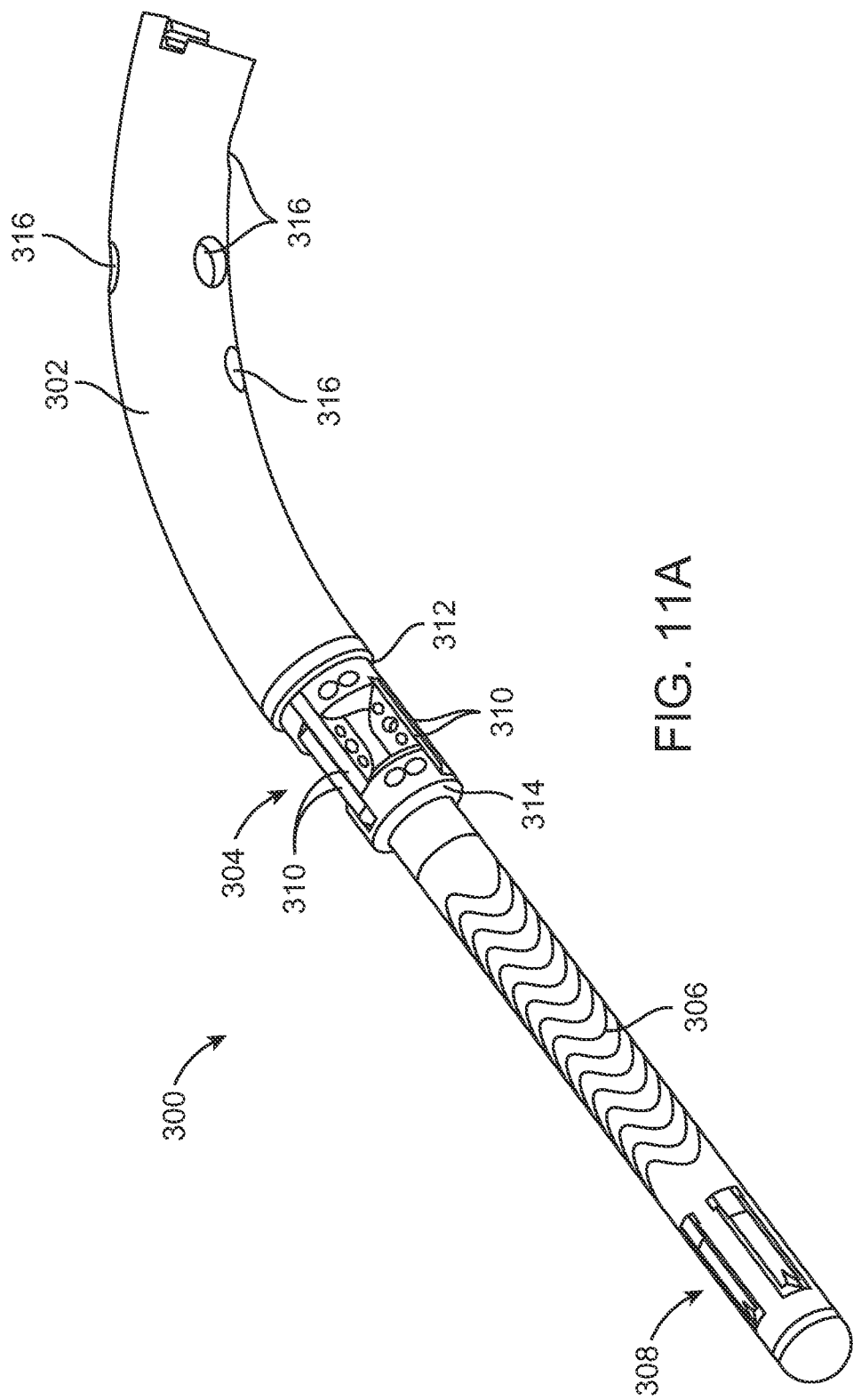

BONE FIXATION DEVICE, TOOLS AND METHODS

CROSS-REFERENCE TO RELATED APPLICATIONS

This application claims benefit to U.S. Provisional Application No. 61/138,920 filed Dec. 18, 2008 and entitled, "BONE FIXATION DEVICE, TOOLS AND METHODS."

INCORPORATION BY REFERENCE

This application is related to: U.S. application Ser. No. 11/383,269 filed May 15, 2006, entitled, "MINIMALLY INVASIVE ACTUABLE BONE FIXATION DEVICES"; U.S. application Ser. No. 11/944,366 filed Nov. 21, 2007, entitled, "FRACTURE FIXATION DEVICE, TOOLS AND METHODS"; U.S. application Ser. No. 12/482,388, filed Jun. 10, 2009, entitled, "FRACTURE FIXATION DEVICE, TOOLS AND METHODS"; U.S. application Ser. No. 12/482,395 filed on Jun. 10, 2009 entitled, "FRACTURE FIXATION DEVICE, TOOLS AND METHODS" and U.S. application Ser. No. 12/482,406 filed on Jun. 10, 2009, entitled, "FRACTURE FIXATION DEVICE, TOOLS AND METHODS," all of which are incorporated herein by reference. All publications and patent applications mentioned in this specification are herein incorporated by reference to the same extent as if each individual publication or patent application was specifically and individually indicated to be incorporated by reference

BACKGROUND OF THE INVENTION

The present invention relates to devices, tools and methods for providing reinforcement of bones. More specifically, the present invention relates to devices, tools and methods for providing reconstruction and reinforcement of bones, including diseased, osteoporotic and fractured bones.

Bone fractures are a common medical condition both in the young and old segments of the population. However, with an increasingly aging population, osteoporosis has become more of a significant medical concern in part due to the risk of osteoporotic fractures. Osteoporosis and osteoarthritis are among the most common conditions to affect the musculoskeletal system, as well as frequent causes of locomotor pain and disability. Osteoporosis can occur in both human and animal subjects (e.g. horses). Osteoporosis (OP) and osteoarthritis (OA) occur in a substantial portion of the human population over the age of fifty. The National Osteoporosis Foundation estimates that as many as 44 million Americans are affected by osteoporosis and low bone mass, leading to fractures in more than 300,000 people over the age of 65. In 1997 the estimated cost for osteoporosis related fractures was $13 billion. That figure increased to $17 billion in 2002 and is projected to increase to $210-240 billion by 2040. Currently it is expected that one in two women, and one in four men, over the age of 50 will suffer an osteoporosis-related fracture. Osteoporosis is the most important underlying cause of fracture in the elderly. Also, sports and work-related accidents account for a significant number of bone fractures seen in emergency rooms among all age groups.

One current treatment of bone fractures includes surgically resetting the fractured bone. After the surgical procedure, the fractured area of the body (i.e., where the fractured bone is located) is often placed in an external cast for an extended period of time to ensure that the fractured bone heals properly. This can take several months for the bone to heal and for the patient to remove the cast before resuming normal activities.

In some instances, an intramedullary (IM) rod or nail is used to align and stabilize the fracture. In that instance, a metal rod is placed inside a canal of a bone and fixed in place, typically at both ends. See, for example, Fixion™ IM (Nail), www.disc-o-tech.com. This approach requires incision, access to the canal, and placement of the IM nail. The nail can be subsequently removed or left in place. A conventional IM nail procedure requires a similar, but possibly larger, opening to the space, a long metallic nail being placed across the fracture, and either subsequent removal, and or when the nail is not removed, a long term implant of the IM nail. The outer diameter of the IM nail must be selected for the minimum inside diameter of the space. Therefore, portions of the IM nail may not be in contact with the canal. Further, micromotion between the bone and the IM nail may cause pain or necrosis of the bone. In still other cases, infection can occur. The IM nail may be removed after the fracture has healed. This requires a subsequent surgery with all of the complications and risks of a later intrusive procedure. In general, rigid IM rods or nails are difficult to insert, can damage the bone and require additional incisions for cross-screws to attach the rods or nails to the bone.

Some IM nails are inflatable. See, for example, Meta-Fix IM Nailing System, www.disc-o-tech.com. Such IM nails require inflating the rod with very high pressures, endangering the surrounding bone. Inflatable nails have many of the same drawbacks as the rigid IM nails described above.

External fixation is another technique employed to repair fractures. In this approach, a rod may traverse the fracture site outside of the epidermis. The rod is attached to the bone with trans-dermal screws. If external fixation is used, the patient will have multiple incisions, screws, and trans-dermal infection paths. Furthermore, the external fixation is cosmetically intrusive, bulky, and prone to painful inadvertent manipulation by environmental conditions such as, for example, bumping into objects and laying on the device.

Other concepts relating to bone repair are disclosed in, for example, U.S. Pat. No. 5,108,404 to Scholten for Surgical Protocol for Fixation of Bone Using Inflatable Device; U.S. Pat. No. 4,453,539 to Raftopoulos et al. for Expandable Intramedullary Nail for the Fixation of Bone Fractures; U.S. Pat. No. 4,854,312 to Raftopolous for Expanding Nail; U.S. Pat. No. 4,932,969 to Frey et al. for Joint Endoprosthesis; U.S. Pat. No. 5,571,189 to Kuslich for Expandable Fabric Implant for Stabilizing the Spinal Motion Segment; U.S. Pat. No. 4,522,200 to Stednitz for Adjustable Rod; U.S. Pat. No. 4,204,531 to Aginsky for Nail with Expanding Mechanism; U.S. Pat. No. 5,480,400 to Berger for Method and Device for Internal Fixation of Bone Fractures; U.S. Pat. No. 5,102,413 to Poddar for Inflatable Bone Fixation Device; U.S. Pat. No. 5,303,718 to Krajicek for Method and Device for the Osteosynthesis of Bones; U.S. Pat. No. 6,358,283 to Hogfors et al. for Implantable Device for Lengthening and Correcting Malpositions of Skeletal Bones; U.S. Pat. No. 6,127,597 to Beyar et al. for Systems for Percutaneous Bone and Spinal Stabilization, Fixation and Repair; U.S. Pat. No. 6,527,775 to Warburton for Interlocking Fixation Device for the Distal Radius; U.S. Patent Publication US2006/0084998 A1 to Levy et al. for Expandable Orthopedic Device; and PCT Publication WO 2005/112804 A1 to Myers Surgical Solutions, LLC for Fracture Fixation and Site Stabilization System. Other fracture fixation devices, and tools for deploying fracture fixation devices, have been described in: US Patent Appl. Publ. No. 2006/0254950; U.S. Ser. No. 60/867,011 (filed Nov. 22, 2006); U.S. Ser. No. 60/866,976 (filed Nov. 22, 2006); and U.S. Ser. No. 60/866,920 (filed Nov. 22, 2006).

In view of the foregoing, it would be desirable to have a device, system and method for providing effective and minimally invasive bone reinforcement and fracture fixation to treat fractured or diseased bones, while improving the ease of insertion, eliminating cross-screw incisions and minimizing trauma.

SUMMARY OF THE INVENTION

Aspects of the invention relate to embodiments of a bone fixation device and to methods for using such a device for repairing a bone fracture. The bone fixation device may include an elongate body with a longitudinal axis and having a flexible state and a rigid state. The device further may include a plurality of grippers disposed at longitudinally-spaced locations along the elongated body, a rigid hub connected to the elongated body, and an actuator that is operably-connected to the grippers to deploy the grippers from a first shape to an expanded second shape.

In one embodiment, a bone fixation device is provided with an elongate body having a longitudinal axis and having a first state in which at least a portion of the body is flexible and a second state in which the body is generally rigid, an actuateable gripper disposed at a distal location on the elongated body, a hub located on a proximal end of the elongated body, and an actuator operably connected to the gripper to deploy the gripper from a retracted configuration to an expanded configuration.

Methods of repairing a fracture of a bone are also disclosed. One such method comprises inserting a bone fixation device into an intramedullary space of the bone to place at least a portion of an elongate body of the fixation device in a flexible state on one side of the fracture and at least a portion of a hub on another side of the fracture, and operating an actuator to deploy at least one gripper of the fixation device to engage an inner surface of the intramedullary space to anchor the fixation device to the bone.

One embodiment of the present invention provides a low weight to volume mechanical support for fixation, reinforcement and reconstruction of bone or other regions of the musculo-skeletal system in both humans and animals. The method of delivery of the device is another aspect of the invention. The method of delivery of the device in accordance with the various embodiments of the invention reduces the trauma created during surgery, decreasing the risks associated with infection and thereby decreasing the recuperation time of the patient. The framework may in one embodiment include an expandable and contractible structure to penult re-placement and removal of the reinforcement structure or framework.

In accordance with the various embodiments of the present invention, the mechanical supporting framework or device may be made from a variety of materials such as metal, composite, plastic or amorphous materials, which include, but are not limited to, steel, stainless steel, cobalt chromium plated steel, titanium, nickel titanium alloy (nitinol), super-elastic alloy, and polymethylmethacrylate (PMMA). The device may also include other polymeric materials that are biocompatible and provide mechanical strength, that include polymeric material with ability to carry and delivery therapeutic agents, that include bioabsorbable properties, as well as composite materials and composite materials of titanium and polyetheretherketone (PEEK™), composite materials of polymers and minerals, composite materials of polymers and glass fibers, composite materials of metal, polymer, and minerals.

Within the scope of the present invention, each of the aforementioned types of device may further be coated with proteins from synthetic or animal source, or include collagen coated structures, and radioactive or brachytherapy materials. Furthermore, the construction of the supporting framework or device may include radio-opaque markers or components that assist in their location during and after placement in the bone or other region of the musculo-skeletal systems.

Further, the reinforcement device may, in one embodiment, be osteo incorporating, such that the reinforcement device may be integrated into the bone.

In still another embodiment of the invention, a method of repairing a bone fracture is disclosed that comprises: accessing a fracture along a length of a bone through a bony protuberance at an access point at an end of a bone; advancing a bone fixation device into a space through the access point at the end of the bone; bending a portion of the bone fixation device along its length to traverse the fracture; and locking the bone fixation device into place within the space of the bone. The method can also include the step of advancing an obturator through the bony protuberance and across the fracture prior to advancing the bone fixation device into the space. In yet another embodiment of the method, the step of anchoring the bone fixation device within the space can be included.

An aspect of the invention discloses a removable bone fixation device that uses a single port of insertion and has a single-end of remote actuation wherein a bone fixation device stabilizes bone after it has traversed the fracture. The bone fixation device is adapted to provide a single end in one area or location where the device initiates interaction with bone. The device can be deployed such that the device interacts with bone. Single portal insertion and single-end remote actuation enables the surgeon to insert and deploy the device, deactivate and remove the device, reduce bone fractures, displace or compress the bone, and lock the device in place. In addition, the single-end actuation enables the device to grip bone, compresses the rigidizable flexible body, permits axial, torsional and angular adjustments to its position during surgery, and releases the device from the bone during its removal procedure. A removable extractor can be provided in some embodiments of the device to enable the device to be placed and extracted by deployment and remote actuation from a single end. The device of the invention can be adapted and configured to provide at least one rigidizable flexible body or sleeve. Further the body can be configured to be flexible in all angles and directions. The flexibility provided is in selective planes and angles in the Cartesian, polar, or cylindrical coordinate systems. Further, in some embodiments, the body is configured to have a remote actuation at a single end. Additionally, the body can be configured to have apertures, windings, etc. The device may be configured to function with non-flexible bodies for use in bones that have a substantially straight segment or curved segments with a constant radius of curvature. Another aspect of the invention includes a bone fixation device in that has mechanical geometry that interacts with bone by a change in the size of at least one dimension of a Cartesian, polar, or spherical coordinate system. Further, in some embodiments, bioabsorbable materials can be used in conjunction with the devices, for example by providing specific subcomponents of the device configured from bioabsorbable materials. A sleeve can be provided in some embodiments where the sleeve is removable, has deployment, remote actuation, and a single end. Where a sleeve is employed, the sleeve can be adapted to provide a deployable interdigitation process or to provide an aperture along its length through which the deployable interdigitation process is adapted to engage bone. In some embodiments, the deployable interdigitation process is further adapted to engage bone when actuated by the sleeve. In some embodiments, the bone fixation device further comprises a cantilever adapted to retain the deployable bone fixation device within the space. The sleeve can further be adapted to be expanded and collapsed within the space by a user. One end of the device can be configured to provide a blunt obturator surface adapted to advance into the bone. A guiding tip may also be provided that facilitates guiding the device through the bone. Further, the deployable bone fixation device can be adapted to receive external stimulation to provide therapy to the bone. The device can further be adapted to provide an integral stimulator which provides therapy to the bone. In still other embodiments, the device can be adapted to receive deliver therapeutic stimulation to the bone.

The devices disclosed herein may be employed in various regions of the body, including: cranial, thoracic, lower extremities and upper extremities. Additionally, the devices are suitable for a variety of breaks including, metaphyseal and diaphyseal.

The fracture fixation devices of various embodiments of the invention are adapted to be inserted through an opening of a fractured bone, such as the radius (e.g., through a bony protuberance on a distal or proximal end or through the mid-shaft) into the intramedullary canal of the bone. In some embodiments, the fixation device has two main components, one configured component for being disposed on the side of the fracture closest to the opening and one component configured for being disposed on the other side of the fracture from the opening so that the fixation device traverses the fracture.

The device components cooperate to align, fix and/or reduce the fracture so as to promote healing. The device may be removed from the bone after insertion (e.g., after the fracture has healed or for other reasons), or it may be left in the bone for an extended period of time or permanently.

In some embodiments, the fracture fixation device has one or more actuatable anchors or grippers on its proximal and/or distal ends. These anchors may be used to hold the fixation device to the bone while the bone heals.

In some embodiments, to aid in insertion into the intramedullary canal, at least one component of the fracture fixation device has a substantially flexible state and a substantially rigid state. Once in place, deployment of the device also causes the components to change from the flexible state to a rigid state to aid in proper fixation of the fracture. At least one of the components may be substantially rigid or semi-flexible. At least one component may provide a bone screw attachment site for the fixation device.

Embodiments of the invention also provide deployment tools with a tool guide for precise alignment of one or more bone screws with the fracture fixation device. These embodiments also provide bone screw orientation flexibility so that the clinician can select an orientation for the bone screw(s) that will engage the fixation device as well as any desired bone fragments or other bone or tissue locations.

These and other features and advantages of the present invention will be understood upon consideration of the following detailed description of the invention and the accompanying drawings.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 11A is perspective view of another embodiment of a bone fixation device shown in a retracted or undeployed state.

DETAILED DESCRIPTION OF THE INVENTION

By way of background and to provide context for the invention, it may be useful to understand that bone is often described as a specialized connective tissue that serves three major functions anatomically. First, bone provides a mechanical function by providing structure and muscular attachment for movement. Second, bone provides a metabolic function by providing a reserve for calcium and phosphate. Finally, bone provides a protective function by enclosing bone marrow and vital organs. Bones can be categorized as long bones (e.g. radius, femur, tibia and humerus) and flat bones (e.g. skull, scapula and mandible). Each bone type has a different embryological template. Further each bone type contains cortical and trabecular bone in varying proportions. The devices of this invention can be adapted for use in any of the bones of the body as will be appreciated by those skilled in the art.

Cortical bone (compact) forms the shaft, or diaphysis, of long bones and the outer shell of flat bones. The cortical bone provides the main mechanical and protective function. The trabecular bone (cancellous) is found at the end of the long bones, or the epiphysis, and inside the cortex of flat bones. The trabecular bone consists of a network of interconnecting trabecular plates and rods and is the major site of bone remodeling and resorption for mineral homeostasis. During development, the zone of growth between the epiphysis and diaphysis is the metaphysis. Finally, woven bone, which lacks the organized structure of cortical or cancellous bone, is the first bone laid down during fracture repair. Once a bone is fractured, the bone segments are positioned in proximity to each other in a manner that enables woven bone to be laid down on the surface of the fracture. This description of anatomy and physiology is provided in order to facilitate an understanding of the invention. Persons of skill in the art will also appreciate that the scope and nature of the invention is not limited by the anatomy discussion provided. Further, it will be appreciated there can be variations in anatomical characteristics of an individual patient, as a result of a variety of factors, which are not described herein. Further, it will be appreciated there can be variations in anatomical characteristics between bones which are not described herein.

Figure 1:
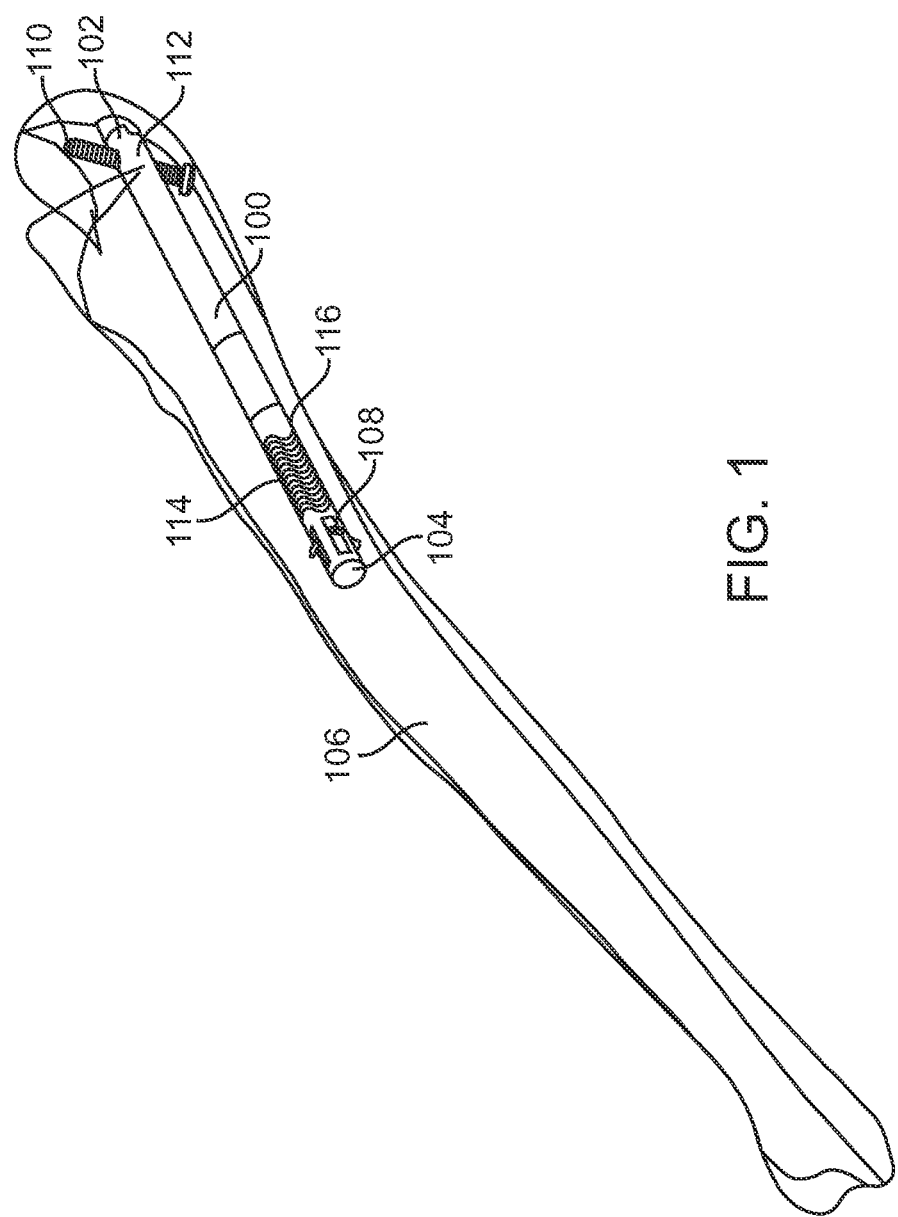
FIG. 1 is a perspective view of an embodiment of a bone fixation device implanted in a bone according to the invention.
Figure 2:
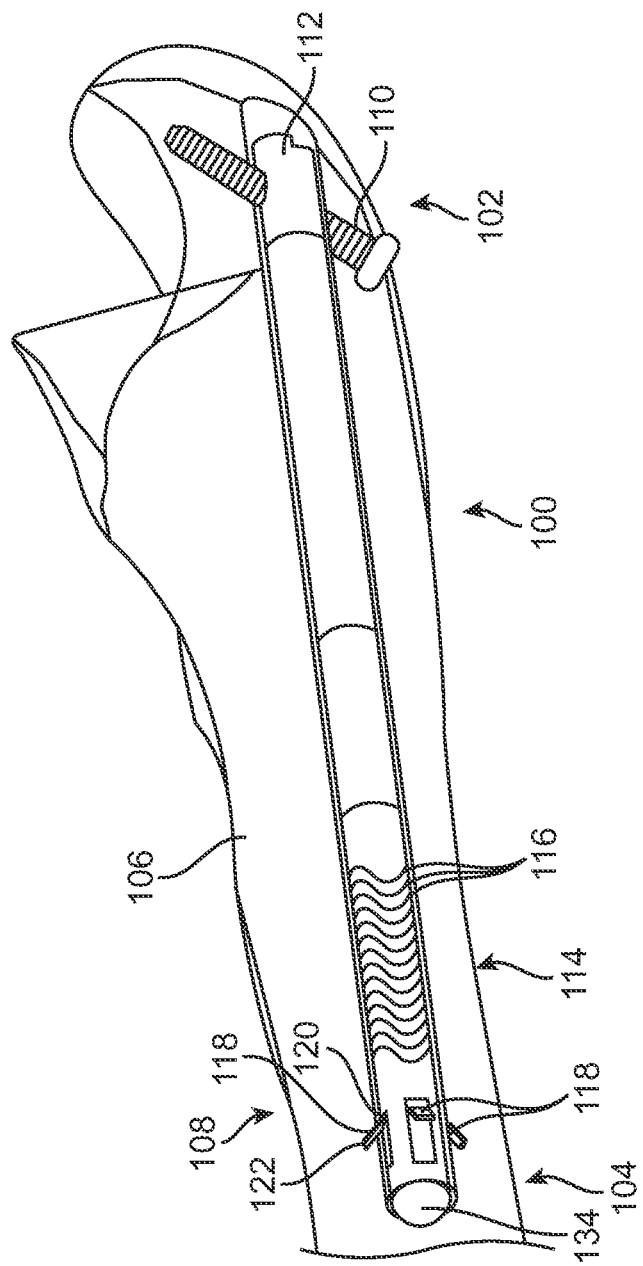
FIG. 2 is another perspective view of the implanted device of FIG. 1.

FIGS. 1 and 2 are perspective views of an embodiment of a bone fixation device 100 having a proximal end 102 (nearest the surgeon) and a distal end 104 (further from surgeon) and positioned within the bone space of a patient according to the invention. In this example, device 100 is shown implanted in the upper (or proximal) end of an ulna 106. The proximal end and distal end, as used in this context, refers to the position of an end of the device relative to the remainder of the device or the opposing end as it appears in the drawing. The proximal end can be used to refer to the end manipulated by the user or physician. The distal end can be used to refer to the end of the device that is inserted and advanced within the bone and is furthest away from the physician. As will be appreciated by those skilled in the art, the use of proximal and distal could change in another context, e.g. the anatomical context in which proximal and distal use the patient as reference, or where the entry point is distal from the surgeon.

When implanted within a patient, the device can be held in place with suitable fasteners such as wire, screws, nails, bolts, nuts and/or washers. The device 100 is used for fixation of fractures of the proximal or distal end of long bones such as intracapsular, intertrochanteric, intercervical, supracondular, or condular fractures of the femur; for fusion of a joint; or for surgical procedures that involve cutting a bone. The devices 100 may be implanted or attached through the skin so that a pulling force (traction may be applied to the skeletal system).

Figure 3:
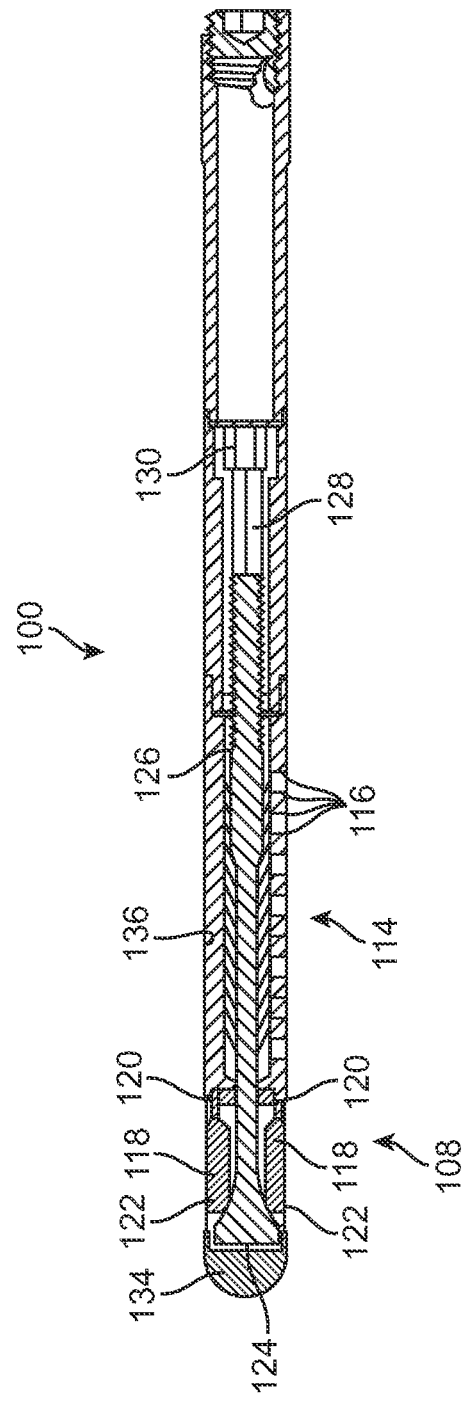
FIG. 3 is a longitudinal cross-section view of the bone fixation device of FIG. 1 in a non-deployed state.

In the embodiment shown in FIG. 1, the design of the metaphyseal fixation device 100 depicted is adapted to provide a bone engaging mechanism or gripper 108 adapted to engage target bone of a patient from the inside of the bone. As configured for this anatomical application, the device is designed to facilitate bone healing when placed in the intramedullary space within a post fractured bone. This device 100 has a gripper 108 positioned distally and shown deployed radially outward against the wall of the intramedullary cavity. On entry into the cavity, gripper 108 is flat and retracted (FIG. 3). Upon deployment, gripper 108 pivots radially outward and grips the diaphyseal bone from the inside of the bone. One or more screws 110 placed through apertures through the hub 112 lock the device 100 to the metaphyseal bone. Hence, the metaphysis and the diaphysis are joined. A flexible-to-rigid body portion 114 may also be provided, and in this embodiment is positioned between gripper 108 and hub 112. It may be provided with wavy spiral cuts 116 for that purpose, as will be described in more detail below.

FIG. 3 shows a longitudinal cross-section of device 100 in a non-deployed configuration. In this embodiment, gripper 108 includes two pairs of opposing bendable gripping members 118. Two of the bendable gripping members 118 are shown in FIG. 3, while the other two (not shown in FIG. 3) are located at the same axial location but offset by 90 degrees. Each bendable gripping member 118 has a thinned portion 120 that permits bending as the opposite distal end 122 of member 118 is urged radially outward, such that member 118 pivots about thinned portion 120. When extended, distal ends 122 of bendable members 118 contact the inside of the bone to anchor the distal portion of device 100 to the bone. In alternative embodiments (not shown), the gripper may comprise 1, 2, 3, 4, 5, 6 or more bendable members similar to members 118 shown.

During actuation, bendable members 118 of gripper 108 are urged radially outward by a ramped surface on actuator head 124. Actuator head 124 is formed on the distal end of actuator 126. The proximal end of actuator 126 is threaded to engage a threaded bore of drive member 128. The proximal end of drive member 128 is provided with a keyed socket 130 for receiving the tip of a rotary driver tool 132 (shown in FIG. 5) through the proximal bore of device 100. As rotary driver tool 132 turns drive member 128, actuator 126 is drawn in a proximal direction to outwardly actuate gripper members 118.

A hemispherical tip cover 134 may be provided at the distal end of the device as shown to act as a blunt obturator. This arrangement facilitates penetration of bone (e.g. an intramedullary space) by device 100 while keeping the tip of device 100 from digging into bone during insertion.

As previously mentioned, device 100 may include one or more flexible-to-rigid body portions 114. This feature is flexible upon entry into bone and rigid upon application of compressive axial force provided by tensioning actuator 126. Various embodiments of a flexible-to-rigid portion may be used, including dual helical springs whose inner and outer tubular components coil in opposite directions, a chain of ball bearings with flats or roughened surfaces, a chain of cylinders with flats, features, cones, spherical or pointed interdigitating surfaces, wavy-helical cut tubes, two helical cut tubes in opposite directions, linear wires with interdigitating coils, and bellows-like structures.

The design of the flexible-to-rigid tubular body portion 114 allows a single-piece design to maximize the transformation of the same body from a very flexible member that minimizes strength in bending to a rigid body that maximizes strength in bending and torsion. The flexible member transforms to a rigid member when compressive forces are applied in the axial direction at each end, such as by an actuator similar to 126. The body portion 114 is made, for example, by a near-helical cut 116 on a tubular member at an angle of incidence to the axis somewhere between 0 and 180 degrees from the longitudinal axis of the tubular body portion 114. The near-helical cut or wavy-helical cut may be formed by the superposition of a helical curve added to a cyclic curve that produces waves of frequencies equal or greater than zero per turn around the circumference and with cyclic amplitude greater than zero. The waves of one segment nest with those on either side of it, thus increasing the torque, bending strength and stiffness of the tubular body when subjective to compressive forces. The tapered surfaces formed by the incident angle allow each turn to overlap or interdigitate with the segment on either side of it, thus increasing the bending strength when the body is in compression. Additionally, the cuts can be altered in depth and distance between the cuts on the longitudinal axis along the length of body portion 114 to variably alter the flexible-to-rigid characteristics of the tubular body along its length.

The cuts 116 in body portion 114 allow an otherwise rigid member to increase its flexibility to a large degree during deployment. The tubular member can have constant or varying internal and external diameters. This design reduces the number of parts of the flexible-to-rigid body portion of the device and allows insertion and extraction of the device through a curved entry port in the bone while maximizing its rigidity once inserted. Application and removal of compressive forces provided by a parallel member such as wire(s), tension ribbons, a sheath, wound flexible cable, or actuator 126 as shown will transform the body from flexible to rigid and vice versa.

Figure 9:
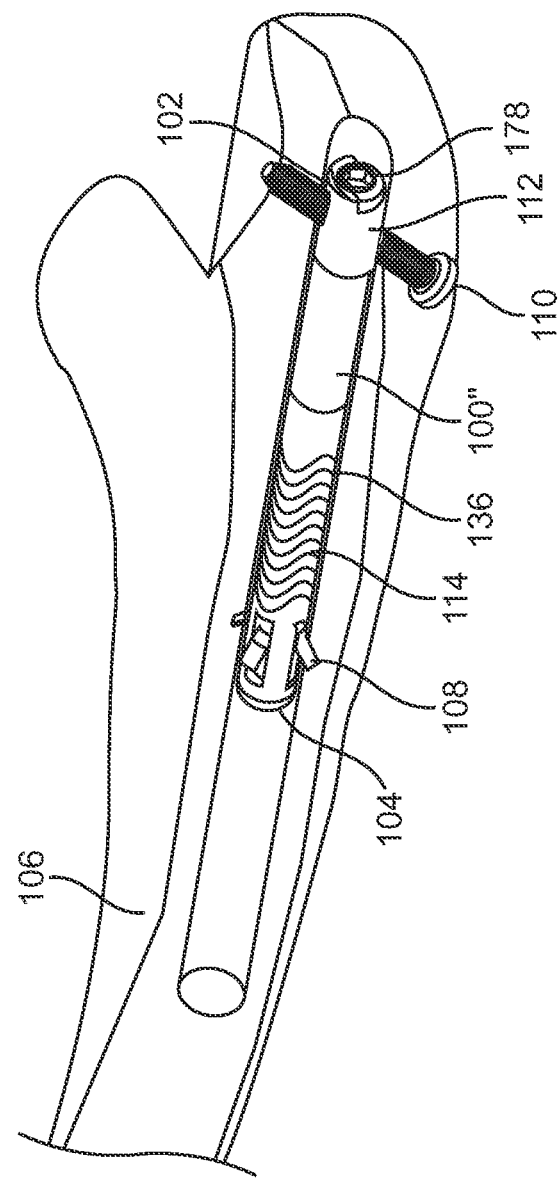
FIG. 9 is a perspective view of another alternative embodiment of the implanted device of FIG. 1.

In operation, as actuator 126 is tightened, gripper members 118 are extended radially outwardly. Once the distal ends of gripper members 118 contact bone and stop moving outward, continued rotation of actuator 126 draws the proximal end 102 and the distal end 104 of device 100 closer together until cuts 116 are substantially closed. As this happens, body portion 114 changes from being flexible to rigid to better secure the bone fracture(s), as will be further described below. Rotating drive member 128 in the opposite direction causes body portion 114 to change from a rigid to a flexible state, such as for removing device 100 if needed in the initial procedure or during a subsequent procedure after the bone fracture(s) have partially or completely healed. Body portion 114 may be provided with a solid longitudinal portion 136 (as best seen in FIGS. 3 and 9) such that cuts 116 are a series of individual cuts each traversing less than 360 degrees in circumference, rather than a single, continuous helical cut. This solid portion 136 can aid in removal of device 100 by keeping body portion 114 from extending axially like a spring.

Figure 4:
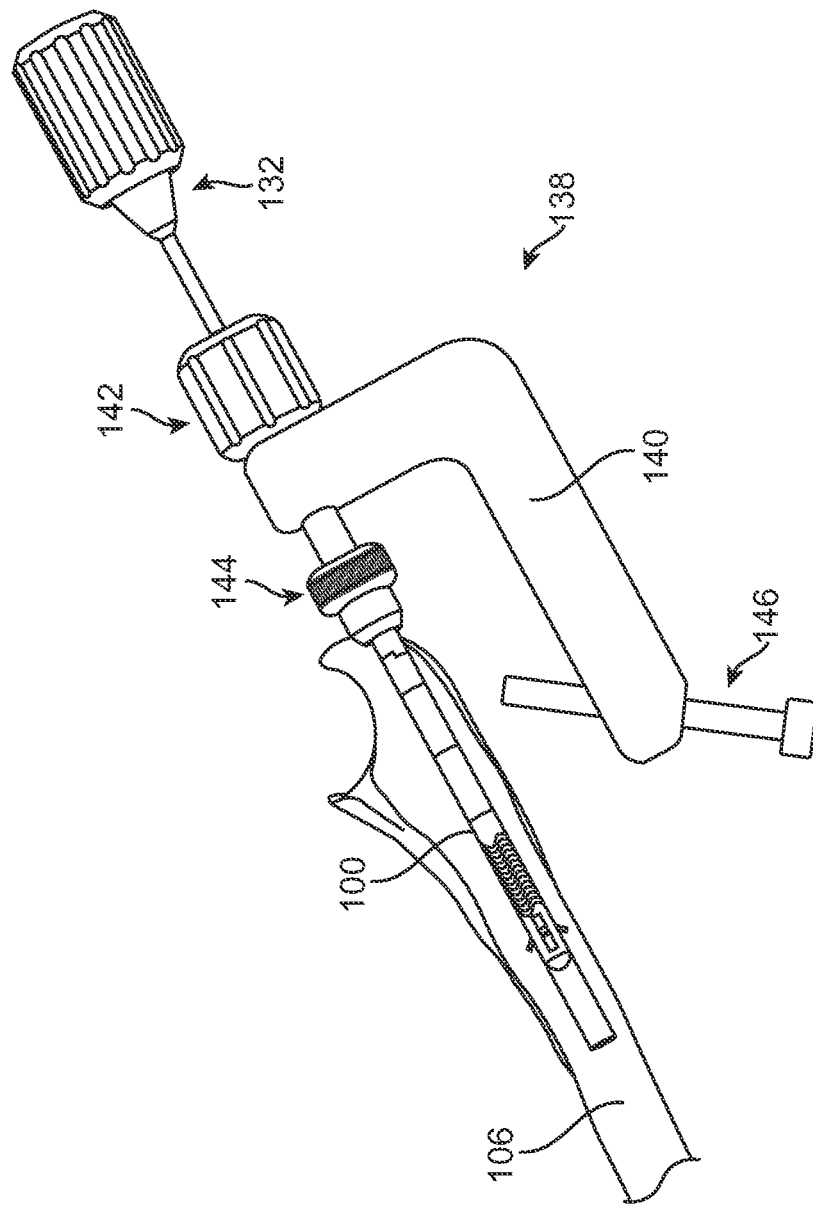
FIG. 4 is a plan view of a combination deployment tool that may be used with the bone fixation device of FIG. 1.

FIG. 4 illustrates a combination tool 138 useful for inserting device 100, actuating gripper 108, compressing flexible-to-rigid body portion 114, approximating the fracture in bone 106, aligning anchor screw(s) 110, and removing device 100, if desired. In this exemplary embodiment, tool 138 includes an L-shaped body 140 that mounts the other components of the tool and also serves as a handle. The main components of tool 138 are a device attachment portion 142, a rotary driver 132, an approximating driver 144, and a screw alignment portion 146.

Figure 5:
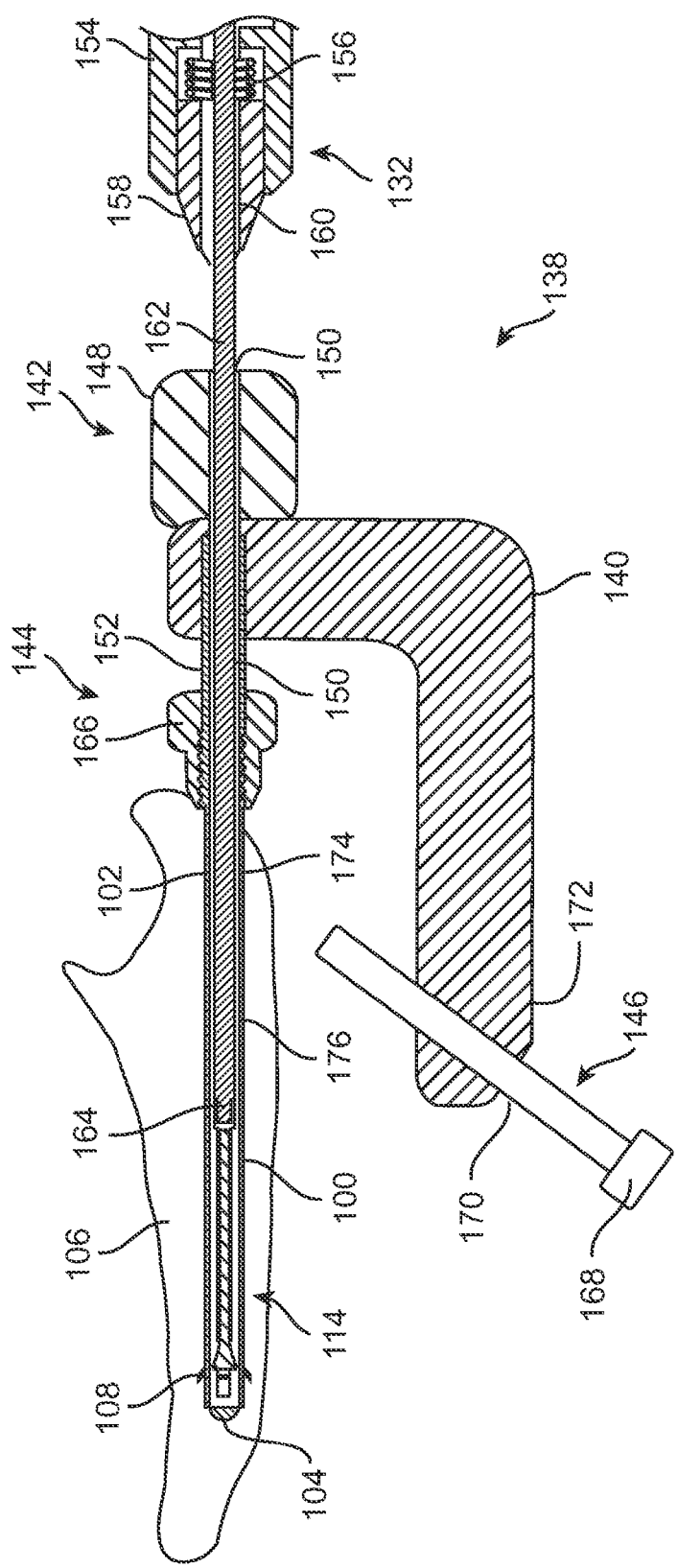
FIG. 5 is a cross-section view of the tool and device shown in FIG. 4.

FIG. 5 shows a cross-section of the tool 138 and device 100 illustrated in FIG. 4. As shown, device attachment portion 142 includes a knob 148 rigidly coupled to a tube 150 which is rotatably mounted within sleeve 152. Sleeve 152 in turn is fixedly mounted to tool body 140. The distal end of tube 150 is provided with external threads for engaging the internal threads on the proximal end of device 100. As best seen in FIG. 4, both the distal end of sleeve 152 and the proximal end of device 100 may be provided with semicircular steps that inter-engage to prevent device 100 from rotating with respect to sleeve 152. With this arrangement, device 100 can be prevented from rotating when it is secured to tool 138 by tube 150 of device attachment portion 142. The mating semicircular steps also serve to position device 100 in a particular axial and angular orientation with respect to tool 138 for aligning screws with screw holes, as will be later described.

Rotary driver 132 may be used to actuate gripper 108 and compress flexible-to-rigid body portion 114 after device 100 is inserted into bone 106. Driver 132 may also be used to allow body portion 114 to decompress and gripper 108 to retract if removal of device 100 from bone 106 is desired. In the embodiment shown, driver 132 includes knob 154, torsion spring 156, hub 158, bushing 160 and shaft 162. The distal end of shaft 162 is provided with a mating tip 164, such as one having a hex-key shape, for engaging with keyed socket 130 of device 100 (best seen in FIG. 3), such that turning driver shaft 162 turns drive member 128 and axially actuates actuator 126, as described above.

The proximal end of shaft 162 may be fitted with a bushing 160, such as with a press-fit. Hub 158 may be secured over bushing 160, such as with a pin through bushing 160 and shaft 162. In this embodiment, knob 154 is rotatably mounted over hub 158 and bushing 160 such that knob 154 can rotate independently from shaft 162. A torsion spring 156 may be used to couple knob 154 to hub 158 as shown to create a torque limiting and/or torque measuring driver. With this indirect coupling arrangement, as knob 154 is rotated about shaft 162, spring 156 urges hub 158 and shaft 162 to rotate in the same direction. Rotational resistance applied by device 100 to shaft tip 164 will increase in this embodiment as gripper 108 engages bone 106, and flexible-to-rigid body portion 114 compresses. As more torque is applied to knob 154, it will advance rotationally with respect to hub 158 as torsion spring 156 undergoes more stress. Markings may be provided on knob 154 and hub 158 to indicate the torque being applied. In this manner, a surgeon can use driver 132 to apply torque to device 100 in a predetermined range. This can help ensure that gripper 108 is adequately set in bone 106, body portion 114 is sufficiently compressed, and excessive torque is not being applied that might damage device 100, bone 106 or cause slippage therebetween. A slip clutch or other mechanism may be provided to allow the applied torque to be limited or indicated. For example, driver 132 may be configured to "click" into or out of a detent position when a desired torque is reached, thus allowing the surgeon to apply a desired torque without needing to observe any indicia on the driver. In alternative embodiments, the driver knob may be selectably or permanently coupled to shaft 162 directly.

After device 100 is inserted in bone 106 and deployed with tool 138 as described above, the approximating driver portion 144 of tool 138 may be used to compress one or more fractures in bone 106. Approximating driver 144 includes knob 166 located on sleeve 152. Knob 166 may be knurled on an outer circumference, and have threads on at least a portion of its axial bore. The internal threads of knob 166 engage with mating external threads on sleeve 152 such that when knob 166 is rotated it advances axially with respect to sleeve 152. When device 100 is anchored in bone 106, sleeve 152 is prevented from moving away from the bone. Accordingly, as knob 166 is advanced axially toward bone 106, it serves to approximate bone fractures located between gripper 108 and knob 166. Suitable thread pitch and knob circumference may be selected to allow a surgeon to supply a desired approximating force to bone 106 by using a reasonable rotation force on knob 166. In alternative embodiments (not shown), a torque indicating and/or torque limiting mechanism as described above may be incorporated into approximating driver 144.

As previously indicated, tool 138 may also include a screw alignment portion 146. In the embodiment depicted in the figures, alignment portion 146 includes a removable alignment tube 168 and two bores 170 and 172 through tool body 140. In alternative embodiments (not shown), a single bore or more than two bores may be used, with or without the use of separate alignment tube(s).

In operation, alignment tube 168 is first received in bore 170 as shown. In this position, tube 168 is in axial alignment with angled hole 174 at the distal end 102 of device 100. As described above, the mating semicircular steps of device 100 and sleeve 152 position angled hole 174 in its desired orientation. With this arrangement, a drill bit, screw driver, screw and/or other fastening device or tool may be inserted through the bore of tube 168 such that the device(s) are properly aligned with hole 174. The outward end of alignment tube 168 may also serve as a depth guide to stop a drill bit, screw and/or other fastener from penetrating bone 106 beyond a predetermined depth.

Alignment tube 168 may be withdrawn from bore 170 as shown, and inserted in bore 172. In this position, tube 168 aligns with hole 176 of device 100. As described above, a drill bit, screw driver, screw and/or other fastening device may be inserted through the bore of tube 168 such that the device(s) are properly aligned with hole 176.

Figure 6:
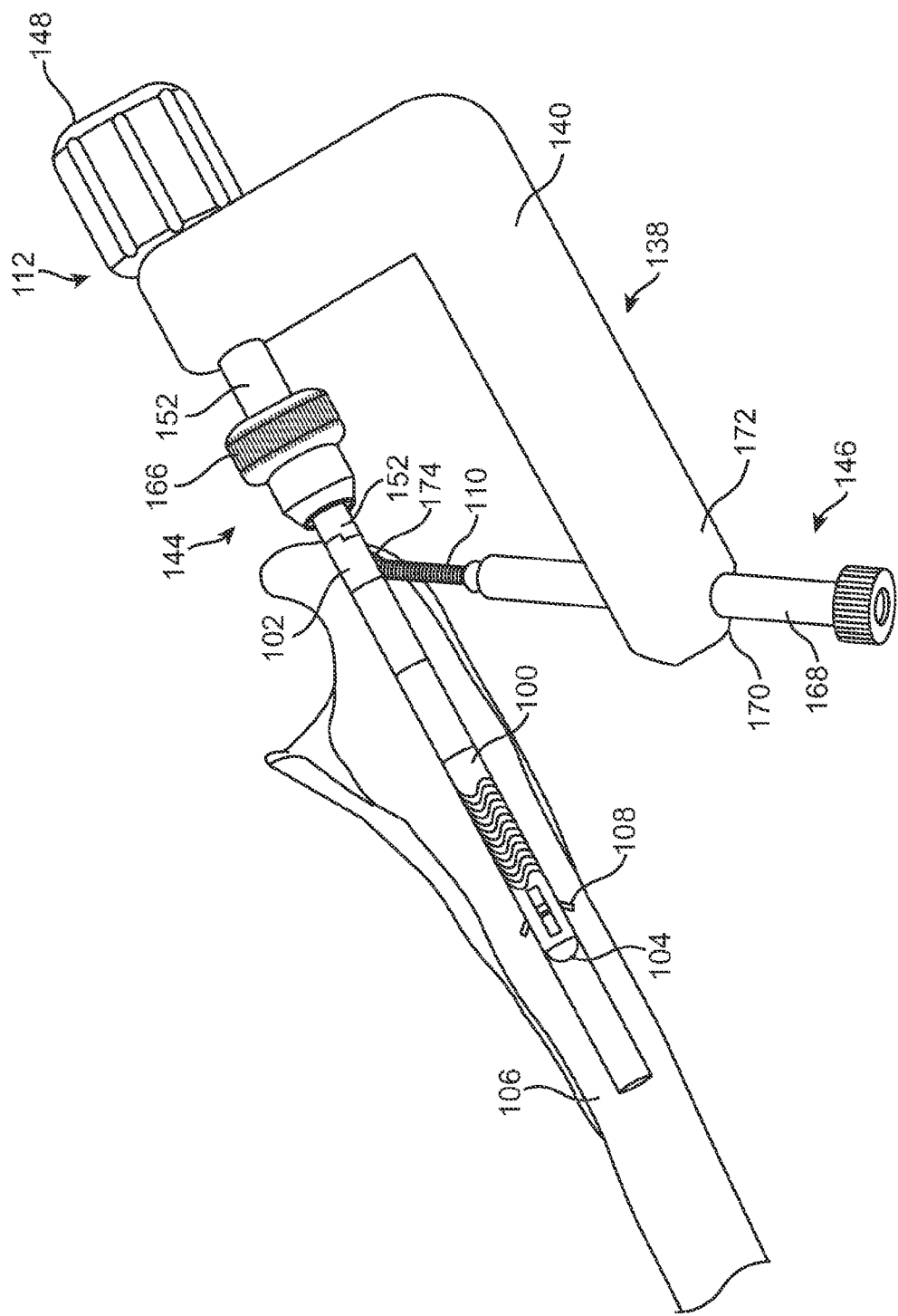
FIG. 6 is a perspective view of the tool and device shown in FIG. 4.

FIG. 6 shows alignment tube 168 of tool 138 aligning screw 110 with angled hole 174 at the distal end of device 100, as described above.

Figure 7:
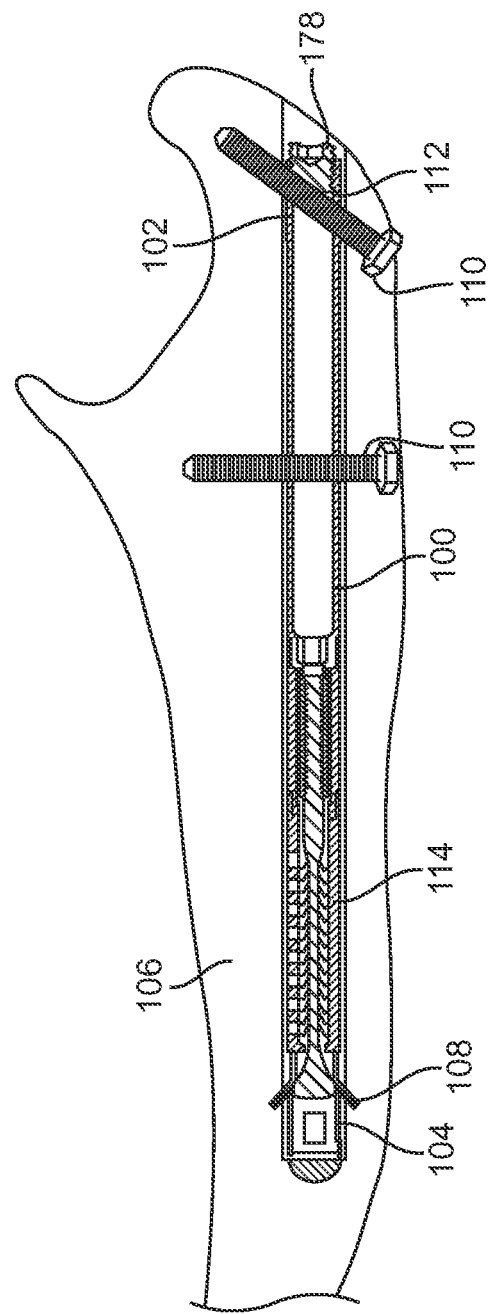
FIG. 7 is a cross-section view of the implanted device of FIG. 1.

FIG. 7 shows a first screw 110 received through angled hole 174 and a second screw 110 received through hole 176 in device 100 and into bone 106. Screws 110 may be installed manually or with the aid of tool 138 as described above. The heads of screws 110 may be configured to be self-countersinking such that they remain substantially beneath the outer surface of the bone when installed, as shown, so as to not interfere with adjacent tissue. In this embodiment, the proximal end 102 of device 100 is secured to bone 106 with two screws 110, and the distal end 104 is secured by gripper 108. In this manner, any bone fractures located between the proximal screw 110 and distal gripper 108 may be approximated and rigidly held together by device 100. In alternative embodiments (not shown), more than one gripper may be used, or only screws or other fasteners without grippers may be used to secure device 100 within bone 106. For example, the device shown in FIG. 1 could be configured with a second gripper located between screw 110 and the middle of the device if the fracture is located more at the mid-shaft of the bone. Similarly, more than two screws or other fasteners may be used, or only grippers without fasteners may be used. In various embodiments, holes such as 174 and 176 as shown and described above can be preformed in the implantable device. In other embodiments, some or all of the holes can be drilled or otherwise formed in situ after the device is implanted in the bone.

Once device 100 is secured within bone 106, combination tool 138 may be removed by turning knob 148 to disengage threads of tube 150 from threads within the proximal end 102 of device 100. An end plug 178 may be threaded into the proximal end 102 of device 100 to preventing growth of tissue into implanted device 100. Device 100 may be left in bone 106 permanently, or it may be removed by performing the above described steps in reverse. In particular, plug 178 is removed, tool 138 is attached, screws 110 are removed, gripper 108 is retracted, and device 100 is pulled out using tool 138.

Figure 8:
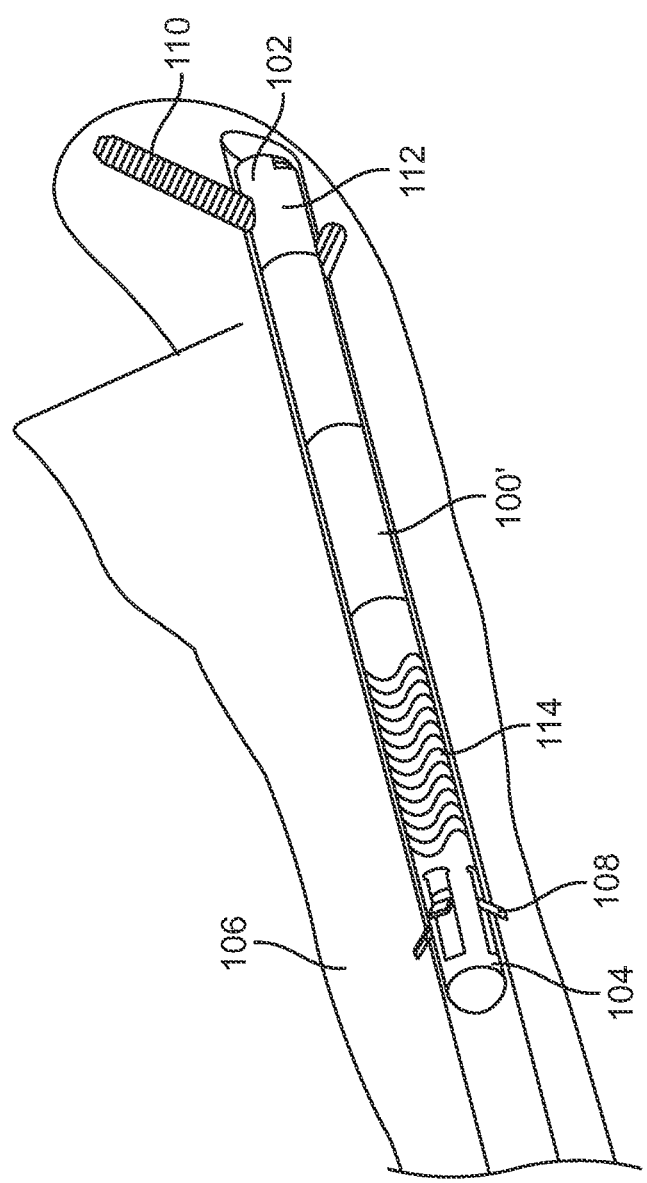
FIG. 8 is a perspective view of an alternative embodiment of the implanted device of FIG. 1.

FIGS. 8 and 9 show alternative embodiments similar to device 100 described above. Device 100' shown in FIG. 8 is essentially identical to device 100 described above but is shorter in length and utilizes a single anchor screw 110 at its proximal end 102. Device 100" shown in FIG. 9 is similar to device 100', but is shorter still. In various embodiments, the devices may be configured to have a nominal diameter of 3 mm, 4 mm, 5 mm or 6 mm. It is envisioned that all three device designs 100, 100' and 100" may each be provided in all three diameters such that the chosen device is best suited for the particular fracture(s) and anatomy in which it is implanted.

In accordance with the various embodiments of the present invention, the device may be made from a variety of materials such as metal, composite, plastic or amorphous materials, which include, but are not limited to, steel, stainless steel, cobalt chromium plated steel, titanium, nickel titanium alloy (nitinol), superelastic alloy, and polymethylmethacrylate (PMMA). The device may also include other polymeric materials that are biocompatible and provide mechanical strength, that include polymeric material with ability to carry and delivery therapeutic agents, that include bioabsorbable properties, as well as composite materials and composite materials of titanium and polyetheretherketone (PEEK™), composite materials of polymers and minerals, composite materials of polymers and glass fibers, composite materials of metal, polymer, and minerals.

Within the scope of the present invention, each of the aforementioned types of device may further be coated with proteins from synthetic or animal source, or include collagen coated structures, and radioactive or brachytherapy materials. Furthermore, the construction of the supporting framework or device may include radio-opaque markers or components that assist in their location during and after placement in the bone or other region of the musculo-skeletal systems.

Further, the reinforcement device may, in one embodiment, be osteo incorporating, such that the reinforcement device may be integrated into the bone. In a further embodiment, there is provided a low weight to volume device deployed in conjunction with other suitable materials to form a composite structure in-situ. Examples of such suitable materials may include, but are not limited to, bone cement, high density polyethylene, Kapton®, polyetheretherketone(PEEK™), and other engineering polymers.

Once deployed, the device may be electrically, thermally, or mechanically passive or active at the deployed site within the body. Thus, for example, where the device includes nitinol, the shape of the device may be dynamically modified using thermal, electrical or mechanical manipulation. For example, the nitinol device may be expanded or contracted once deployed, to move the bone or other region of the musculo-skeletal system or area of the anatomy by using one or more of thermal, electrical or mechanical approaches.

It is contemplated that the inventive implantable device, tools and methods may be used in many locations within the body. Where the proximal end of a device in the anatomical context is the end closest to the body midline and the distal end in the anatomical context is the end further from the body midline, for example, on the humerus, at the head of the humerus (located proximal, or nearest the midline of the body) or at the lateral or medial epicondyle (located distal, or furthest away from the midline); on the radius, at the head of the radius (proximal) or the radial styloid process (distal); on the ulna, at the head of the ulna (proximal) or the ulnar styloid process (distal); for the femur, at the greater trochanter (proximal) or the lateral epicondyle or medial epicondyle (distal); for the tibia, at the medial condyle (proximal) or the medial malleolus (distal); for the fibula, at the neck of the fibula (proximal) or the lateral malleoulus (distal); the ribs; the clavicle; the phalanges; the bones of the metacarpus; the bones of the carpus; the bones of themetatarsus; the bones of the tarsus; the sternum and other bones, the device may be adapted and configured with adequate internal dimension to accommodate mechanical fixation of the target bone and to fit within the anatomical constraints. As will be appreciated by those skilled in the art, access locations other than the ones described herein may also be suitable depending upon the location and nature of the fracture and the repair to be achieved. Additionally, the devices taught herein are not limited to use on the long bones listed above, but can also be used in other areas of the body as well, without departing from the scope of the invention. It is within the scope of the invention to adapt the device for use in flat bones as well as long bones.

Figure 10A:
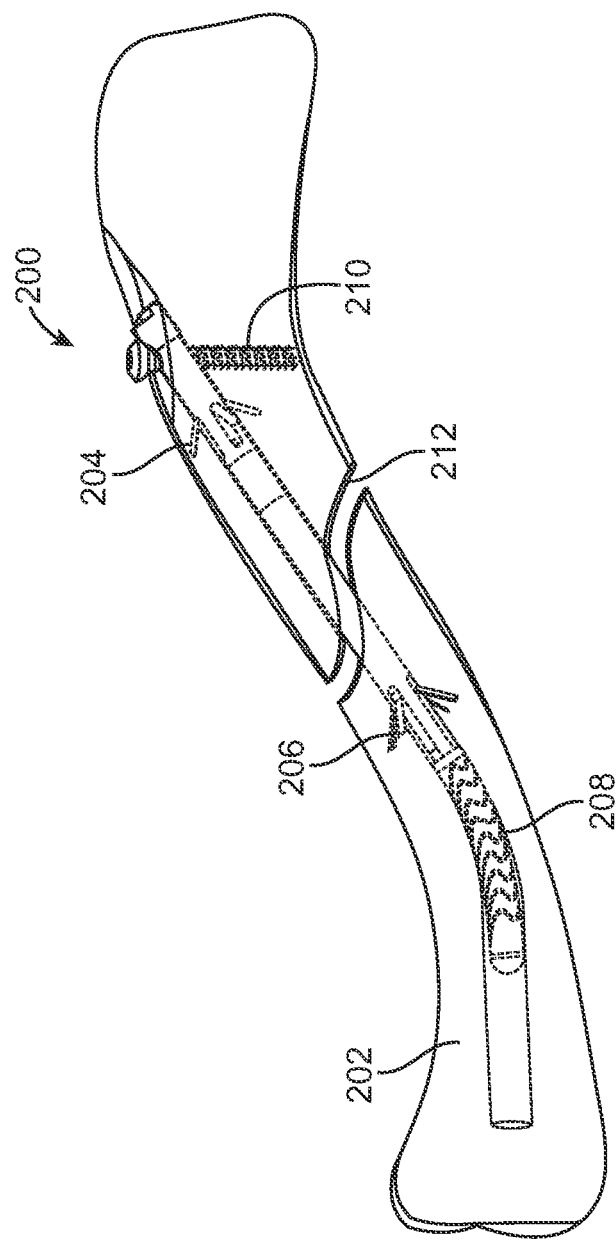
FIG. 10A is a perspective view of another embodiment of a bone fixation device shown deployed in a fractured clavicle.

FIGS. 10A-10I show another embodiment of a bone fixation device constructed according to aspects of the invention. FIG. 10A is a perspective view showing the exemplary device 200 deployed in a fractured clavicle 202. Device 200 is similar to device 100 described above and shown in FIGS. 1-7, but has a gripper 204 located near its proximal end, another gripper 206 located at a more distal location, and a flexible-to-rigid body portion 208 located near the distal end of the device. A bone screw 210 and gripper 204 are configured to secure device 200 inside bone 202 on the proximal side of fracture 212, while gripper 206 and flexible-to-rigid body portion 208 are configured to secure device 200 on the distal side of fracture 212. In other respects, construction and operation of device 200 is much like that of device 100 described above.

Figure 10B:
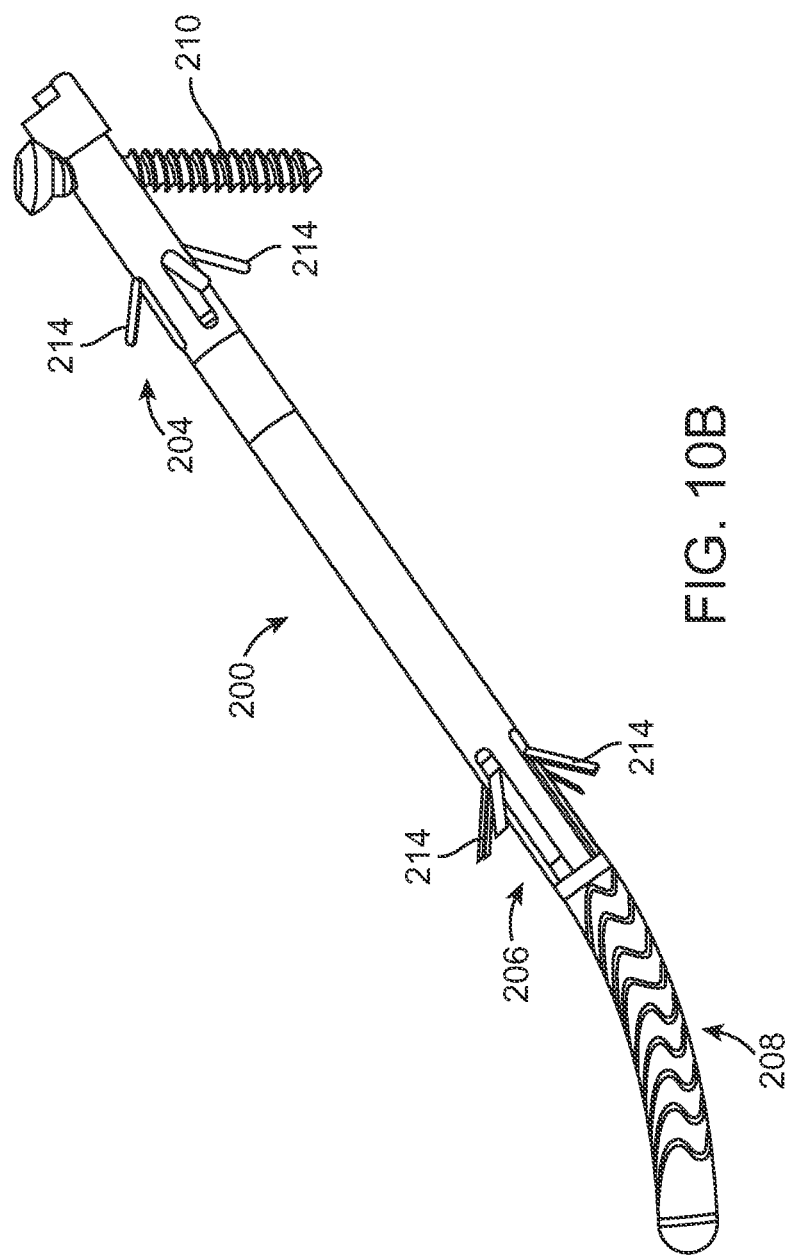
FIG. 10B is perspective view of the device shown in FIG. 10A shown in a deployed state.
Figure 10C:
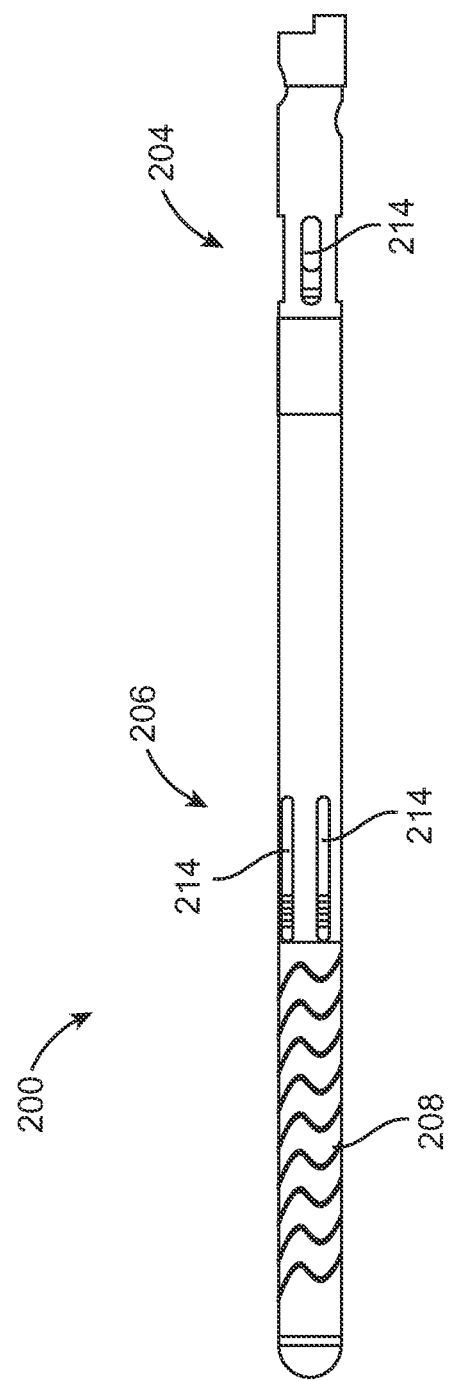
FIG. 10C is a side elevation view of the device shown in FIG. 10A shown in a retracted or undeployed state.
Figure 10D:
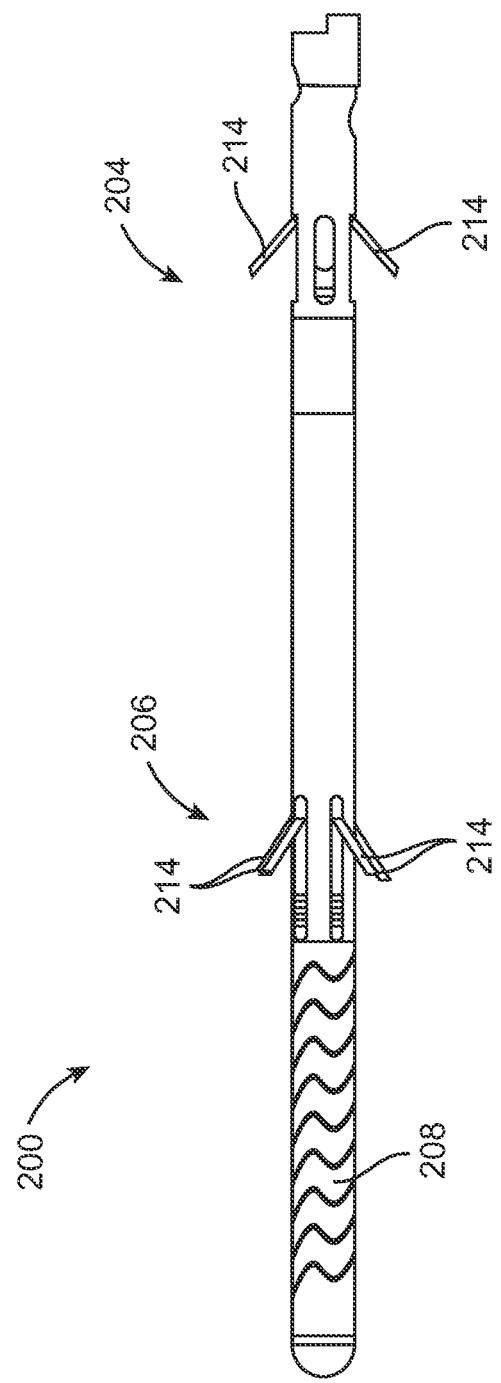
FIG. 10D is a side elevation view of the device shown in FIG. 10A shown in a deployed state.
Figure 10E:
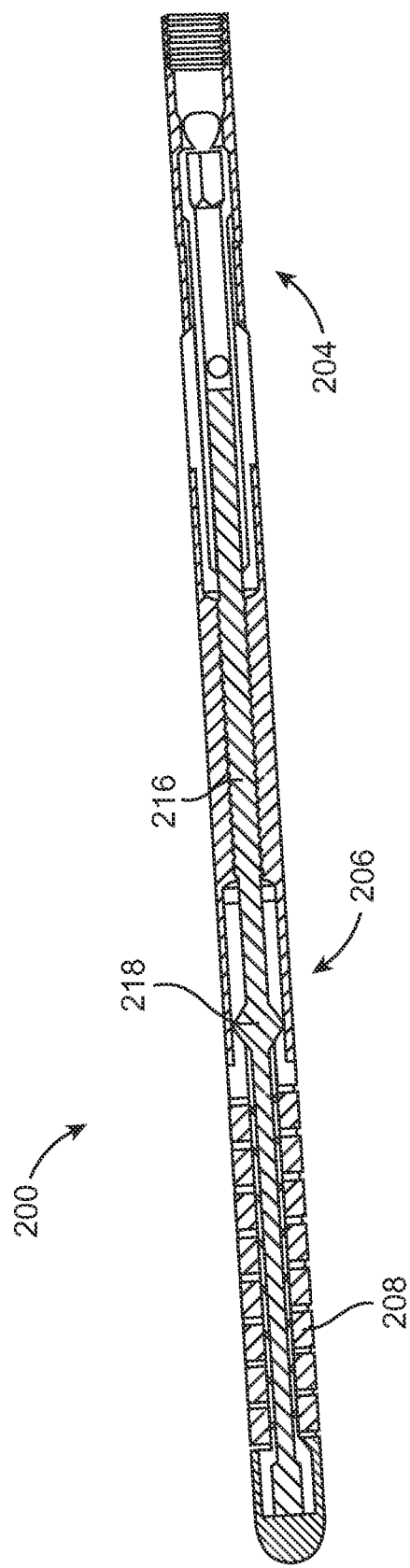
FIG. 10E is a cross-sectional view of the device shown in FIG. 10A shown in a retracted or undeployed state.
Figure 10F:
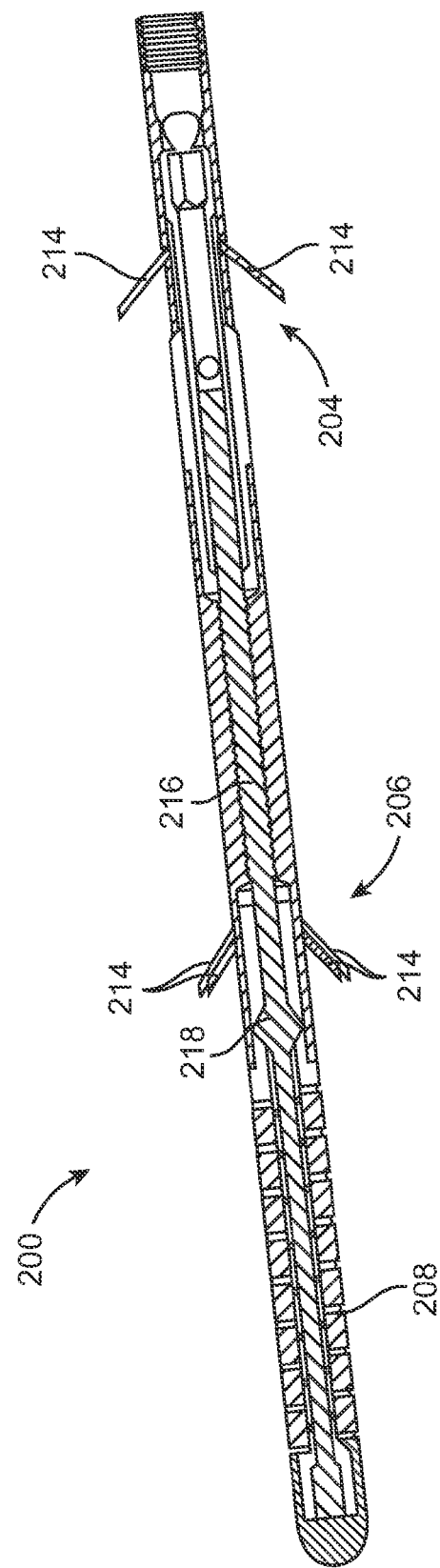
FIG. 10F is a cross-sectional view of the device shown in FIG. 10A shown in a deployed state.

In this exemplary embodiment, each of the two grippers 204 and 206 has four outwardly expanding arms 214. These arms are spaced at 90 degree intervals around the circumference of the device body. The arms 214 of gripper 204 may be offset by 45 degrees from arms 214 of gripper 206 as shown in the figures to distribute the forces applied by grippers 204 and 206 on the bone 202. As shown in FIGS. 10E and 10F, a single actuator 216 may be used to deploy both grippers 204 and 206. Actuator 216 may also be used to axially compress flexible-to-rigid body portion 208 to make it substantially rigid. At least a portion of actuator 216 may be flexible to allow flexible-to-rigid body portion 208 to assume a curved shape, as best seen in FIGS. 10A and 10B. Alternatively, it may be desirable in some embodiments to have flexible-to-rigid body portion 208 maintain a straight or a curved configuration regardless of whether it is in a flexible or rigid state. In these embodiments, the actuator may be rigid and faulted with the desired straight and/or curved shape to match the flexible-to-rigid body portion. In some embodiments, it may also be desirable to design at least a portion of the actuator with a high degree of axial elasticity to allow the actuator to continue to expand some gripper(s) and/or compress some flexible-to-rigid body portion(s) after other gripper(s) and/or flexible-to-rigid body portion(s) have already been fully deployed.

Figure 10G:
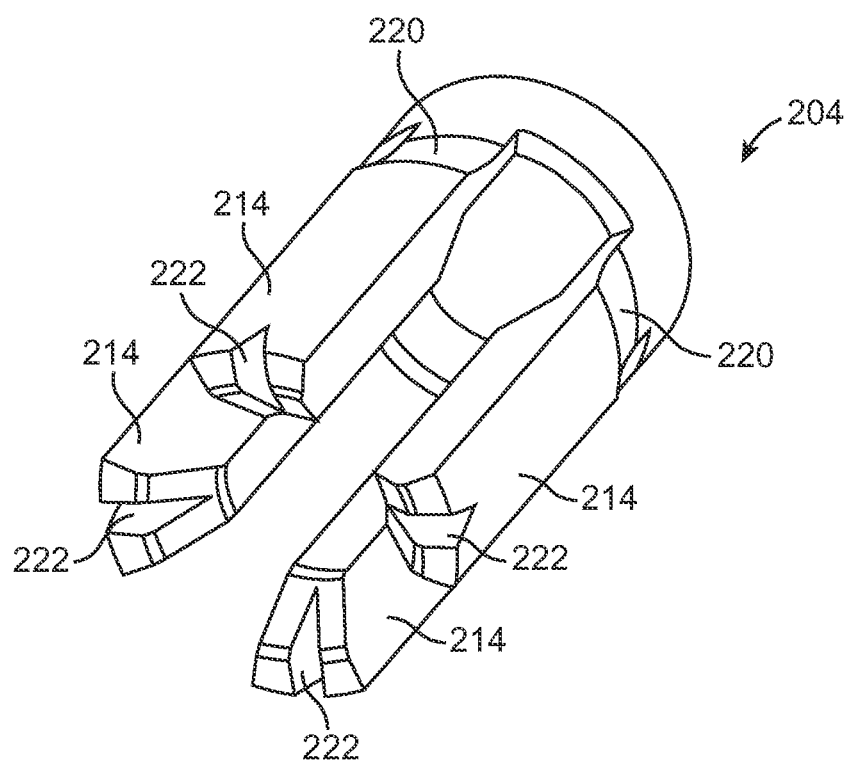
FIG. 10G is a perspective view of a gripper of the device shown in FIG. 10A shown in a retracted or undeployed state.
Figure 10H:
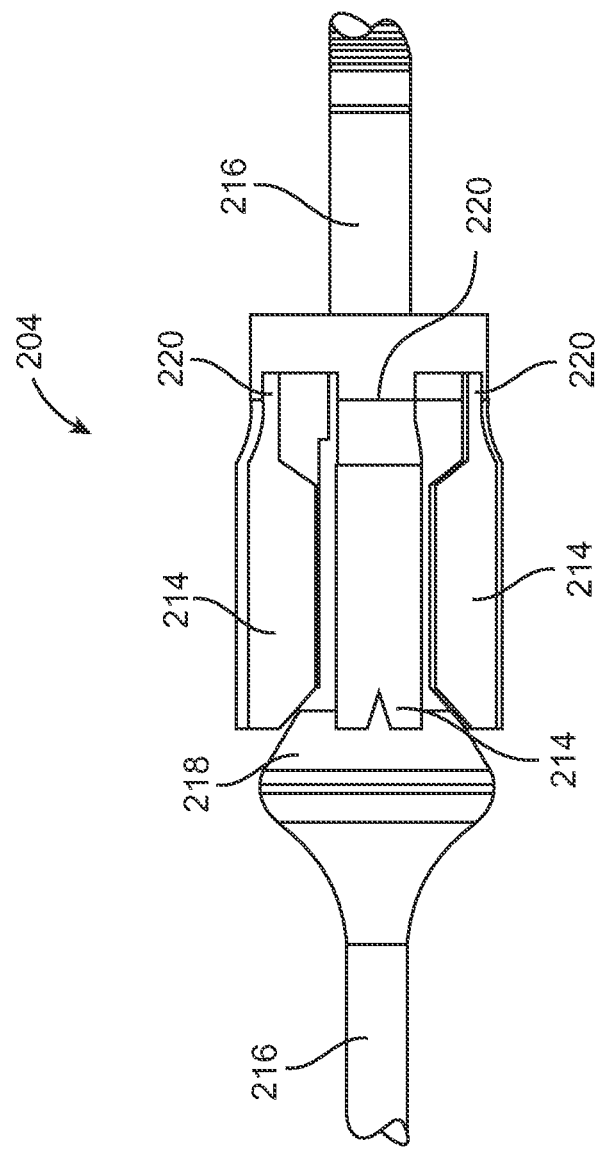
FIG. 10H is a side elevation view of a gripper and actuator of the device shown in FIG. 10A shown in a retracted or undeployed state.
Figure 10I:
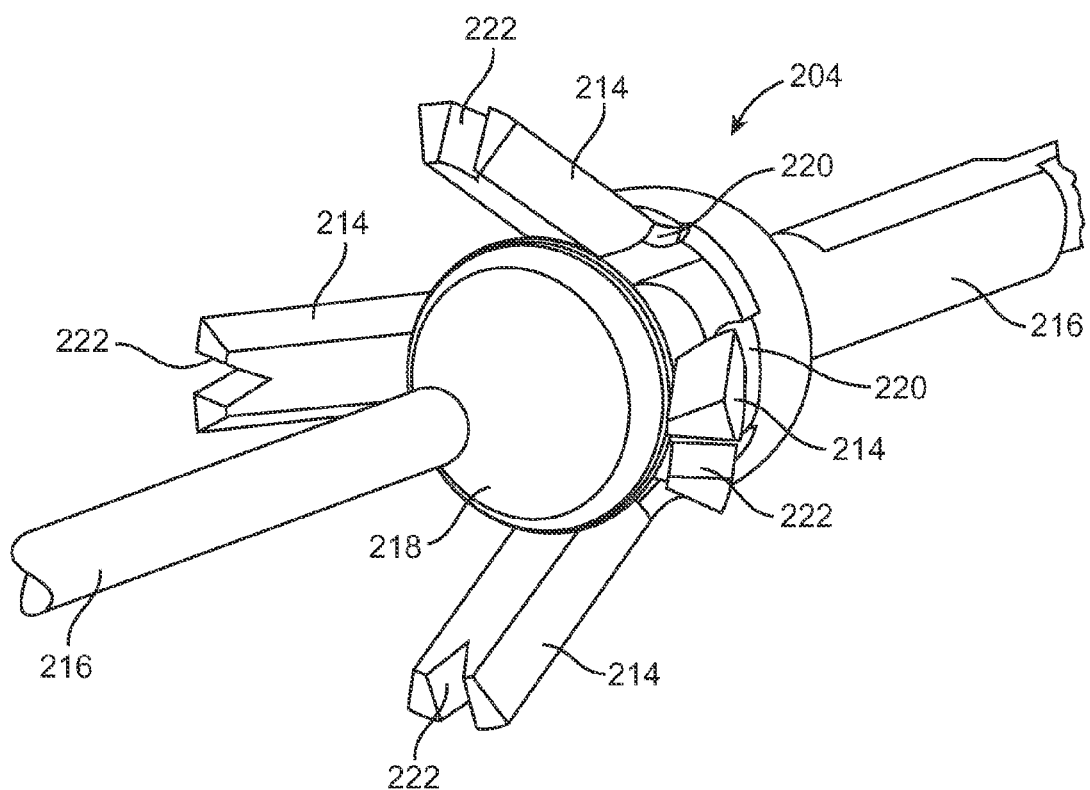
FIG. 10I is a perspective view of a gripper and actuator of the device shown in FIG. 10A shown in a deployed state.

Referring to FIGS. 10G-10I, further details of an exemplary gripper 204 are shown. FIGS. 10G and 10H show gripper 204 with bendable arms 214 in a retracted state. As cam 218 of actuator 216 is driven axially into the distal ramped ends of arms 214, arms 214 bend at thinned portions 220 to move radially outward toward the deployed position shown in FIG. 10I. Notches 222 may be provided in the distal ends of arms 214 as shown to allow arms 214 to better grip interior bone surfaces. Without departing from the scope of the invention, one, two, three, or more bendable arms may be used.

Figure 11B:
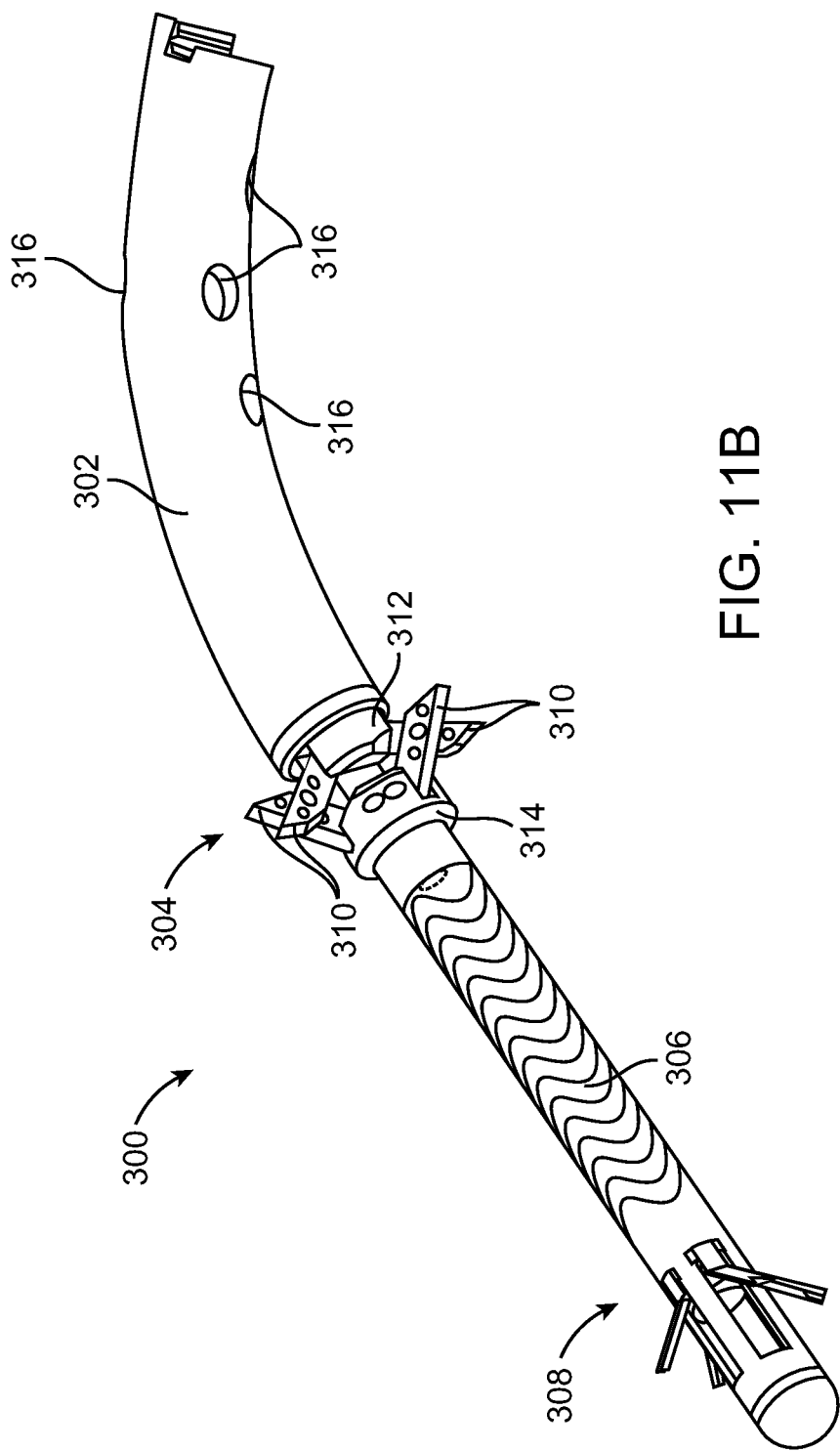
FIG. 11B is perspective view of the device shown in FIG. 11A shown in a deployed state.
Figure 11C:
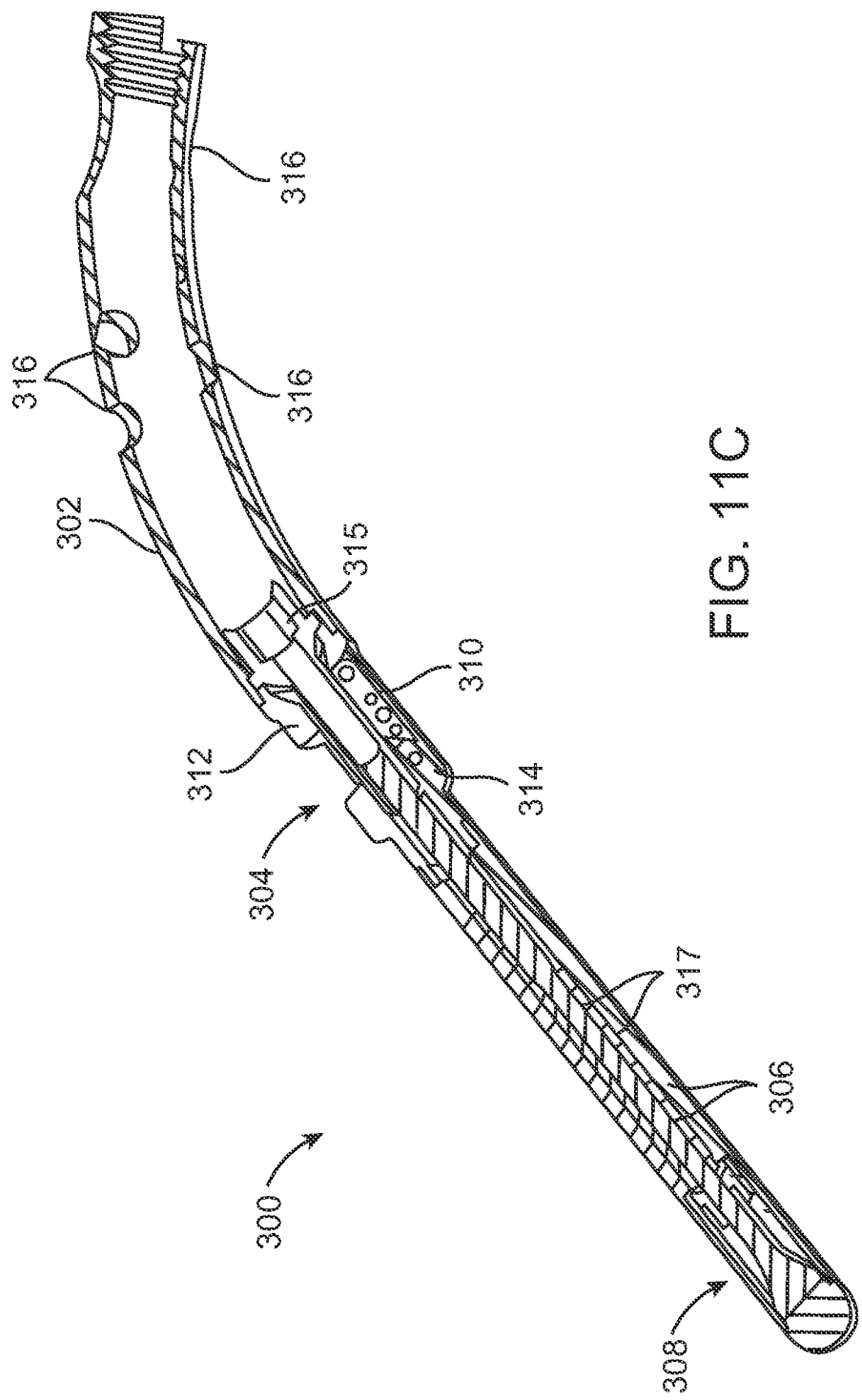
FIG. 11C is a cross-sectional view of the device shown in FIG. 11A shown in a retracted or undeployed state.
Figure 11D:
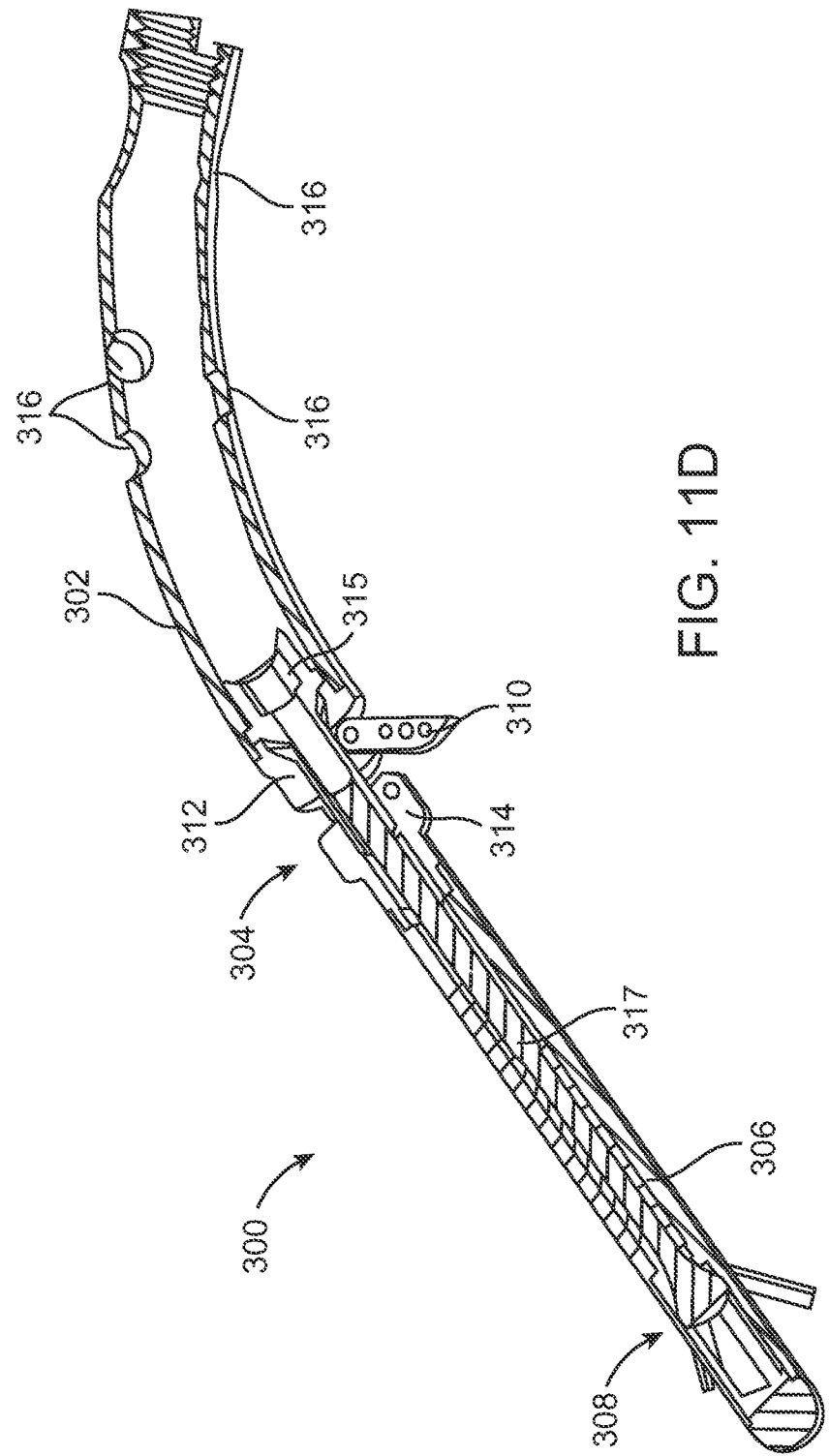
FIG. 11D is a cross-sectional view of the device shown in FIG. 11A shown in a deployed state.

Referring to FIGS. 11A-11D, another embodiment of a bone fixation device is shown. Device 300 includes a curved hub 302, proximal gripper 304, flexible-to-rigid body portion 306, and distal gripper 308. Distal gripper 308 is similar in construction and operation to grippers 204 and 206 described above. Proximal gripper 304 is provided with three pairs of scissor arms 310. Each pair of arms 310 is pivotably interconnected at a mid-portion by a pin. Each arm is pivotably connected with a pin to either proximal end piece 312 or distal end piece 314. When end pieces 312 and 314 are moved closer together, arms 310 pivot radially outward from an axially aligned retracted position, as shown in FIGS. 11A and 11C, to a deployed position, as shown in FIGS. 11B and 11D. In the deployed position, the distal ends of the six arms 310 engage an inner surface of a bone as previously described.

In operation, device 300, with grippers 304 and 308 in a retracted state, may be inserted into the intramedullary space within a bone, such as the radius. Device 300 may be inserted through a curved opening formed in the bone, such as an opening formed through a bony protuberance on a distal or proximal end or through the midshaft of the bone. Curved hub 302 may be configured with the same geometry of the curved opening in the bone, and when the flexible-to-rigid body portion 306 is in its flexible state, it can assume this same geometry. Once device 300 is in place inside the bone, actuator 315 (shown in FIGS. 11C and 11D) may be actuated from the proximal end of device 300 by turning drive member 317 in a manner similar to that previously described. Longitudinal movement of actuator 315 toward the proximal end of device 300 causes flexible-to-rigid body portion 306 to foreshorten and assume its rigid state, and causes grippers 304 and 308 to outwardly deploy against the bone. Bone screws may be inserted through holes 316 shown in curved hub 302 to secure the proximal end of device 300 to the bone. Further details of the construction and operation of a device similar to device 300 may be found in co-pending U.S. application Ser. No. 11/944,366 filed Nov. 21, 2007 and entitled Fracture Fixation Device, Tools and Methods.

Device 300 is an example of an embodiment utilizing mixed gripper types. In other words, this device uses one scissors-arm tripod gripper 304 and one bendable-arm gripper 308. Other embodiments of the invention (not shown) use various combinations of gripper(s) and/or flexible-to-rigid body portion(s). Further exemplary gripper embodiments are described in detail in co-pending U.S. application Ser. No. 61/100,652 filed Sep. 26, 2008 and entitled Fracture Fixation Device, Tools and Methods. It is envisioned that virtually any combination of zero, one, two, or more grippers may be used in combination with zero, one, two or more flexible-to-rigid body portions to form a device adapted to a particular bone anatomy, fracture, disease state or fixation purpose. The grippers and/or flexible-to-rigid body portions may each be of identical or different construction, and may be placed together or at other locations along the device. Further, a straight, curved, flexible, rigid, or no hub at all may be used with the above combinations. Additionally, screws, K-wires, sutures or no additional fixation may be used with these various devices. The devices may be specially designed and constructed for a particular purpose or range of purposes. According to aspects of the invention, the components may also be designed to be interchangeable and/or produced in various sizes so that surgical kits may be provided. Such kits would allow surgical teams to select from a variety of components to build devices themselves, each suited to a particular patient's unique situation.

Referring to FIGS. 12A through 20B, further examples of the hubs discussed above are shown and will now be described.

FIGS. 12A-12F show details of a curved hub 400 similar to hub 302 illustrated in FIGS. 11A-11D. In this embodiment, hub 400 has an internally threaded portion at its proximal end 402 for engaging with an insertion and removal tool as described above. (The proximal end is referenced as the end closest to the surgeon.) The proximal end 402 may also have a keyed feature for mating with the tool for maintaining a desired orientation of hub 400 relative to the tool. Hub 400 may also be provided with a counterbore at its distal end 404 for coupling to a gripper or flexible-to-rigid body portion, such as by press fit and/or welding.

Figure 12A:
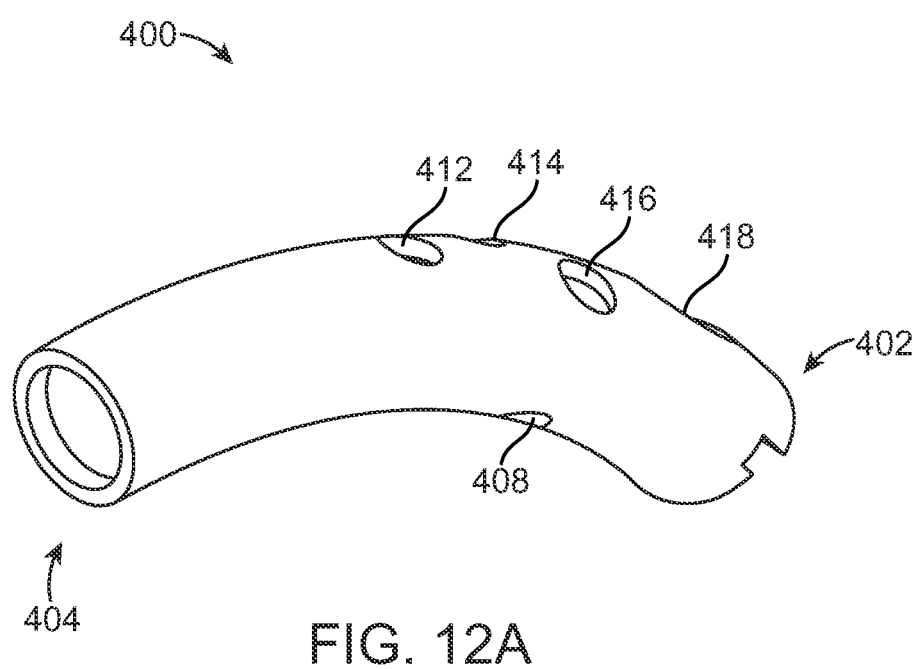
FIGS. 12A-12F show various views of an exemplary embodiment of a bone fixation device hub.
Figure 12B:
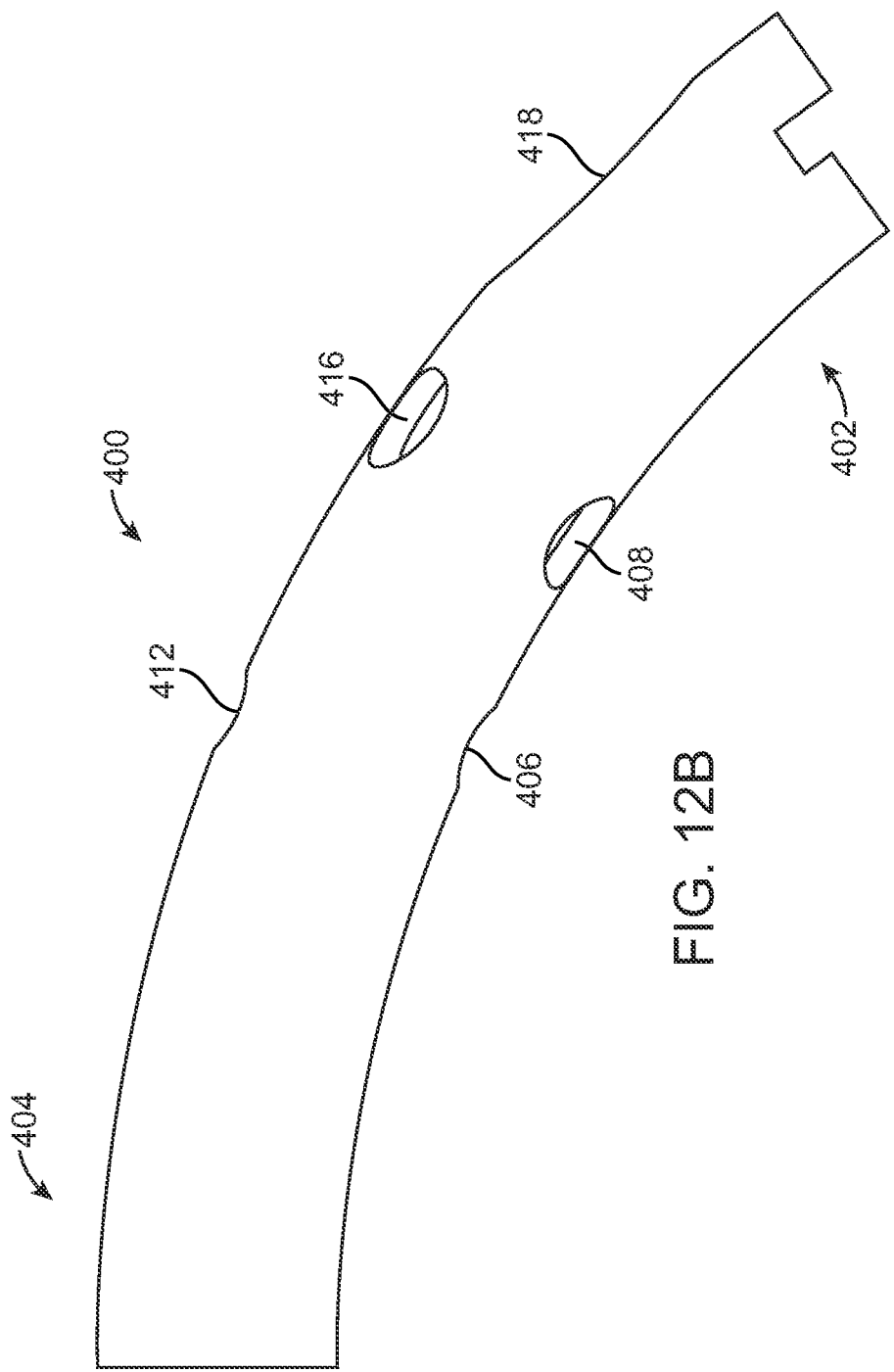
Figure 12C:
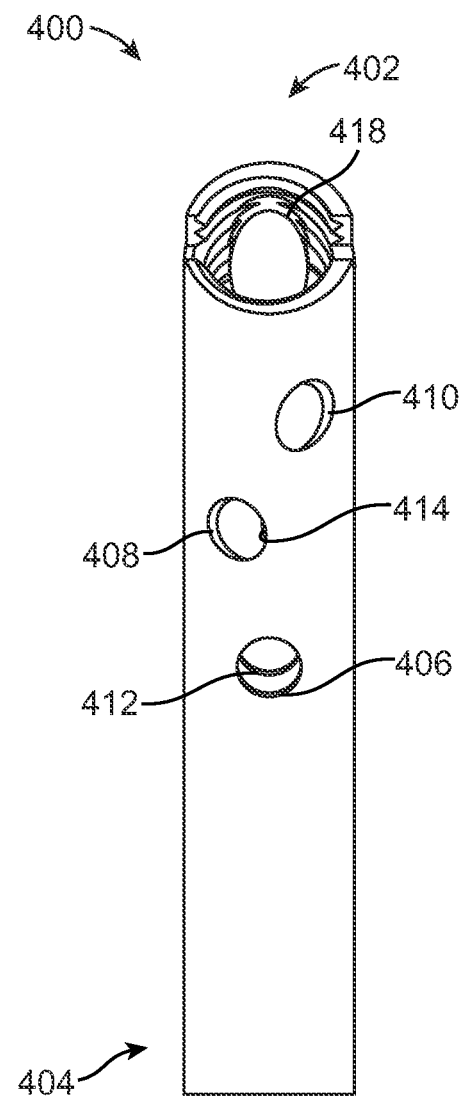
Figure 12D:
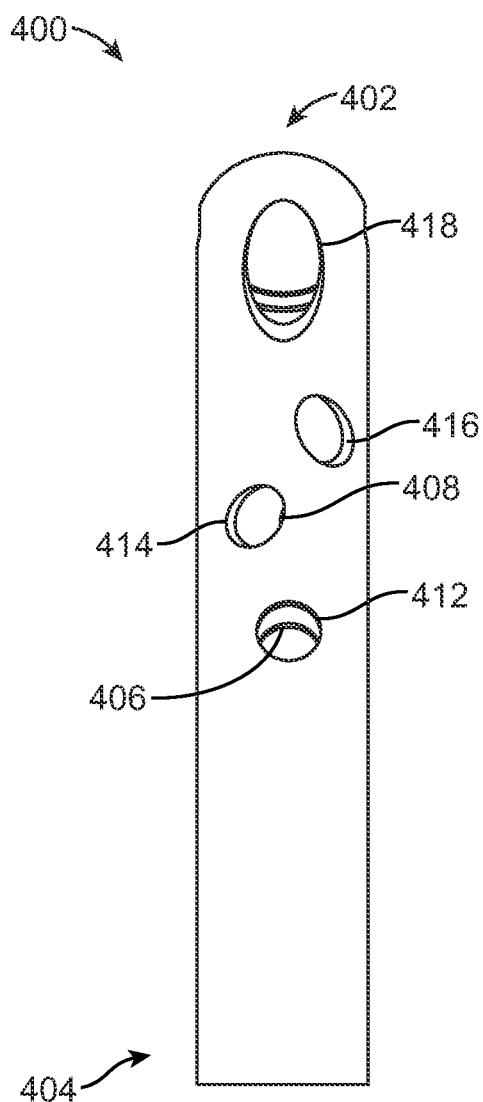
Figure 12E:
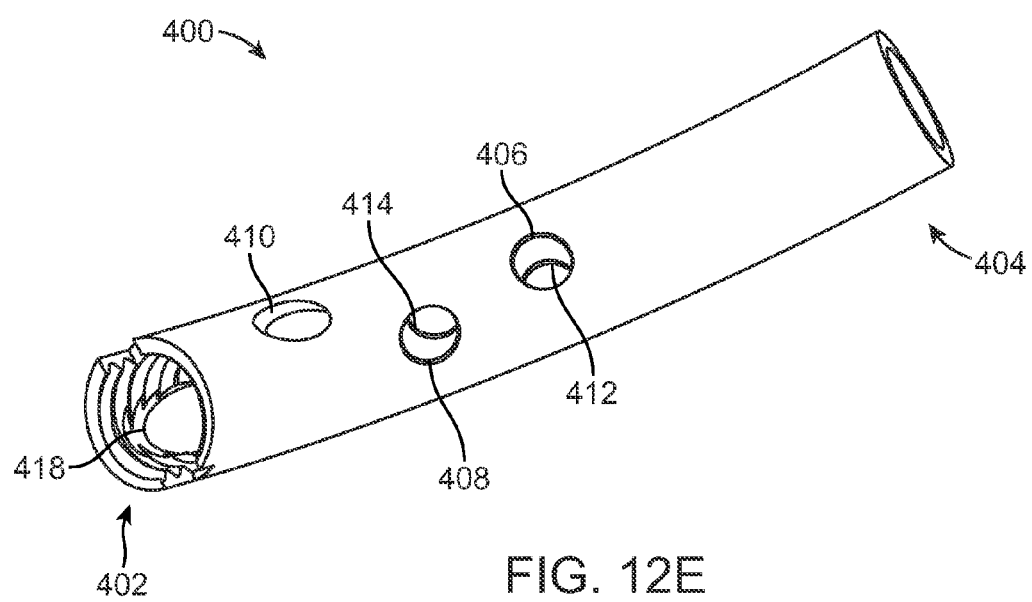
Figure 12F:
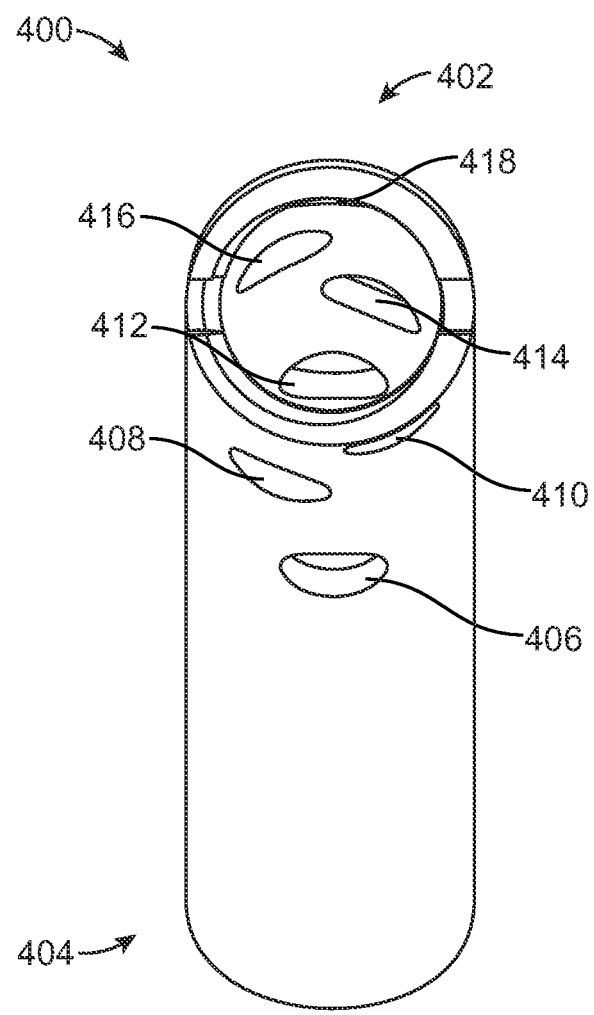

Exemplary hub 400 includes three holes 406, 408 and 410 through the wall thickness on its concave side, as best seen in FIG. 12C. Similarly, hub 400 includes four holes 412, 414, 416, and 418 through the wall thickness on its convex side, as best seen in FIG. 12D. At least a portion of all seven holes may be seen in FIG. 12F. Holes 406 and 412 on opposite sides of hub 400 are aligned to allow a bone screw to be inserted through the two holes across the hub to secure hub 400 to the bone and/or to secure bone fragment(s) with the screw. Similarly, holes 408 and 414 are aligned to receive a second bone screw, and holes 410 and 416 are aligned to receive a third bone screw. A fourth screw may be inserted through the open proximal end 402 of hub 400 and out through hole 418. Each screw may be passed first through cortical bone, then cancellous bone, then through the two holes of hub 400, through more cancellous bone and possibly into more cortical bone on the opposite side of the bone from where the screw entered.

In this embodiment, the holes of hub 400 have a diameter of 2.4 mm. In other embodiments, the holes have a diameter of 2.7 mm. In still other embodiments, the holes may have larger or smaller diameters. The holes may be threaded during the fabrication of hub 400, or threads may be formed in vivo. Various fixtures, jigs, tools and methods may be used to align the screws with the holes, such as a tool similar to tool 138 shown in FIGS. 4-6 and described above. Further examples of positioning aids are provided in copending U.S. application Ser. No. 11/944,366 filed Nov. 21, 2007 and entitled Fracture Fixation Device, Tools and Methods. The heads of the screws may be countersunk into the bone as described in copending U.S. application Ser. No. 61/117,901 filed Nov. 25, 2008 and entitled Bone Fracture Fixation Screws, Systems and Methods of Use.

Figure 12G:
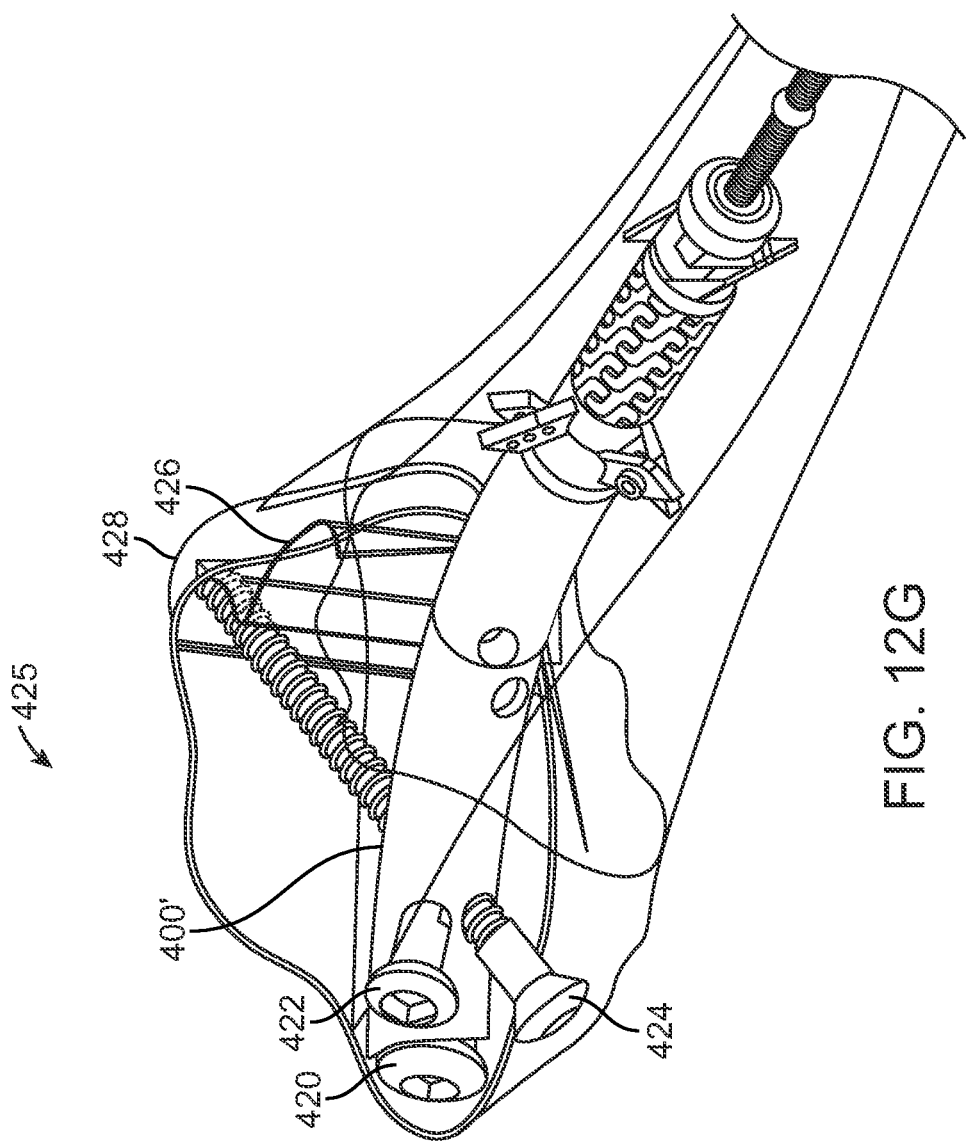
FIGS. 12G-12I show various views of an exemplary embodiment of a bone fixation device implanted in a bone.
Figure 12H:
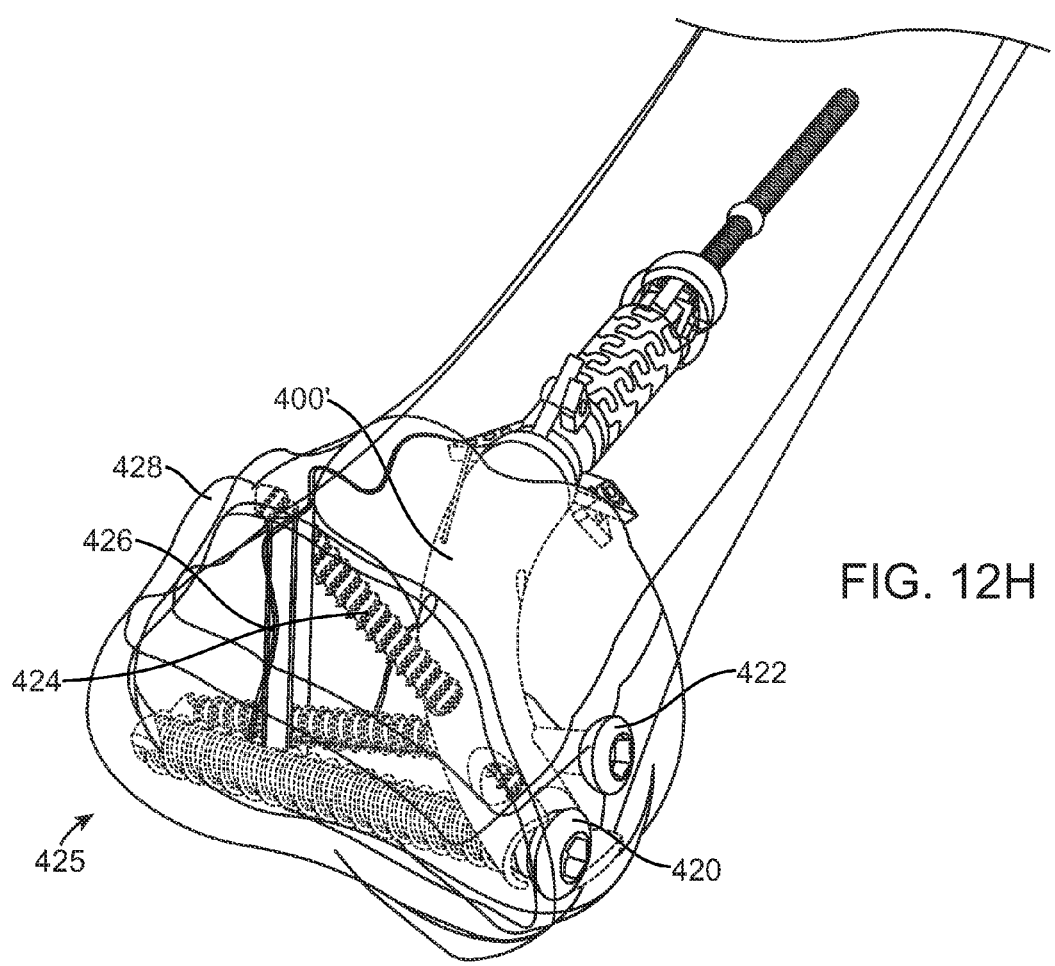
Figure 12I:
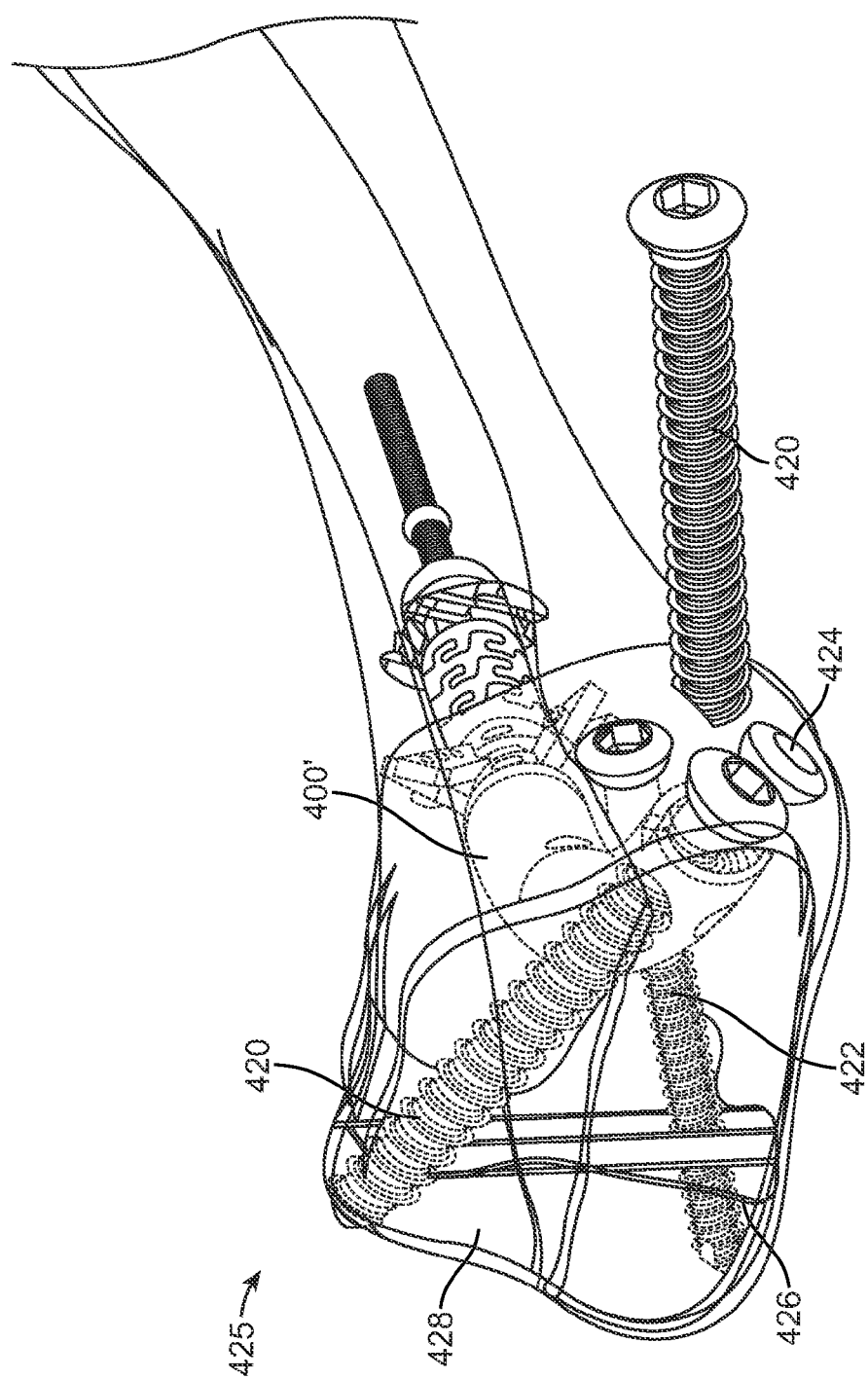

FIGS. 12G-12I illustrate an example how bone screws 420, 422, 424 may be inserted through hub 400' (which is similar to hub 400) as described above to secure the comminuted fracture depicted at the distal end of a radius bone 425. One, two, three, four, or more screws may be used depending on the anatomy and fracture condition of each particular case. It should be noted that in this particular embodiment, either screw 422 or 424 may be placed through hub 400', but not both at the same time, as their paths intersect inside hub 400'. It can be seen that screws 422 and 424 extend across fracture 426 into bone fragment 428. Accordingly, either screw 422 or 424 may be used to approximate fracture 426 when the screw is tightened.

Figure 13A:
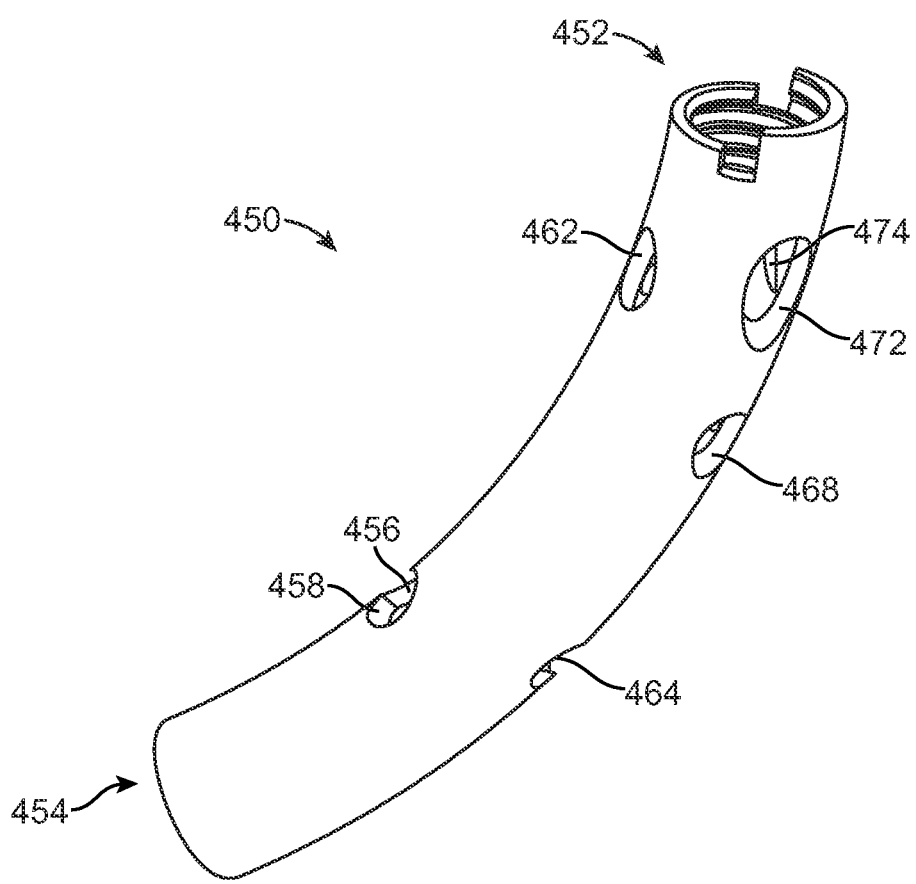
FIGS. 13A-13E show various views of another exemplary embodiment of a bone fixation device hub.
Figure 13B:
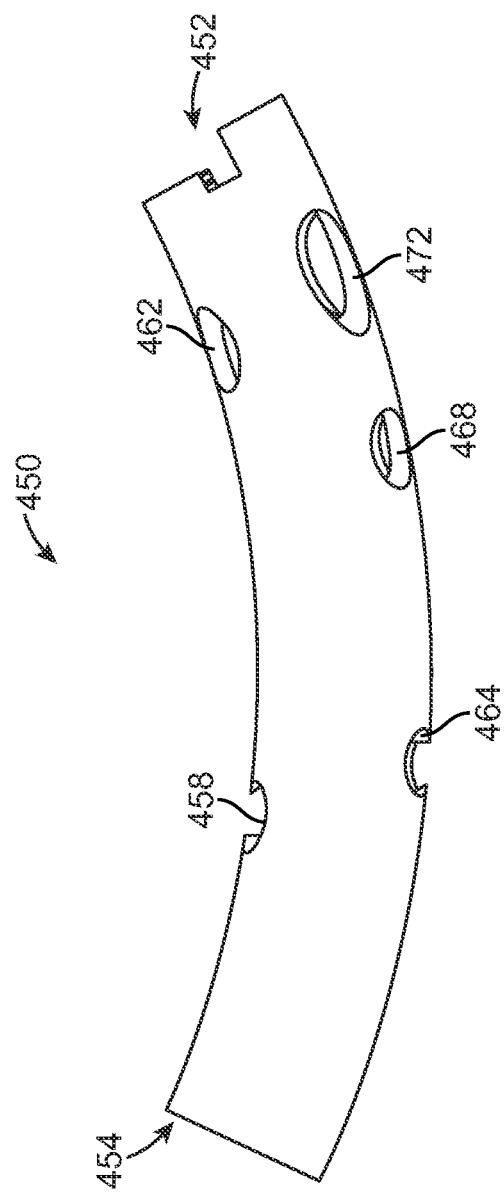
Figure 13C:
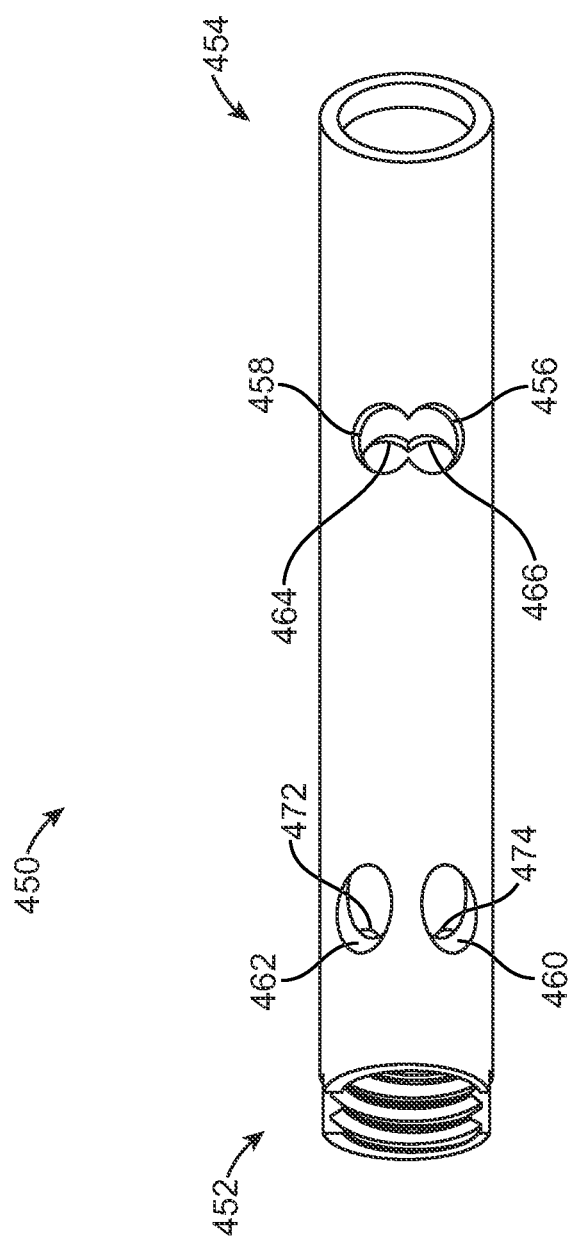

FIGS. 13A-13E show another exemplary embodiment of a bone fixation device hub 450. Hub 450 is of similar construction to hub 400 described above and includes proximal end 452 and distal end 454. As best seen in FIG. 13C, hub 450 includes four holes 456, 458, 460, and 462 through the wall thickness on its concave side. Holes 456 and 458 are located the same longitudinal distance from distal end 454, but are symmetrically located on opposite sides of a central longitudinal plane. As can be seen, holes 456 and 458 actually overlap to form a single, figure-eight shaped hole. Holes 460 and 462 are also located the same longitudinal distance from proximal end 452, and are symmetrically located on opposite sides of a central longitudinal plane.

Figure 13D:
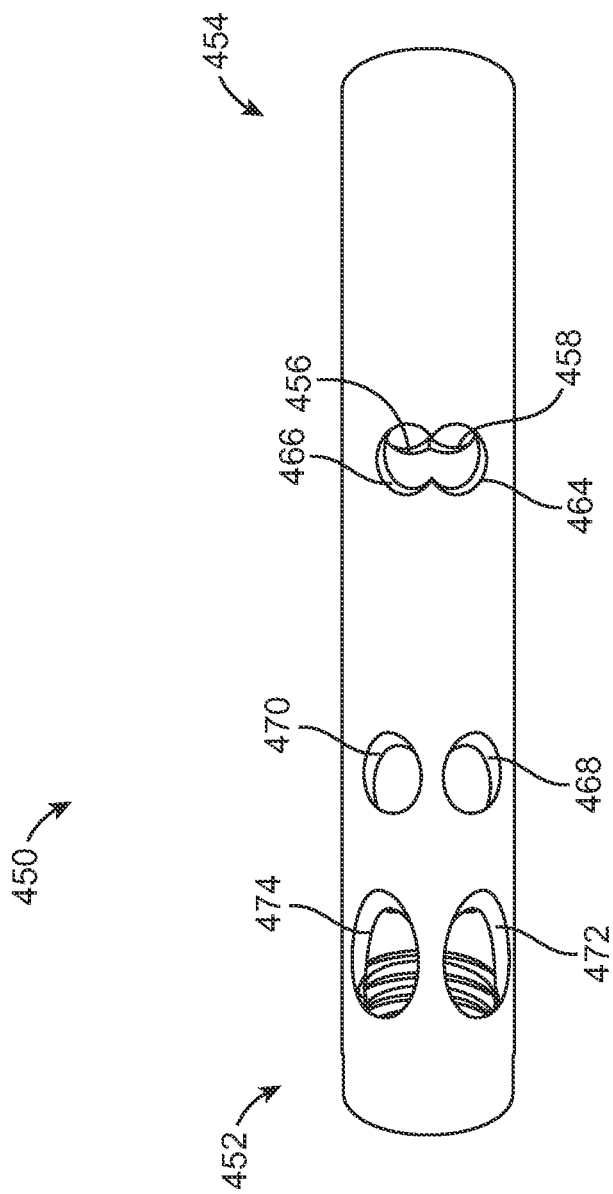
Figure 13E:
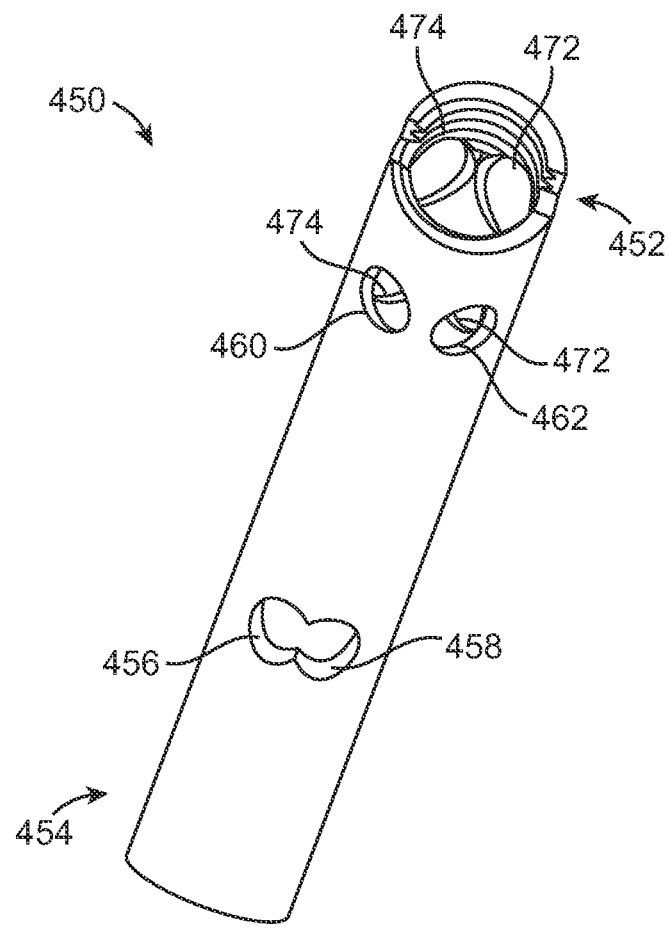

As best seen in FIG. 13D, hub 450 also includes six holes 464, 466, 468, 470, 472, and 474 through the wall thickness on its convex side. Holes 464 and 466 are located the same longitudinal distance from distal end 454, but are symmetrically located on opposite sides of a central longitudinal plane. Holes 464 and 466 also overlap to form a single, figure-eight shaped hole, similar to holes 456 and 458 described above. Holes 468 and 470 are also located the same longitudinal distance from proximal end 452, and are symmetrically located on opposite sides of a central longitudinal plane. Similarly, holes 472 and 474 are also located the same longitudinal distance from proximal end 452, and are symmetrically located on opposite sides of a central longitudinal plane.

Holes 456 and 464 on diagonally opposite sides of hub 450 are aligned to allow a bone screw to be inserted through the two holes across the hub, passing through a centerline of hub 450. Similarly, holes 458 and 466 on diagonally opposite sides of hub 450 are aligned to allow a bone screw to be inserted through the two holes across the hub, passing through a centerline of hub 450. Since both of these two screw paths cross the centerline at the same location forming an X-pattern, only one screw may be placed through these two pairs of holes 456/464 and 458/466 in any particular procedure.

In a similar manner, holes 460 and 468 on diagonally opposite sides of hub 450 are aligned to allow a bone screw to be inserted through the two holes across the hub, passing through a centerline of hub 450. Holes 462 and 470 on diagonally opposite sides of hub 450 are also aligned to allow a bone screw to be inserted through the two holes across the hub, passing through a centerline of hub 450. Since both of these two screw paths cross the centerline at the same location forming an X-pattern, only one screw may be placed through these two pairs of holes 460/468 and 462/470 in any particular procedure.

A third screw may be inserted through the open proximal end 452 of hub 450 and out through either hole 472 or hole 474. Since these two screw paths also overlap, only one screw may be placed though them at a time.

As can be appreciated from FIGS. 13A-13E and the description above, exemplary hub 450 is symmetrical about a central plane. Since hub 450 may receive up to three screws, each in one of two positions, there are a total of eight screw patterns that may be used with hub 450, depending on the situation. Additionally, only one or two screws, or no screws, may be used in a particular procedure, if desired. The positions and orientations of the screw holes of hub 450 relative to previously described hub 400 may take better advantage of cortical bone locations in some procedures for better anchoring of bone screws. In particular, a screw passing through hole pairs 456/464, 458/466, 460/468 or 462/470 of hub 450 will have a reduced angle relative to a longitudinal axis of a bone as compared with the screw trajectories of similar screws in hub 400. Similarly, a screw passing through either hole 472 or 474 will have a different angle from the same screw in hub 400, which in many cases allows the screw of hub 450 to hit harder bone. Additionally, screw paths of hole pairs 460/468 and 462/470 are closer to the proximal end of hub 450 than similar screw paths in hub 400, allowing the screws to fixate in harder bone located near the end of a bone. All of the new screw trajectories provided by hub 450 may be used with the in vivo hole forming hubs that will be later described below. The trajectories of hole pairs 456/464, 458/466, 460/468 or 462/470 also form an angle with a central, longitudinal plane containing the curve of hub 450 (in other words, a plane of symmetry of the hole pairs.) In some embodiments, the hole pairs each form an angle with the plane falling in a range of about 5 to 30 degrees.

Figure 14A:
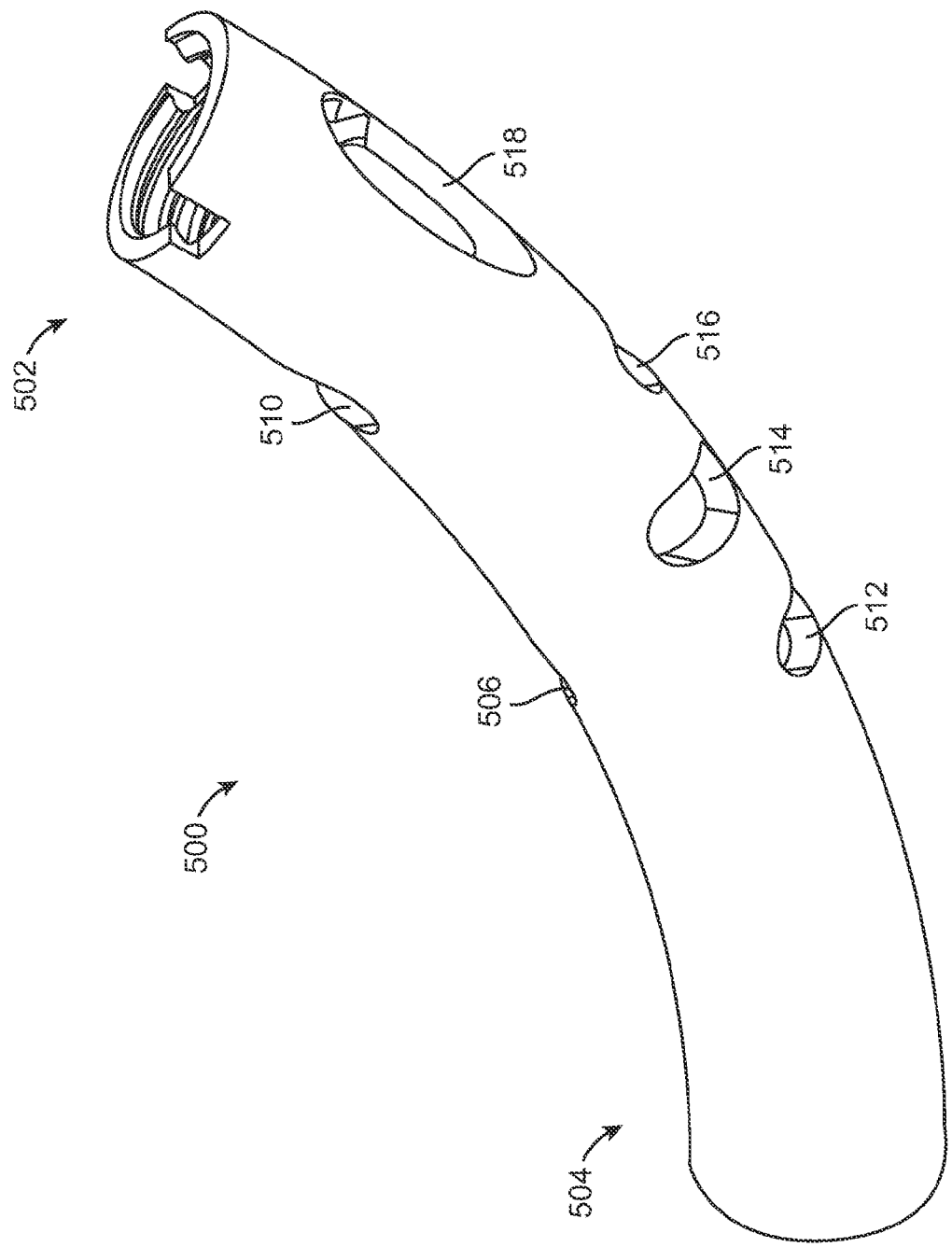
FIGS. 14A-14F show various views of another exemplary embodiment of a bone fixation device hub.
Figure 14B:
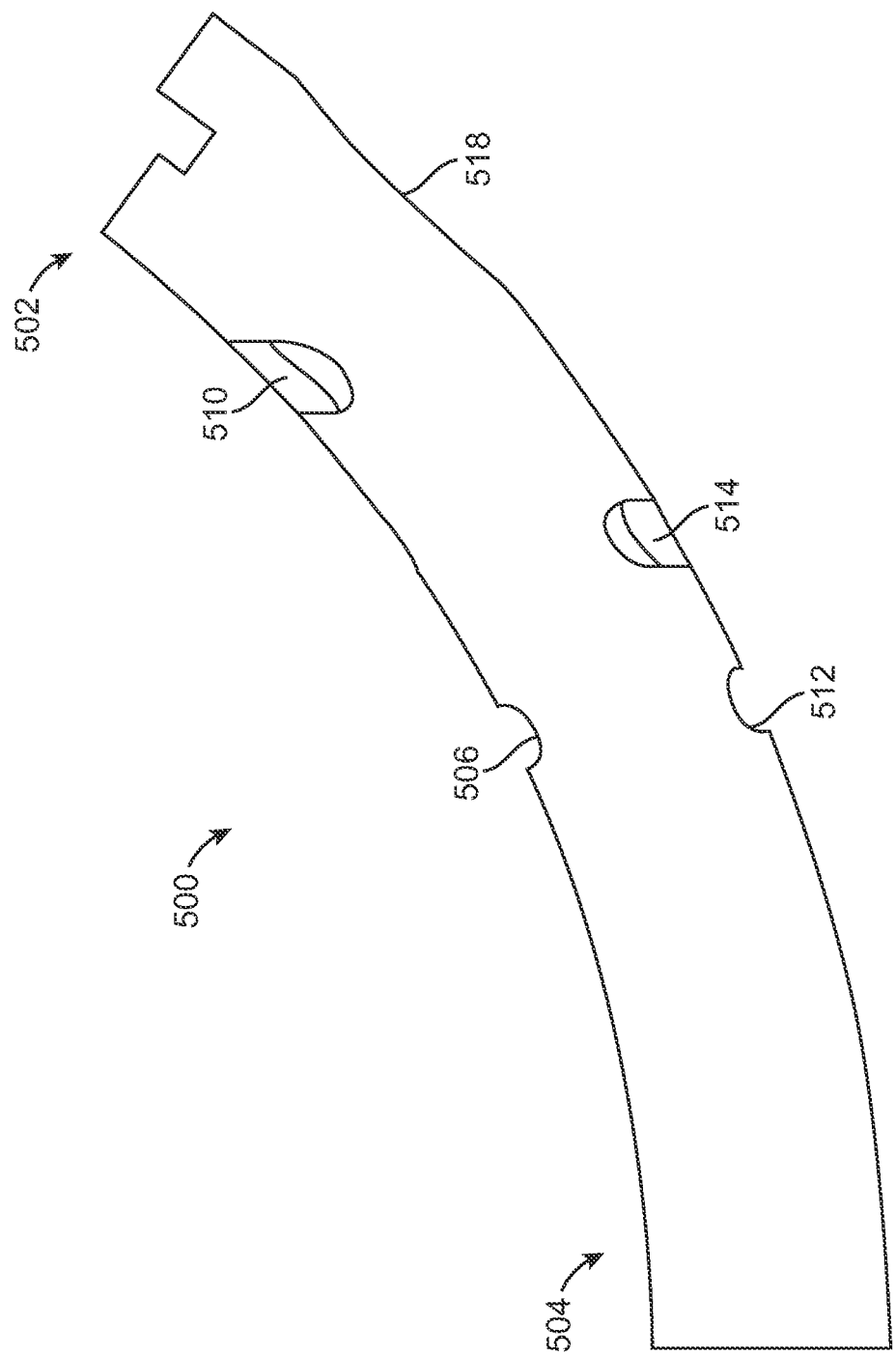
Figure 14C:
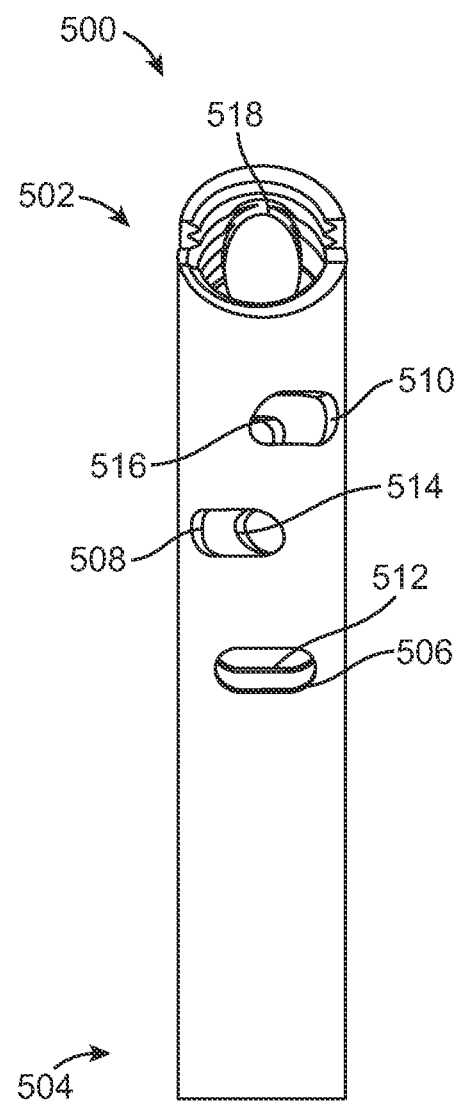
Figure 14D:
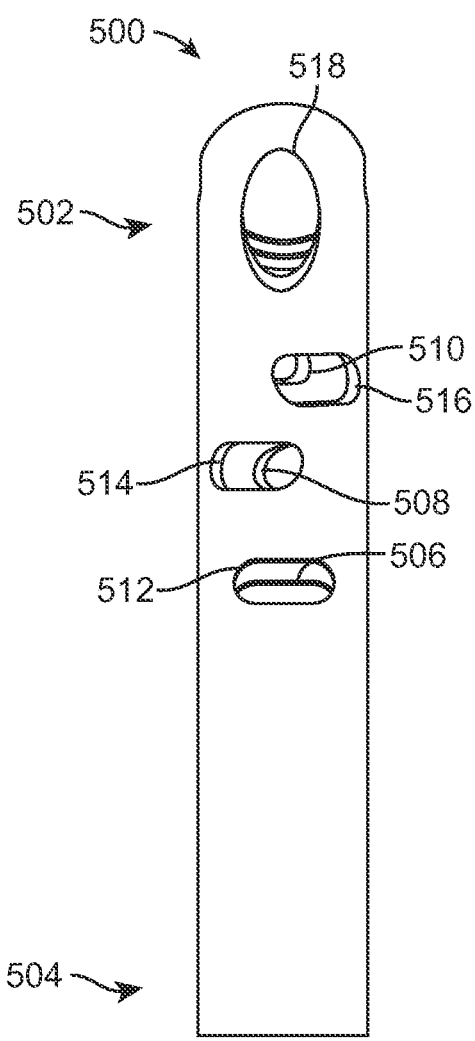

FIGS. 14A-14E show another exemplary embodiment of a bone fixation device hub 500. Hub 500 is of similar construction to hubs 400 and 450 described above and includes proximal end 502 and distal end 504. As best seen in FIG. 14C, hub 500 includes slotted holes 506, 508, and 510 through the wall thickness on its concave side. As best seen in FIG. 14D, hub 500 also includes slotted holes 512, 514, and 516, and angled hole 518 through the wall thickness on its convex side. Holes 506 and 512 on opposite sides of hub 500 are aligned to allow a first bone screw to be inserted through the two holes across the hub. Similarly, holes 508 and 514 are aligned to receive a second bone screw, and holes 510 and 516 are aligned to receive a third bone screw. Hole 518 is aligned with the opening in the proximal end 502 of hub 500 to receive a fourth bone screw.

The slotted configuration of hole pairs 506/512, 508/514, and 510/516 allows a bone screw to be received through each of the pairs in a variety of orientations. This arrangement permits a surgeon the flexibility to place bone screws where most appropriate in a particular procedure. For example, a first bone screw may be placed through holes 506 and 512 such that it resides in the left, middle, or right portion of hole 506, as viewed in FIG. 14C. The same screw will have another section that may reside in the left, middle, or right portion of hole 512. With these various combinations, it can be appreciated that the screw can take one of nine basic orientations through holes 506 and 512, as well as many other orientations between these nine. In other embodiments, a slightly enlarged round hole may be provided on one side of the hub while a slotted hole on the opposite side forms the other hole of the pair.

Figures 14E, 14F:
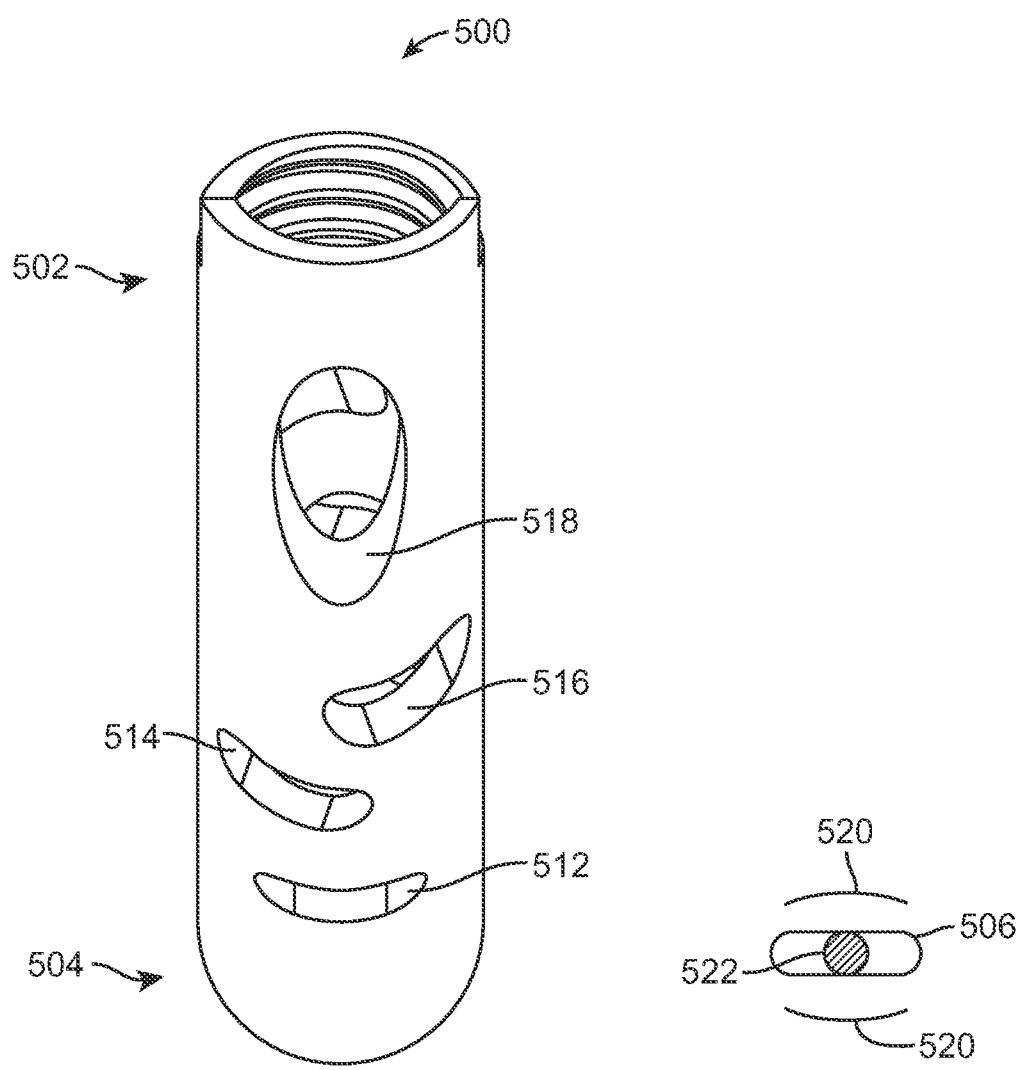

In this exemplary embodiment, the width of slotted holes 506, 508, 510, 512, 514, and 516 is 2.0 mm. This provides a pilot hole in which a drill bit or screw tip may engage. Material from a portion of the sides of each hole may be removed when the drill bit forms a larger hole in one location of the slotted hole, and/or when a screw is inserted to form threads through the hole. No drilling or threading may be necessary, such as when the slot width is generally the same as the minor diameter of the screw, and the thickness of the hub walls is generally the same as the screw pitch. The slotted holes may also stretch or deform when receiving the screw. As shown in FIG. 14F, relief slit(s) 520 may be provided adjacent to a slotted hole 506 to allow the slot to more easily expand when receiving a screw 522. Such slits may be formed by laser cutting, electron beam melting (EBM), electrical discharge machining (EDM), etching, stamping, milling, or other fabrication techniques.

Figure 15A:
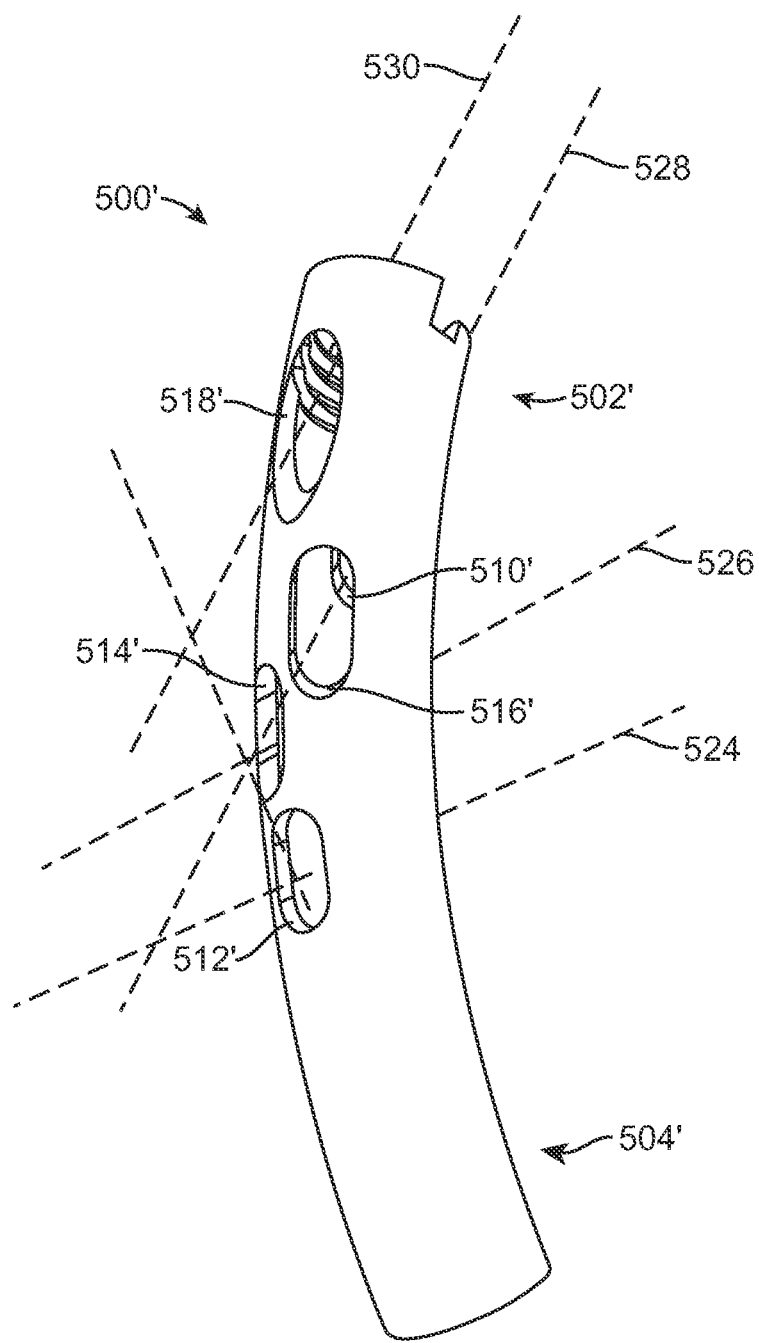
FIGS. 15A-15D show various views of another exemplary embodiment of a bone fixation device hub.
Figure 15B:
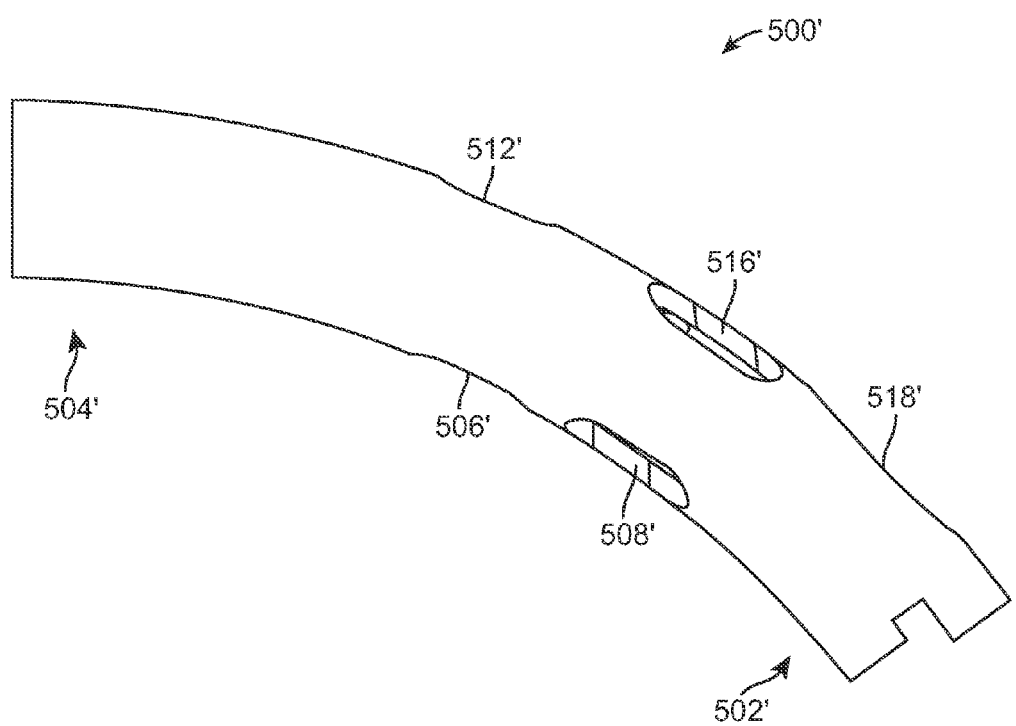
Figure 15C:
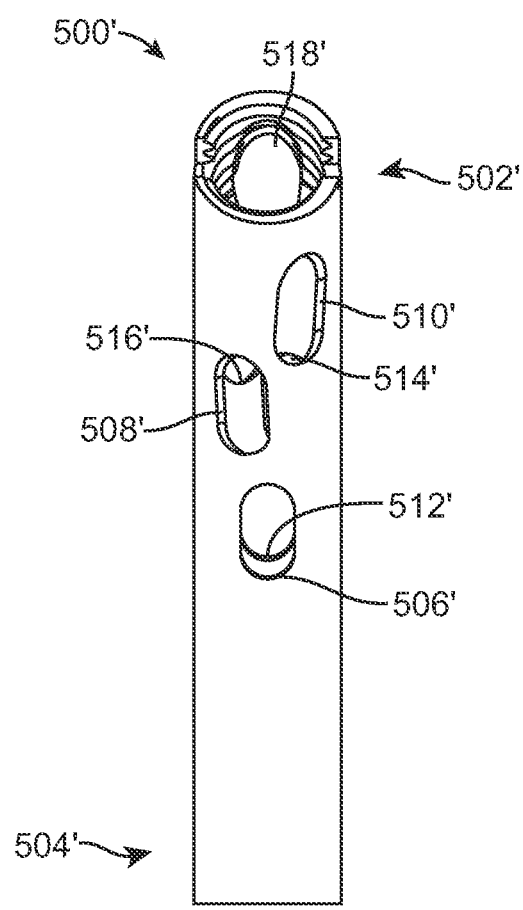
Figure 15D:
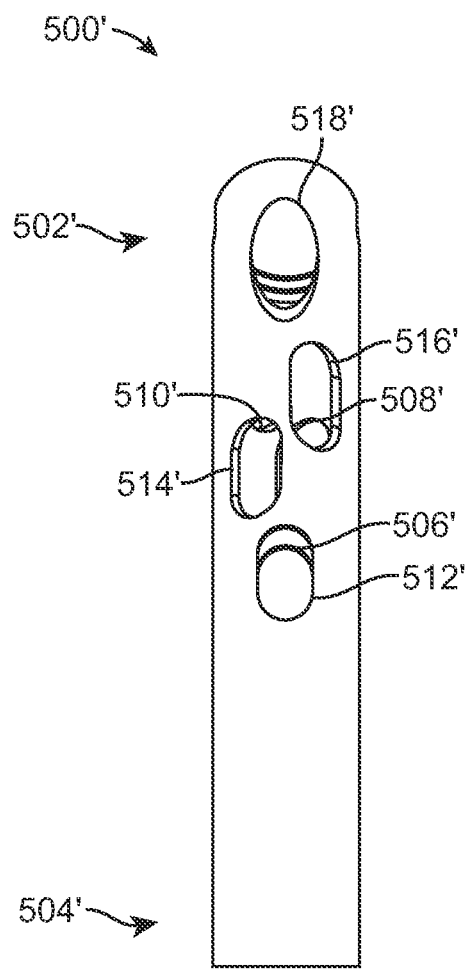

FIGS. 15A-15D show another exemplary embodiment of a bone fixation device hub 500'. Hub 500' is similar to hub 500 described above, but has slotted holes that are oriented longitudinally rather than transversely. Hub 500' includes proximal end 502' and distal end 504'. As best seen in FIG. 15C, hub 500' includes slotted holes 506', 508', and 510' through the wall thickness on its concave side. As best seen in FIG. 15D, hub 500' also includes slotted holes 512', 514', and 516', and angled hole 518' through the wall thickness on its convex side. Holes 506' and 512' on opposite sides of hub 500' are aligned to allow a first bone screw to be inserted through the two holes across the hub. Similarly, holes 508' and 514' are aligned to receive a second bone screw, and holes 510' and 516' are aligned to receive a third bone screw. Hole 518' is aligned with the opening in the proximal end 502' of hub 500' to receive a fourth bone screw. Exemplary axis lines 524, 526, 528, and 530 are shown in FIG. 15A to show examples paths for the first, second, third, and fourth screws, respectively.

Figure 16A:
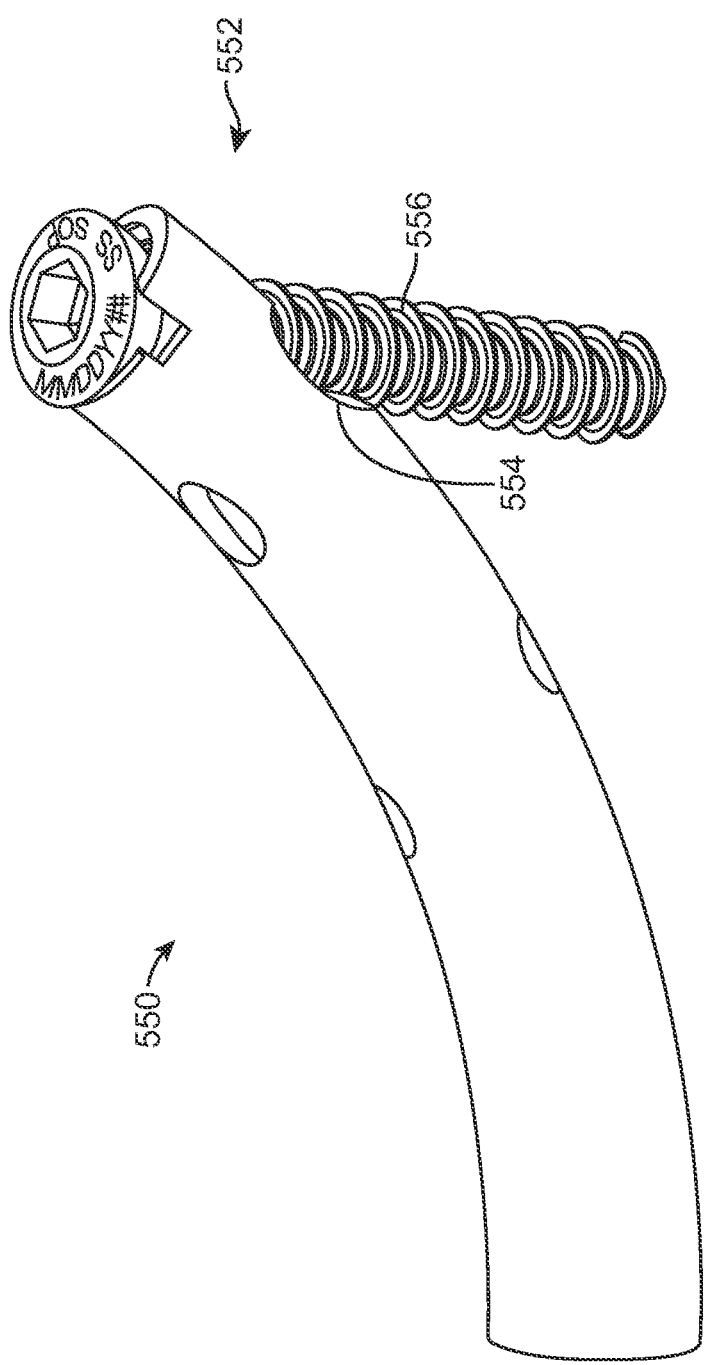
FIGS. 16A-16E show various views of another exemplary embodiment of a bone fixation device hub.
Figure 16B:
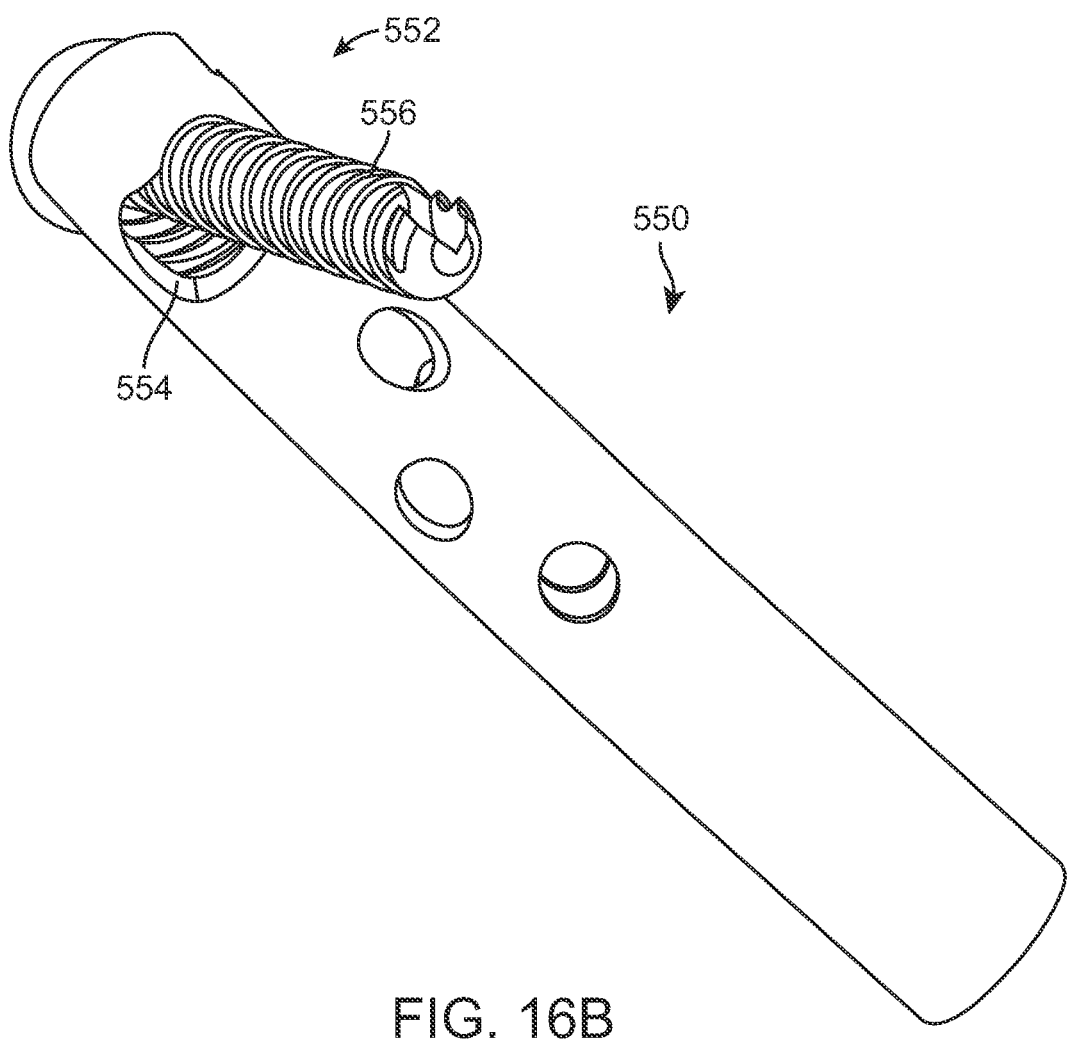
Figure 16C:
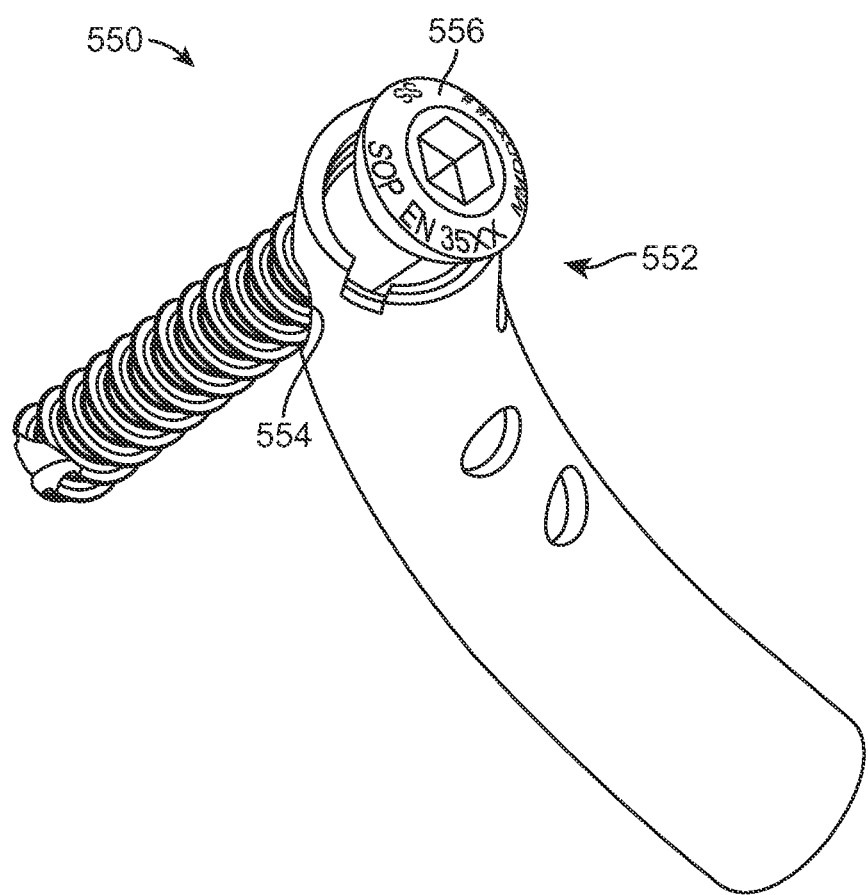
Figures 16D, 16E:
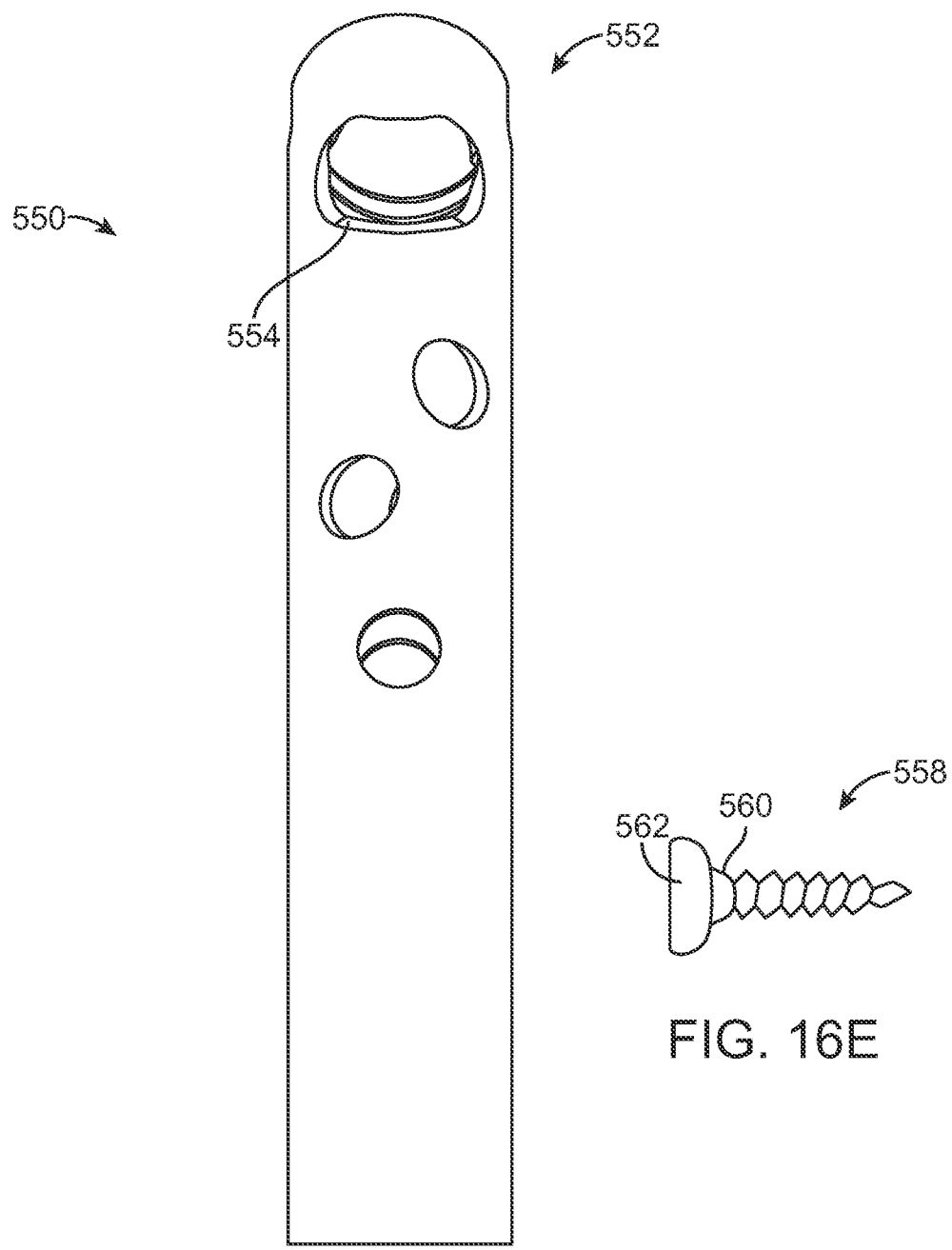

FIGS. 16A-16E show another exemplary embodiment of a bone fixation device hub 550. As best seen in FIG. 16D, hub 550 includes at its proximal end 552 a transversely elongated hole 554. Hole 554 allows a screw 556 to be located along the central axis, or off-axis in either direction as may be desired for engaging harder bone or securing additional bone fragment(s). This of arrangement of hole 554 may be configured to hold screw 556 tightly at all angles. This may be accomplished, for example, by using a hole 554 slot width that is equal to or smaller than the minor diameter of screw 556. The wall thickness of hub 550 may fit into the screw threads, providing additional locking of screw 556. In other embodiments, the angle of elongated hole 554 may be oriented differently as desired.

Special screws may be used to provide additional locking. As shown in FIG. 16E, screw 558 has a tapered edge 560 below its head 562. Tapered edge 560 serves to wedge screw 558 into slot 554, securing the screw in place. A screw with an expanding head (not shown) may also be used. With this arrangement, a taper or other expanded section may be created once the screw is in place, thereby locking it in position.

Figure 17A:
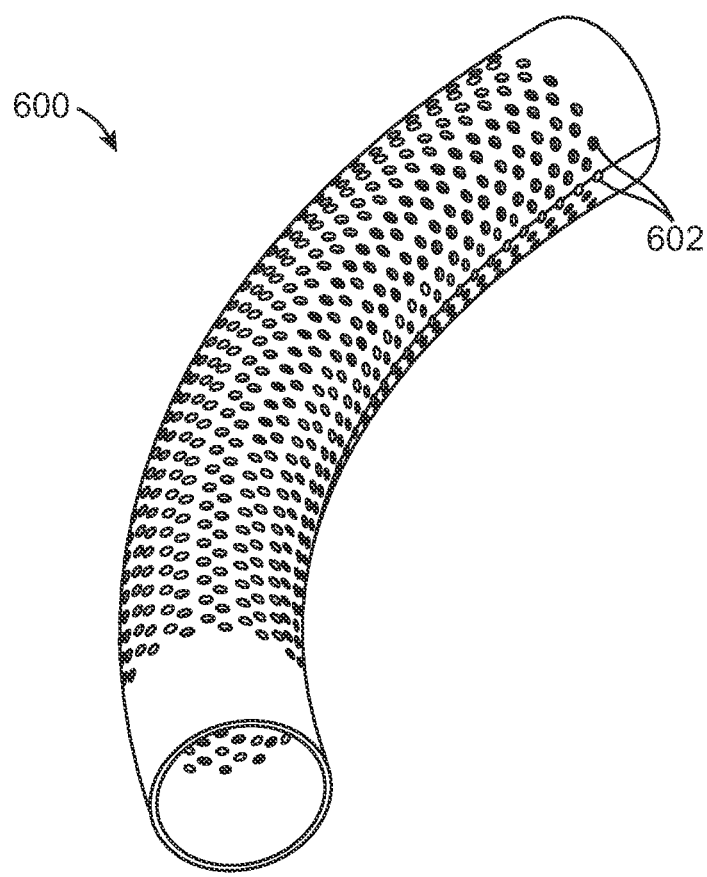
FIGS. 17A-17B show various views of another exemplary embodiment of a bone fixation device hub.
Figures 17B, 17C:
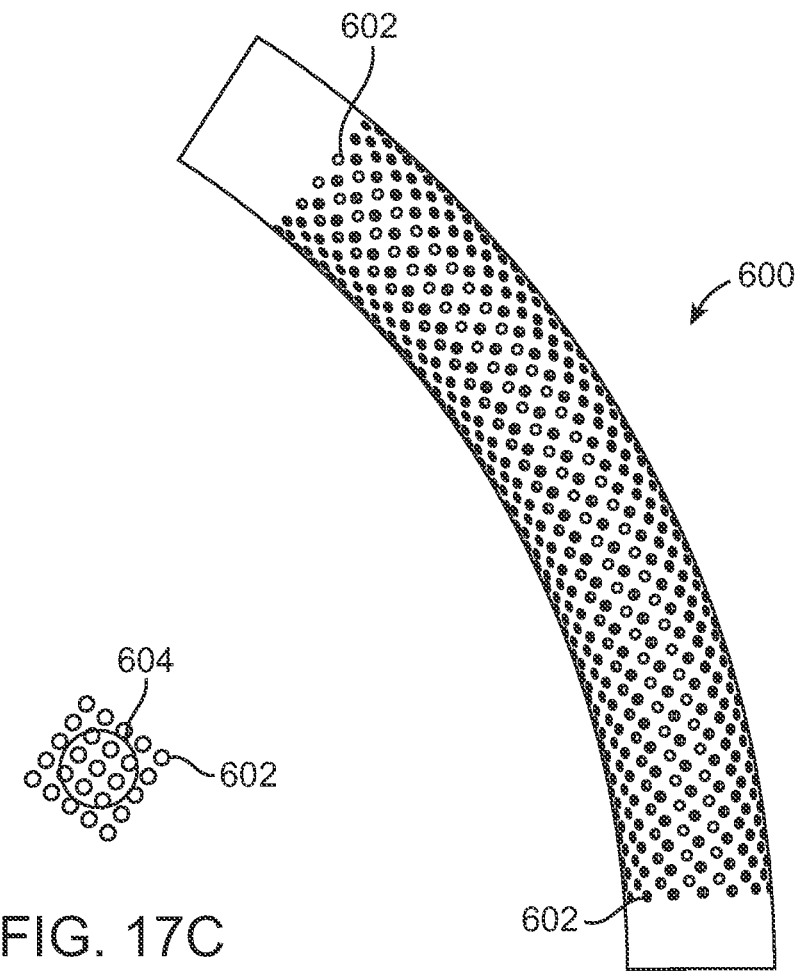

FIGS. 17A-17C show another exemplary embodiment of a bone fixation hub 600. Hub 600 is provided with an array of pilot holes 602 over most of its surface. Each hole 602 may be 0.015 to 0.020 inches in diameter, for example, and serves as a starting point to allow a drill bit or screw tip to penetrate the wall thickness of hub 600. This makes in vivo screw hole formation possible, while allowing the hub to remain a rigid structure. Holes 602 may be closely spaced such that a screw or screws may be positioned in vivo virtually anywhere the surgeon desires during each particular procedure. Once the drill bit and/or screw is inserted, the hole 602 becomes enlarged to generally the minor diameter of the screw thread, such as to 2.7 mm in diameter, for example. Screw holes may be formed in this way on both sides of hub 600 in a continuous operation, allowing screw(s) to be positioned across the hub as previously described.

As shown in FIG. 17C, pilot holes 602 may be placed closer to one another so that multiple perforations are consumed by the screw diameter 604 when the screw hole is formed. This can make in vivo hole formation even easier. Other hole patterns than those shown in FIGS. 17A-17C may be used.

Holes 602 may be fabricated in hub 600 by laser cutting, electron beam melting (EBM), electrical discharge machining (EDM), etching, stamping, drilling, or other fabrication techniques.

Figure 18A:
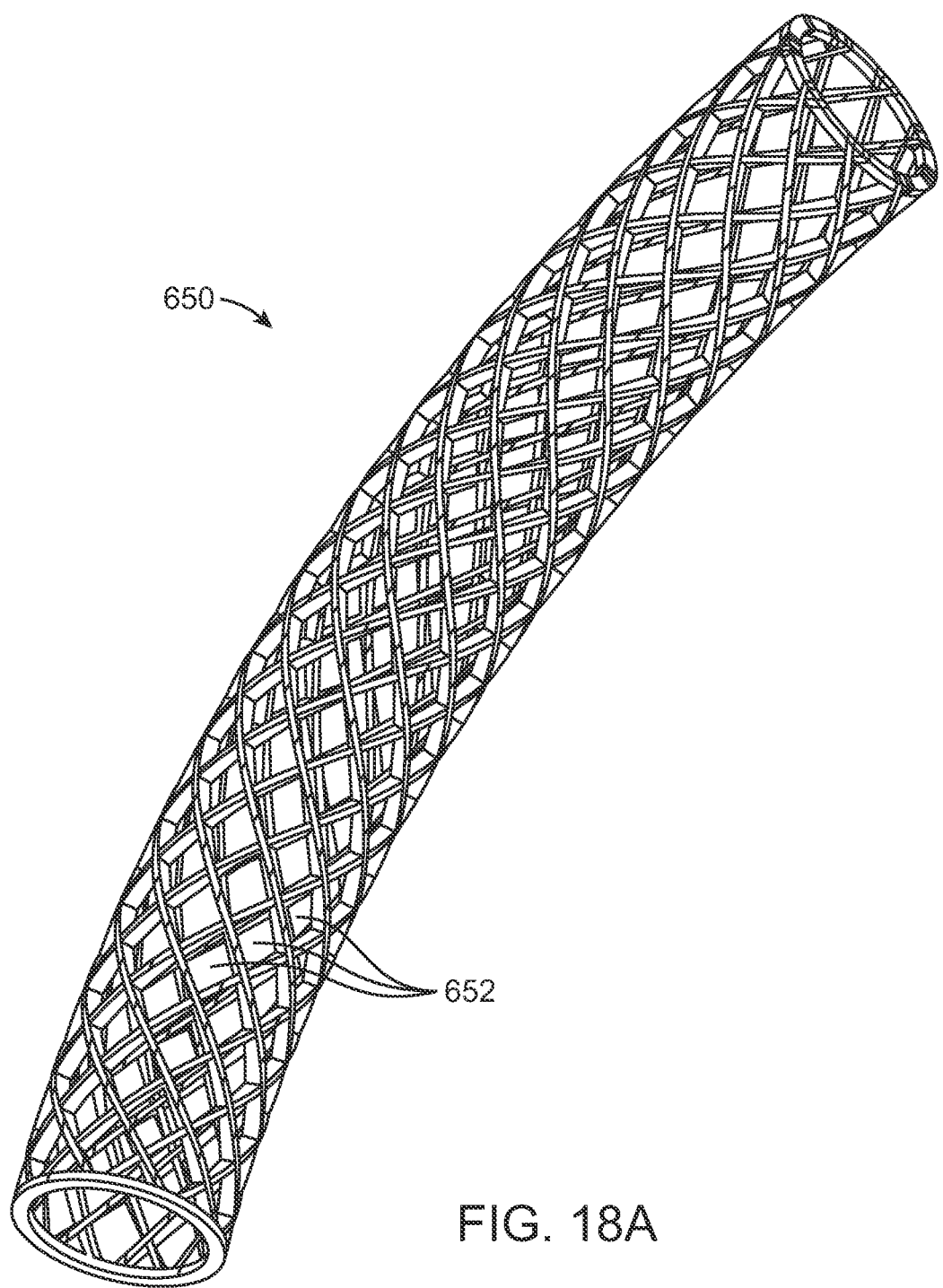
FIGS. 18A-18B show various views of another exemplary embodiment of a bone fixation device hub.
Figure 18B:
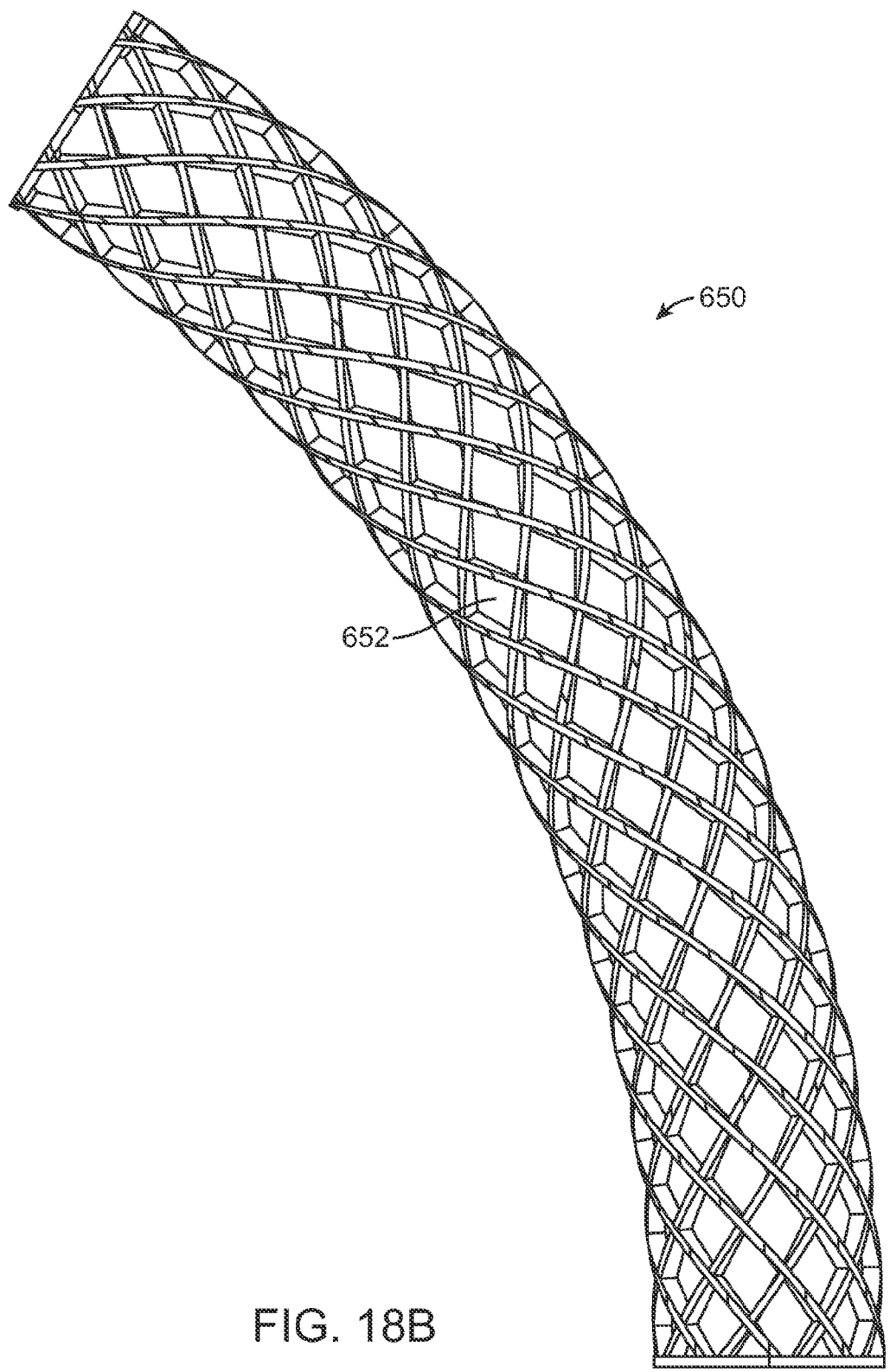

FIGS. 18A and 18B show another exemplary embodiment of a bone fixation hub 650. Hub 650 has at least a portion that is fabricated from a mesh structure, forming a plurality of diamond or other shaped apertures 652. Apertures 652 may be configured with dimensions smaller than the major diameter of the threads of the bone screws to be used. Aperture dimensions may even be smaller than the minor thread diameter, such that the apertures are stretched and/or deformed as the screw enters the aperture, thereby providing an increased ability to hold the screws in place. The use of a mesh hub 650 may reduce the amount or possibility of debris being formed and released inside the body during in vivo screw hole formation.

Apertures 652 may be fabricated in hub 650 by laser cutting, electron beam melting (EBM), electrical discharge machining (EDM), etching, stamping, drilling, or other fabrication techniques. Apertures 652 may also be fabricated by forming slits in plate or tube stock and expanding the material to form the apertures. Another fabrication technique that may be used is forming wires or bands around a mandrel and then welding, brazing, soldering, pressing, melting, gluing, or otherwise joining the wires or bands to each other at their intersections. Other types of porous structures, either with or without more random aperture locations, may be used as well. Multiple layers of mesh may also be combined.

Figure 19A:
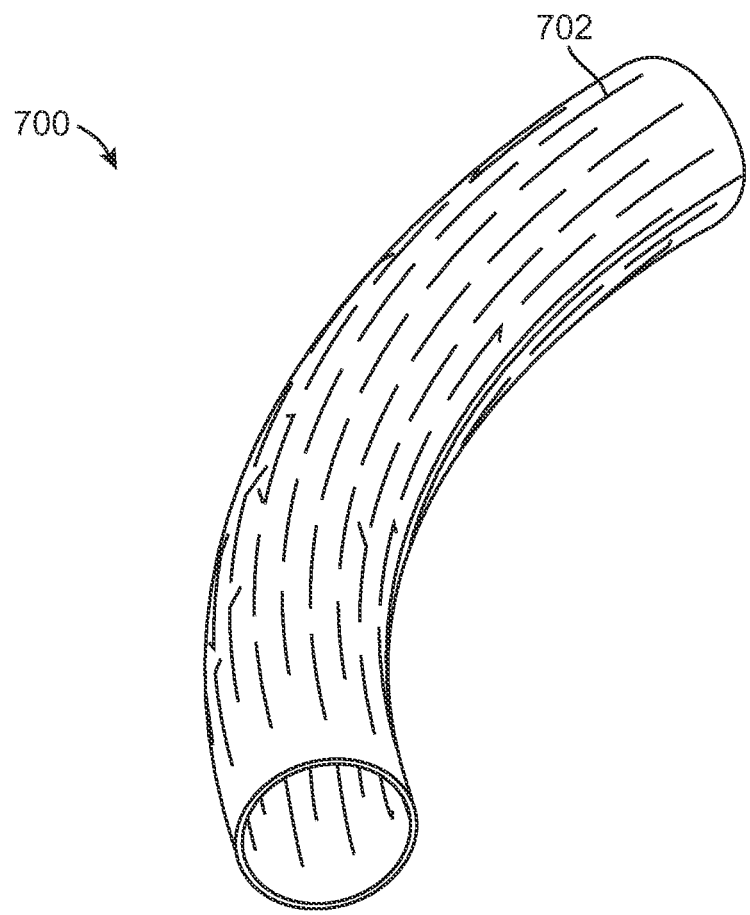
FIGS. 19A-19B show various views of another exemplary embodiment of a bone fixation device hub.
Figure 19B:
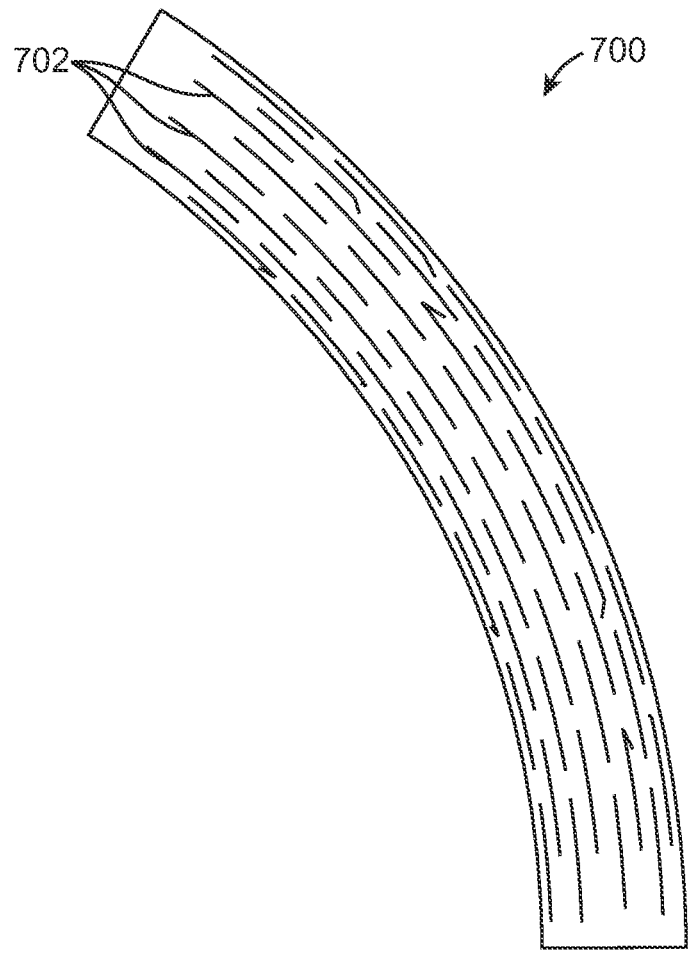

FIGS. 19A and 19B show another exemplary embodiment of a bone fixation hub 700. Hub 700 is provided with a plurality of thin slots 702 along its length. Slots 702 permit in vivo screw hole formation by acting as long pilot holes for drill bits or bone screws. A bone screw tip may be inserted into one of the slots 702 without pre-drilling. Upon insertion, the slot and surrounding slots will deform to make way for the screw, and will provide circumferential pressure to retain the screw.

Although shown staggered and in the longitudinal direction, in other embodiments (not shown) thin slots may be provided in a transverse or other orientation, and/or in other patterns. Slots 702 may be fabricated in hub 700 by laser cutting, electron beam melting (EBM), electrical discharge machining (EDM), etching, stamping, drilling, or other fabrication techniques. Thin slots 702 may generally require less material removal than other hub embodiments.

Figure 20A:
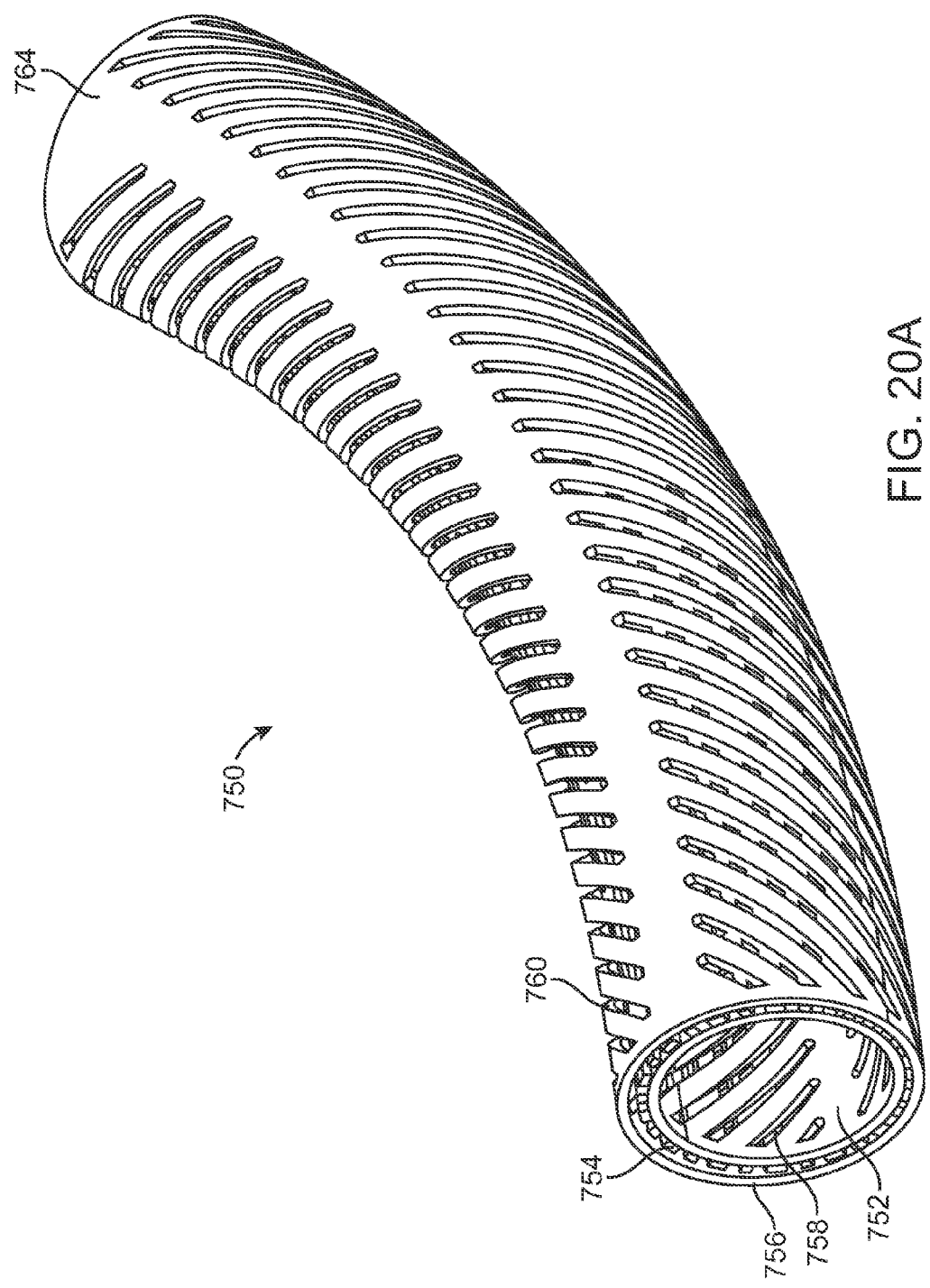
FIGS. 20A-20B show various views of another exemplary embodiment of a bone fixation device hub.
Figure 20B:
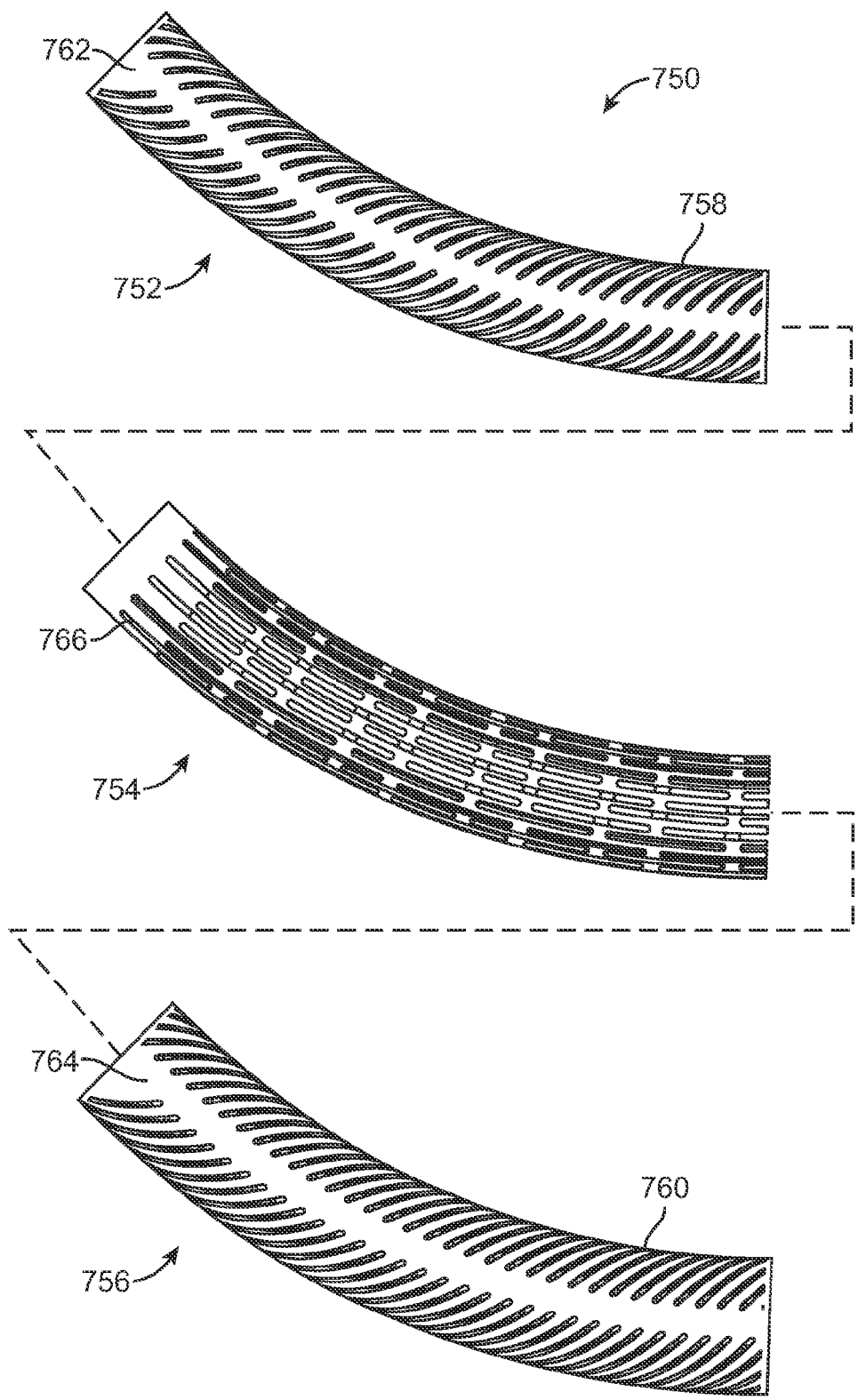

FIGS. 20A and 20B show another exemplary embodiment of a bone fixation hub 750. Hub 750 comprises three separately formed hubs assembled together: an inner hub 752, a mid-hub 754, and an outer hub 756. Mid-hub 754 has a larger diameter than inner hub 752 so that mid-hub 754 may be placed over inner hub 752, as illustrated in FIGS. 20A and 20B. Similarly, outer hub756 has a larger diameter than mid-hub 754 so that outer hub 756 may be placed over mid-hub 754, as also illustrated in the figures. In this embodiment, all three hub components 752, 754, and 756 have the same bend radius and the same arc length. Once assembled, the three hub components 752, 754, and 756 may be retained at one or both ends by other components of the associated bone fixation device, and/or may be welded or otherwise fastened together.

As seen in FIG. 20B, inner hub 752 and outer hub 756 have spirally formed slots 758 and 760, respectively. Slots 758 and 760 may be formed such that they line up when the individual hubs are assembled. Each hub 752 and 756 may also be provided with an upper spine (762 and 764, respectively), and a lower spine (not seen in FIG. 20B). The spines are solid regions running the length of the hubs that provide rigidity, and are positioned in areas that do not typically receive screws. Mid-hub 754 has longitudinally extending slots 766 rather than spiral slots. When the three slot patterns are assembled in a coaxial unit, as shown in FIG. 20A, a hub is formed that may be quite rigid. Pilot holes are formed where slots 760, 766, and 758 line up radially to facilitate in vivo screw hole formation. When a screw is inserted in such a pilot hole, one or more of the slots may deform to receive the screw.

One, two, three, four, or more hub layers may be used in this manner to form a single layer or composite hub. Other slot patterns and widths may be used as appropriate. Some of the layers may incorporate round or other aperture shapes instead of or in addition to the slots shown in this example.

In many of the hub embodiments described above, one or more screws may be placed into just a single side of the hub, or completely across the hub through both sides.

While exemplary embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:

1. An implantable bone fixation device comprising:
an elongate body having a flexible state and a rigid state;
wherein the flexible state comprises any of the group of bending, stretching, and deforming a material of the elongate body,
wherein the rigid state comprises limiting any of the group of bending, stretching, and deforming the material of the elongate body,
a tubular hub connected to a proximal end of the elongated body, the tubular hub comprising an outer surface and an inner surface of a tubular wall, the tubular wall comprising an array of pilot holes over a portion of the outer surface, each of the pilot holes being configured to expand upon receipt of a fastener there-through, wherein the hub comprises a mesh structure forming the array of pilot holes; and
an actuator operably connected to the elongate body for changing the body from the flexible state to the rigid state,
wherein a first position of the actuator places the elongate body in the flexible state and a second position of the actuator places the elongate body in the rigid state.

2. The implantable bone fixation device of claim 1, wherein the tubular hub comprises at least two layers, each layer comprising an array of slots, wherein the slots of the layers overlap to form the array of pilot holes in the tubular hub.

3. The implantable bone fixation device of claim 2, wherein each layer comprises a separately formed tubular hub.

4. The implantable bone fixation device of claim 2, wherein said slots are longitudinally formed.

5. The implantable bone fixation device of claim 2, wherein said slots are spirally formed.

6. The implantable bone fixation device of claim 1, wherein at least one pilot hole expands upon receipt of said fastener to a diameter of 2.7 mm.

7. The implantable bone fixation device of claim 1, wherein the tubular hub is rigid.

8. The implantable bone fixation device of claim 1, wherein at least one pilot hole is elongated to form a slot.

9. An implantable bone fixation device comprising:
an elongate body having a flexible state and a rigid state;
wherein the flexible state comprises any of the group of bending, stretching, and deforming a material of the elongate body,
a hub connected to a proximal end of the elongated body, the hub comprising a wall with an outer surface and an inner surface, the outer surface with a round cross-sectional shape, the inner surface with a round cross-sectional shape, the wall comprising a plurality of apertures over at least a portion of the outer surface;

wherein the hub comprises a mesh structure forming the plurality of apertures; and an actuator operably connected to the elongate body for changing the body from the flexible state to the rigid state;

wherein the plurality of apertures are configured to deform and to hold a fastener connected to the hub.

10. The implantable bone fixation device of claim 9, wherein the mesh structure comprises a plurality of diamond shaped apertures.

11. The implantable bone fixation device of claim 9, wherein at least one aperture expands upon receipt of said fastener to a diameter of 2.7 mm.

12. The implantable bone fixation device of claim 9, wherein the hub is rigid.

13. The implantable bone fixation device of claim 9, wherein the hub comprises at least two layers, each layer comprising a plurality of apertures.

14. The implantable bone fixation device of claim 13, wherein at least a portion of the plurality of apertures in a second layer of the hub overlap a portion of the plurality of apertures in a first layer of the hub.

15. The implantable bone fixation device of claim 14, wherein at least one aperture forms a pilot hole in the hub.

* * * * *